US012630840B2

(12) United States Patent
Wang et al.

(10) Patent No.: US 12,630,840 B2
(45) Date of Patent: May 19, 2026

(54) ONE-STEP GENE THERAPY FOR DUCHENNE MUSCULAR DYSTROPHY VIA GENE REPLACEMENT AND ANTI-INFLAMMATION

(71) Applicant: University of Pittsburgh—Of the Commonwealth System of Higher Education, Pittsburgh, PA (US)

(72) Inventors: Bing Wang, Cheswick, PA (US); Freddie Fu, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1247 days.

(21) Appl. No.: 17/427,814

(22) PCT Filed: Feb. 3, 2020

(86) PCT No.: PCT/US2020/016410
§ 371 (c)(1),
(2) Date: Aug. 2, 2021

(87) PCT Pub. No.: WO2020/160542
PCT Pub. Date: Aug. 6, 2020

(65) Prior Publication Data
US 2022/0136005 A1      May 5, 2022

Related U.S. Application Data

(60) Provisional application No. 62/800,484, filed on Feb. 2, 2019.

(51) Int. Cl.
| | |
|---|---|
| *C12N 15/86* | (2006.01) |
| *A61K 48/00* | (2006.01) |
| *A61P 21/00* | (2006.01) |
| *C07K 14/47* | (2006.01) |
| *C12N 15/113* | (2010.01) |

(52) U.S. Cl.
CPC .......... *C12N 15/86* (2013.01); *A61K 48/0058* (2013.01); *A61P 21/00* (2018.01); *C07K 14/4708* (2013.01); *C12N 15/113* (2013.01); *C12N 2310/122* (2013.01); *C12N 2310/531* (2013.01); *C12N 2320/31* (2013.01); *C12N 2320/32* (2013.01); *C12N 2750/14143* (2013.01); *C12N 2830/008* (2013.01)

(58) Field of Classification Search
CPC .................. C12N 15/86; C12N 15/113; C12N 2310/122; C12N 2310/531; C12N 2320/31; C12N 2320/32; C12N 2750/14143; C12N 2830/008; C12N 2330/51; C12N 2310/14; A61K 48/0058; A61P 21/00; C07K 14/4708; A01K 2217/075; A01K 2217/15; A01K 2227/105; A01K 2267/0306
See application file for complete search history.

(56) References Cited

U.S. PATENT DOCUMENTS

| | | | |
|---|---|---|---|
| 11,547,765 B2 * | 1/2023 | Xiao | C07K 14/78 |
| 2008/0064041 A1 | 3/2008 | Plavec et al. | |
| 2017/0368198 A1 * | 12/2017 | Xiao | A61K 48/0058 |
| 2020/0339960 A1 * | 10/2020 | Sahenk | A61P 25/00 |
| 2021/0403947 A1 * | 12/2021 | Banks | C07K 14/78 |

FOREIGN PATENT DOCUMENTS

| | | | | |
|---|---|---|---|---|
| WO | WO-2007108621 A1 * | 9/2007 | | C12N 15/113 |

OTHER PUBLICATIONS

Li C, Xiao P, Gray SJ, Weinberg MS, Samulski RJ. Combination therapy utilizing shRNA knockdown and an optimized resistant transgene for rescue of diseases caused by misfolded proteins. Proc Natl Acad Sci U S A. Aug. 23, 2011;108(34):14258-63. doi: 10.1073/pnas.1109522108. Epub Aug. 15, 2011. (Year: 2011).*

Himeda, C.L., Chen, X., Hauschka, S.D. (2011). Design and Testing of Regulatory Cassettes for Optimal Activity in Skeletal and Cardiac Muscles. In: Duan, D. (eds) Muscle Gene Therapy. Methods in Molecular Biology, vol. 709 pp. 3-20. Humana Press. https://doi.org/10.1007/978-1-61737-982-6_1 (Year: 2011).*

Efficacy, accumulation, and transcriptional profile of anti-HIV shRNAs expressed from human U6, 7SK, and H1 promoters Goguen, Ryan P. et al. Molecular Therapy—Nucleic Acids, vol. 23, 1020-1034 (Year: 2021).*

Makinen PI et al. Stable RNA interference: comparison of U6 and H1 promoters in endothelial cells and in mouse brain. J Gene Med. Apr. 2006;8(4):433-41. doi: 10.1002/jgm.860. PMID: 16389634. (Year: 2006).*

Ivanenkov et al. "Small Molecule Inhibitors of NF-κB and JAK/STAT Signal Transduction Pathways as Promising Anti-Inflammatory Therapeutics". Mini Rev Med Chem. Jan. 2011;11(1):55-78. doi: 10.2174/138955711793564079. PMID: 21034406 . . . (Year: 2011).*

Genbank Accession No. JN255693.1. *Homo sapiens* U6 snRNA gene, complete sequence, published May 31, 2012. (Year: 2012).*

Tang et al., "Gene Therapy Combined with NF-kappaB Inhibition for Duchenne Muscular Dystrophy", *Molecular Therapy*, vol. 21, No. 1, p. S111, Abstract 290 (2013).

(Continued)

*Primary Examiner* — Brian Whiteman
*Assistant Examiner* — Amanda M Zahorik
(74) *Attorney, Agent, or Firm* — Leydig, Voit & Mayer, Ltd

(57) ABSTRACT

In one embodiment, the invention provides a dual-cassette gene vehicle comprising cassettes for expression of both a mini-dystrophin gene and NF-κB/p65-shRNA gene in cardiac muscle tissue and skeletal muscle tissue, which is an adeno-associated viral (AAV) vector, wherein the mini-dystrophin gene is operably linked to a construct comprising a muscle-specific first promoter and a modified Mcken (MCK) enhancer and wherein the NF-κB/p65-shRNA gene is under the control of a second promoter. Also are provided pharmaceutical compositions comprising such gene vehicles and a method for ameliorating Duchenne muscular dystrophy (DMD) employing such gene delivery vehicles and pharmaceutical compositions.

23 Claims, 13 Drawing Sheets

Specification includes a Sequence Listing.

(56) References Cited

OTHER PUBLICATIONS

Wang et al., "Construction and analysis of compact muscle-specific promoters for AAV vectors", *Gene Therapy*, vol. 15, No. 22, pp. 1489-1499 (2008).

Acharyya et al., "Interplay of IKK/NF-KB signaling in macrophages and myofibers promotes muscle degeneration in Duchenne muscular dystrophy," *J. Clin. Invest.*, 117(4): 889-901 (2007).

Duan, "Systemic AAV Micro-distrophin Gene Therapy for Duchenne Muscular Dystrophy," *Mol. Ther.*, 26: 2337-2356 (2018).

Dunant et al., "Expression of Dystrophin Driven by the 1.35-kb MCK Promoter Ameliorates Muscular Dystrophy in Fast, but Not in Slow Muscles of Transgenic Mdx Mice," *Molecular Therapy*, 8(1): 80-89 (2003).

Jayandharan et al., "Activation of the NF-κB pathway by adena-associated virus (AAV) vectors and its implications in immune response and gene therapy," *PNAS*, 108(9): 3743-3748, Abstract (2011).

Jutooru et al., "Inhibition of NFkappaB and pancreatic cancer cell and tumor growth by curcumin is dependent on specificity protein down-regulation," *J. Biol. Chem.*, 285(33): 25332-25344 (2010).

Kornegay et al., "Widespread muscle expression of an AAV9 human mini-dystrophin vector after intravenous injection in neonatal dystrophin-deficient dogs," *Molecular Therapy*, 18(8): 1501-1508 (2010).

Lee et al., "Dual knockdown of p65 and p50 subunits of NF-kappaB by siRNA inhibits the induction of inflammatory cytokines and significantly enhance apoptosis in human primary synoviocytes treated with tumor necrosis factor-alpha," *Mol. Biol. Rep.*, 35: 291-298, Abstract (2008).

Mendell et al., "Dystrophin immunity in Duchenne's muscular dystrophy," *N. Engl. J. Med.*, 363(15): 1429-1437, Author Manuscript (2010).

Mu et al., "The role of Notch signaling in muscle progenitor cell depletion and the rapid onset of histopathology in muscular dystrophy," *Human Mol. Genet.*, 24(10): 2923-2937 (2015).

Tang et al., "Inhibition of the IKK/NF-KB pathway by AAV gene transfer improves muscle regeneration in older mdx mice," *Gene Ther.*, 17(12): 1476-1483, Author Manuscript (2010).

U.S. Patent and Trademark Office, International Search Report in PCT/US2020/016410, dated Apr. 21, 2021.

U.S. Patent and Trademark Office, Written Opinion in PCT/US2020/016410, dated Apr. 21, 2021.

Wang et al., "Adeno-associated virus vector carrying human minidystrophin genes effectively ameliorates muscular dystrophy in mdx mouse model," *Proc. Natl. Acad. Sci.*, 97(25): 13714-13719 (2000).

Wang et al., "Systemic human minidystrophin gene transfer improves functions and life span of dystrophin and dystrophin/utrophin-deficient mice," *Journal of Orthopaedic Research*, 27(4): 421-442, Abstract (2009).

Xiao et al., "Production of high-titer recombinant adeno-associated virus vectors in the absence of helper adenovirus," *J. Virol.*, 72(3): 2224-2232 (1998).

Yang et al., "AAV-based shRNA silencing of NF-κB ameliorates muscle pathologies in mdx mice," *Gene Therapy*, 19: 1196-1204 (2012).

Yin et al., "Genetic ablation of P65 subunit of NF-kappaB in mdx mice to improve muscle physiological function," *Muscle Nerve*, 56:759-767, Abstract (2017).

Kuang et al., "Optimizing Dystrophin Gene Therapy in Severe DMD Murine Model", *Molecular Therapy*, vol. 27, No. 4S1, p. 178, Abstract 374 (Apr. 2019).

Kuang et al., "Optimizing Dystrophin Gene Therapy in Severe DMD Murine Model", slide presentation associated with *Molecular Therapy*, vol. 27, No. 4S1, p. 178, Abstract 374 (Apr. 2019), presentation given at American Society of Gene & Cell Therapy 22nd Annual Meeting on Apr. 30, 2019 (22 pages).

Tang et al., "Gene Therapy Combined with NF-kappaB Inhibition for Duchenne Muscular Dystrophy", slide presentation associated with *Molecular Therapy*, vol. 21, No. 1, p. S111, Abstract 290 (2013), presentation given at American Society of Gene & Cell Therapy 16th Annual Meeting on May 17, 2013 (17 pages).

Pusch et al. "Nucleotide sequence homology requirements of HIV-1-specific short hairpin RNA." Nucleic Acids Res. 31(22):6444-9. (2003).

* cited by examiner

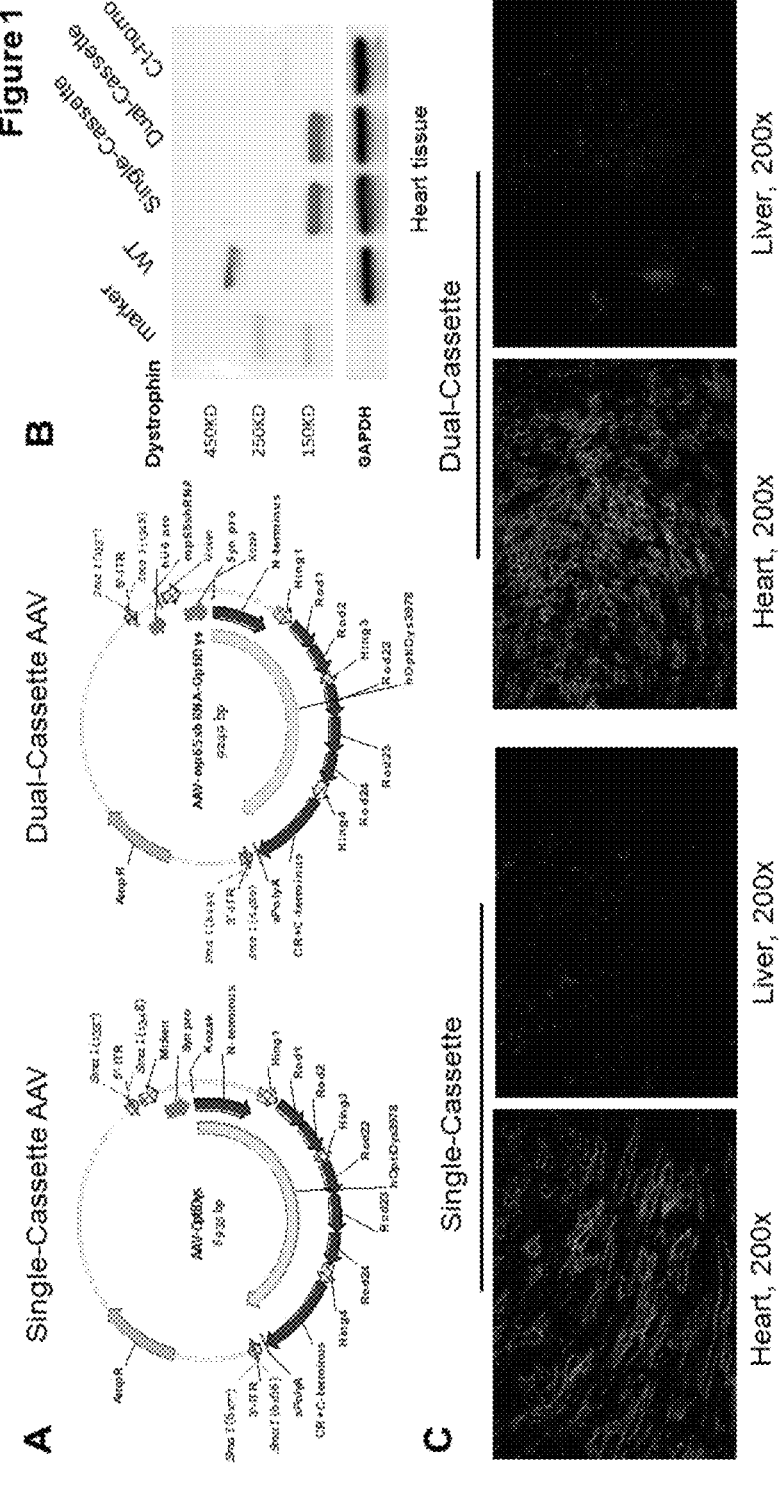

| SEQ ID NO (left) | pAAV-m1p65EnsynOpti3978 | Element | pAAV-m1p65EnsynOpti3978 | SEQ ID NO (right) |
|---|---|---|---|---|
| SEQ ID NO: 1 | | pAAV-m1p65EnsynOpti3978 | | SEQ ID NO: 23 |
| SEQ ID NO: 19 | 1269-1413 | 5'ITR (145bp) | 1269-1413 | SEQ ID NO: 19 |
| SEQ ID NO: 18 | 1452-1692 | U6 promoter (241bp) | 1452-1692 | SEQ ID NO: 18 |
| SEQ ID NO: 17 | 1701-1751 | m1-p65shRNA | 1701-1751 | SEQ ID NO: 22 |
| SEQ ID NO: 14 | 1757-1972 | Mck Enhancer (216bp) | 1757-1972 | SEQ ID NO: 14 |
| SEQ ID NO: 15 | 1973-2289 | Syn promoter (317bp) | 1973-2289 | SEQ ID NO: 15 |
| SEQ ID NO: 16 | 2359-2364 | Kozak sequence (6bp) | 2359-2364 | SEQ ID NO: 16 |
| SEQ ID NO: 3 | 2365-2367 | Start codon (ATG) | 2365-2367 | SEQ ID NO: 3 |
| SEQ ID NO: 4 | 2365-3120 | N-terminus (756bp) | 2365-3120 | SEQ ID NO: 4 |
| SEQ ID NO: 5 | 3121-3345 | Hinge 1 (225bp) | 3121-3345 | SEQ ID NO: 5 |
| SEQ ID NO: 6 | 3373-3705 | Rod1 (333bp) | 3373-3705 | SEQ ID NO: 6 |
| SEQ ID NO: 7 | 3706-4032 | Rod2 (327bp) | 3706-4032 | SEQ ID NO: 7 |
| SEQ ID NO: 8 | 4033-4173 | Hinge 3 (141bp) | 4033-4173 | SEQ ID NO: 8 |
| SEQ ID NO: 9 | 4174-4521 | Rod22 (348bp) | 4174-4521 | SEQ ID NO: 9 |
| SEQ ID NO: 10 | 4522-4908 | Rod23 (387bp) | 4522-4908 | SEQ ID NO: 10 |
| SEQ ID NO: 11 | 4909-5235 | Rod24 (327bp) | 4909-5235 | SEQ ID NO: 11 |
| SEQ ID NO: 12 | 5236-5451 | Hinge 4 (216bp) | 5236-5451 | SEQ ID NO: 12 |
| SEQ ID NO: 13 | 5452-6339 | CR domain (888bp) | 5452-6339 | SEQ ID NO: 13 |
| SEQ ID NO: 21 | 6340-6342 | Stop codon (TGA) | 6340-6342 | SEQ ID NO: 21 |
| SEQ ID NO: 20 | 6351-6410 | sPolyA (60bp) | 6351-6410 | SEQ ID NO: 20 |
| | 6414-6558 | 3'ITR (145bp) | 6414-6558 | |
| | 7394-8254 | AmpR (861bp) | 7394-8254 | |

Human codon Optimized Dys-3978 — SEQ ID NO: 2 (SEQ ID NO: 3 through SEQ ID NO: 13)

Figure 5B

| SEQ ID NO (m1) | pAAV-m1p65EasynOpti3837 | | pAAV-m2p65EasynOpti3837 | | SEQ ID NO (m2) |
|---|---|---|---|---|---|
| SEQ ID NO: 25 | (header) | | (header) | | SEQ ID NO: 26 |
| SEQ ID NO: 19 | 5'ITR (145bp) | 1269-1413 | 1269-1413 | 5'ITR (145bp) | SEQ ID NO: 19 |
| SEQ ID NO: 18 | U6 promoter (241bp) | 1452-1692 | 1452-1692 | U6 promoter (241bp) | SEQ ID NO: 18 |
| SEQ ID NO: 17 | m1-p65shRNA | 1701-1731 | 1701-1731 | M2-p65shRNA | SEQ ID NO: 22 |
| SEQ ID NO: 14 | Mck Enhancer (216bp) | 1757-1972 | 1757-1972 | Mck Enhancer (216bp) | SEQ ID NO: 14 |
| SEQ ID NO: 15 | Syn promoter (317bp) | 1973-2289 | 1973-2289 | Syn promoter (317bp) | SEQ ID NO: 15 |
| SEQ ID NO: 16 | Kozak sequence (6bp) | 2359-2364 | 2359-2364 | Kozak sequence (6bp) | SEQ ID NO: 16 |
|  | Start codon (ATG) | 2365-2367 | 2365-2367 | Start codon (ATG) |  |
| SEQ ID NO: 3 | N-terminus (756bp) | 2365-3120 | 2365-3120 | N-terminus (756bp) | SEQ ID NO: 3 |
| SEQ ID NO: 4 | Hinge 1 (225bp) | 3121-3345 | 3121-3345 | Hinge 1 (225bp) | SEQ ID NO: 4 |
| SEQ ID NO: 5 | Rod1 (333bp) | 3373-3705 | 3373-3705 | Rod1 (333bp) | SEQ ID NO: 5 |
| SEQ ID NO: 6 | Rod2 (327bp) | 3706-4032 | 3706-4032 | Rod2 (327bp) | SEQ ID NO: 6 |
| SEQ ID NO: 8 | Rod22 (348bp) | 4035-4380 | 4035-4380 | Rod22 (348bp) | SEQ ID NO: 8 |
| SEQ ID NO: 9 | Rod23 (387bp) | 4381-4767 | 4381-4767 | Rod23 (387bp) | SEQ ID NO: 9 |
| SEQ ID NO: 10 | Rod24 (327bp) | 4768-5094 | 4768-5094 | Rod24 (327bp) | SEQ ID NO: 10 |
| SEQ ID NO: 11 | Hinge 4 (216bp) | 5095-5310 | 5095-5310 | Hinge 4 (216bp) | SEQ ID NO: 11 |
| SEQ ID NO: 12 | CR domain (888bp) | 5311-6198 | 5311-6198 | CR domain (888bp) | SEQ ID NO: 12 |
| SEQ ID NO: 13 | Stop codon (TGA) | 6199-6201 | 6199-6201 | Stop codon (TGA) | SEQ ID NO: 13 |
| SEQ ID NO: 21 | sPolyA (60bp) | 6210-6269 | 6210-6269 | sPolyA (60bp) | SEQ ID NO: 21 |
| SEQ ID NO: 20 | 3'ITR (145bp) | 6273-6417 | 6273-6417 | 3'ITR (145bp) | SEQ ID NO: 20 |
|  | AmpR (861bp) | 7233-8113 | 7233-8113 | AmpR (861bp) |  |

Human codon Optimized Dys-3837 — SEQ ID NO: 27 (bracket spanning SEQ ID NO: 3 through SEQ ID NO: 13)

Figure 6B

SEQUENCE LISTING

```
<160> NUMBER OF SEQ ID NOS: 27

<210> SEQ ID NO 1
<211> LENGTH: 9249
<212> TYPE: DNA
<213> ORGANISM: Artificial Sequence
<220> FEATURE:
<223> OTHER INFORMATION: Synthetic

<400> SEQUENCE: 1
aattcccatc atcaataata taccttattt tggattgaag ccaatatgat aatgaggggg       60
```

-continued

```
tggagtttgt gacgtggcgc ggggcgtggg aacggggcgg gtgacgtagt agtctctaga     120
ggtccccagc gaccttgacg ggcatctgcc cggcatttct gacagctttg tgaactgggt     180
ggccgagaag gaatgggagt tgccgccaga ttctgacatg gatctgaatc tgattgagca     240
ggcacccctg accgtggccg agaagctgca tcgctggcgt aatagcgaag aggcccgcac     300
cgatcgccct tcccaacagt tgcgcagcct gaatggcgaa tggaattcca gacgattgag     360
cgtcaaaatg taggtatttc catgagcgtt tttcctgttg caatggctgg cggtaatatt     420
gttctggata ttaccagcaa ggccgatagt ttgagttctt ctactcaggc aagtgatgtt     480
attactaatc aaagaagtat tgcgacaacg gttaatttgc gtgatggaca gactctttta     540
ctcggtggcc tcactgatta taaaaacact tctcaggatt ctggcgtacc gttcctgtct     600
aaaatccctt taatcggcct cctgtttagc tcccgctctg attctaacga ggaaagcacg     660
ttatacgtgc tcgtcaaagc aaccatagta cgcgccctgt agcggcgcat taagcgcggc     720
gggtgtggtg gttacgcgca gcgtgaccgc tacacttgcc agcgccctag cgcccgctcc     780
tttcgctttc ttcccttcct ttctcgccac gttcgccggc tttccccgtc aagctctaaa     840 tcggggggctc cctttagggt tccgatttag tgctttacgg cacctcgacc ccaaaaaact     900
tgattagggt gatggttcac gtagtgggcc atcgccctga tagacggttt ttcgcccttt     960
gacgttggag tccacgttct ttaatagtgg actcttgttc caaactggaa caacactcaa    1020
ccctatctcg gtctattctt ttgatttata agggattttg ccgatttcgg cctattggtt    1080
aaaaaatgag ctgatttaac aaaaatttaa cgcgaatttt aacaaaatat taacgtttac    1140
aatttaaata tttgcttata caatcttcct gtttttgggg cttttctgat tatcaaccgg    1200
ggtacatatg attgacatgc tagtttttacg attaccgttc atcgcctgca gggggggggg    1260
ggggggggtt ggccactccc tctctgcgcg ctcgctcgct cactgaggcc gggcgaccaa    1320
aggtcgcccg acgcccgggc tttgcccggg cggcctcagt gagcgagcga gcgcgcagag    1380
agggagtggc caactccatc actaggggtt cctagatctg aattcgagct tgccacgcat    1440
gcgggcagga agagggccta tttcccatga ttccttcata tttgcatata cgatacaagg    1500
ctgttagaga gataattaga attaatttga ctgtaaacac aaagatatta gtacaaaata    1560
cgtgacgtag aaagtaataa tttcttgggt agtttgcagt tttaaaatta tgttttaaaa    1620
tggactatca tatgcttacc gtaacttgaa agtatttcga tttcttggct ttatatatct    1680
tgtggaaagg acgaggatcc tgtgtccatt gtctcactcc tcgaggagtg agacaatgga    1740
cacatttttt tgaattccac tacgggtcta ggctgcccat gtaaggaggc aaggcctggg    1800
gacacccgag atgcctggtt ataattaacc ccaacacctg ctgcccccccc ccccccaaca    1860 cctgctgcct gagcctgagc ggttacccca ccccggtgcc tgggtcttag gctctgtaca    1920
ccatggagga gaagctcgct ctaaaaataa ccctgtccct ggtggatccc ctgcatgcgg    1980
ccgtccgccc tcggcaccat tcctcacgac accgaaatat ggcgacgggt gaggaatggt    2040
ggggagttat ttttagagcg gtgaggaatg gtgggcaggc agcaggtgtt gggggagtta    2100 ttttttagagc ggggagttat ttttagagcg gtgaggaatg gtggacaccg aaatatggcg    2160
acgggtgagg aatggtgccg tcgccatatt tgggtgtccc gtccgccctc ggccggggcc    2220
gcattcctgg gggccgggcg gtgctcccgc ccgcctcgat aaaaggctcc ggggccggcg    2280
gcggcccact cgagacgttg taaaacgacg gccagtgagc gcgcgtaata cgactcacta    2340
tagggcgaat gggtaccgc caccatggtg tggtgggagg aagtggagga ctgctacgag    2400
agagaggacg tgcagaagaa aaccttcacc aagtgggtga cgcccagtt cagcaagttc    2460
```

-continued

```
ggcaagcagc acatcgagaa cctgttcagc gacctgcagg atggcaggag actgctggac    2520
ctgctggagg gcctgaccgg ccagaagctg cccaaggaga agggcagcac cagagtgcac    2580
gccctgaaca acgtgaacaa ggccctgaga gtgctgcaga caacaacgt ggacctggtg      2640 aacatcggca gcaccgacat cgtggacggc aaccacaagc tgaccctggg cctgatctgg     2700
aacatcatcc tgcactggca ggtgaagaac gtgatgaaga acatcatggc cggcctgcag     2760
cagaccaaca gcgagaagat cctgctgagc tgggtgaggc agagcaccag aaactacccc     2820
caggtgaacg tgatcaactt caccacctcc tggagcgacg gcctggccct gaacgccctg     2880
atccacagcc acagacccga cctgttcgac tggaacagcg tggtgtgtca gcagagcgcc     2940
acccagagac tggagcacgc cttcaacatc gccagatacc agctgggcat cgagaagctg      3000
ctggaccccg aggacgtgga caccacctac cccgacaaga aaagcatcct catgtacatt      3060
accagcctgt tccaggtgct gccccagcag gtgtccatcg aggccatcca ggaagtggaa      3120
atgctgccca ggcccccaa agtgaccaag gaggagcact tccagctgca ccaccagatg        3180
cactacagcc agcagatcac agtgagcctg gcccagggct atgagagaac cagcagcccc      3240
aagcccagat tcaagagcta cgcctacacc caggccgcct acgtgaccac ctccgacccc       3300
accagaagcc ccttcccccag ccagcacctg gaggcccccg aggacaagag cttcggcagc      3360
agcctgatgg agagcgaagt gaacctggac agataccaga ccgccctgga ggaagtgctg      3420
tcctggctgc tgagcgccga ggacaccctg caggcccagg gcgagatcag caacgacgtg       3480
gaagtggtga aggaccagtt ccacacccac gagggctaca tgatggatct gaccgcccac      3540
cagggcagag tgggcaatat cctgcagctg ggcagcaagc tgatcggcac cggcaagctg      3600
agcgaggacg aggagaccga agtgcaggag cagatgaacc tgctgaacag cagatgggag       3660
tgcctgagag tggccagcat ggagaagcag agcaacctgc acagagtgct gatggacctg      3720
cagaaccaga agctgaagga gctgaacgac tggctgacca agaccgagga gcggaccaga       3780
aagatggagg aggagcccct gggcccccgac ctggaggacc tgaagagaca ggtgcagcag      3840
cacaaagtgc tgcaggagga cctggagcag gagcaggtgc gcgtgaacag cctgacccac      3900
atggtggtgg tcgtggacga gagcagcggc gaccacgcca cagccgcect ggaagagcag      3960 ctgaaagtgc tgggcgacag atgggccaat atttgtaggt ggaccgagga cagatgggtg      4020
ctgctgcagg accagcccga cctggcccct ggcctgacca ccatcggcgc cagccccacc      4080
cagaccgtga ccctggtgac ccagcccgtg gtgacaaagg agaccgccat cagcaagctg       4140
gagatgccca gctccctgat gctggaagtg cccacccacc gcctgctcca gcagttcccc      4200
ctggacctgg agaagttcct ggcctggctg accgaggccg aaaccaccgc caatgtgctc      4260
caggacgcca ctagaaagga gaggctgctg gaggacagca agggcgtgaa agagctgatg      4320
aagcagtggc aggatctgca gggcgaaatc gaggcccaca ccgacgtgta ccacaacctg      4380
gacgagaaca gccagaagat tctgaggagc ctggagggca gcgacgacgc cgtcctgctc      4440
cagaggaggc tggacaacat gaacttcaag tggagcgagc tgcggaagaa gagcctgaac     4500
atccggagcc acctggaagc cagcagcgac cagtggaaga gactgcacct gagcctgcag      4560
gagctgctgg tgtggctgca gctgaaggac gacgagctga gcagacaggc ccccatcggc      4620
ggcgacttcc ccgccgtgca gaagcagaac gacgtgcacc gggccttcaa gagggagctg      4680
aaaaccaagg aacccgtgat catgagcacc ctggagacag tgcggatctt cctgaccgag      4740
cagcccctgg agggactgga gaagctgtac caggagccca gagagctgcc ccccgaggag     4800
```

-continued

```
agagcccaga acgtgaccag gctgctgaga aagcaggccg aggaagtgaa taccgagtgg    4860
gagaagctga atctgcacag cgccgactgg cagagaaaga tcgacgagac cctggagaga    4920
ctccaggaac tgcaggaagc caccgacgag ctggacctga agctgagaca ggccgaagtg    4980
atcaagggca gctggcagcc tgtgggcgat ctgctgatcg actccctgca ggatcacctg    5040
gagaaagtga aggccctgcg gggcgagatc gcccccctga aggagaatgt gagccacgtg    5100
aacgacctgg ccagacagct gaccaccctg ggcatccagc tgagcccct a caacctgagc    5160 acactggagg atctgaacac ccggtggaaa ctgctgcagg tggccgtgga ggatagagtg    5220
aggcagctgc acgaagccca cagagacttc ggccctgcct cccagcactt cctgagcacc    5280
agcgtgcagg gcccctggga gagagccatc tcccccaaca aagtgcccta ctacatcaac    5340
cacgagaccc agaccacctg ctgggaccac cctaagatga ccgagctgta tcagagcctg    5400
gccgacctga acaatgtgcg gttcagcgcc tacagaaccg ccatgaagct gcggagactg    5460
cagaaggccc tgtgcctgga tctgctgagc ctgagcgccg cctgcgacgc cctggaccag    5520
cacaacctga agcagaatga ccagcccatg gacatcctgc agatcatcaa ctgcctgacc    5580
acaatctacg accggctgga acaggagcac aacaacctgg tgaatgtgcc cctgtgcgtg    5640
gacatgtgcc tgaattggct gctgaacgtg tacgacaccg gcaggaccgg cagaatccgc    5700
gtgctgagct tcaagaccgg catcatcagc ctgtgcaagg cccacctgga ggataagtac    5760
cgctacctgt tcaagcaggt ggccagcagc accggcttct gcgatcagag gagactgggc    5820
ctgctgctgc acgatagcat ccagatccct aggcagctgg gcgaagtggc cagctttggc    5880
ggcagcaaca tcgagccctc tgtgaggagc tgcttccagt tcgccaacaa caagcccgag    5940
atcgaggccg ccctgttcct ggactggatg aggctggagc tcagagcat ggtgtggctg    6000 cctgtgctgc acagagtggc cgccgccgag accgccaagc accaggccaa gtgcaatatc    6060
tgcaaggagt gccccatcat cggcttccgg tacaggagcc tgaagcactt caactacgac    6120
atctgccaga gctgctttt t cagcggcaga gtggccaagg ccacaaaat gcactacccc    6180 atggtggagt actgcacccc caccacctcc ggcgaggatg tgagagactt cgccaaagtg    6240
ctgaagaata agttccggac caagcggtac tttgccaagc accccaggat gggctacctg    6300
cccgtgcaga ccgtgctgga aggcgacaac atggagacct gatgaggagc tcgaggccta    6360
ataaagagct cagatgcatc gatcagagtg tgttggtttt ttgtgtgaga tctaggaacc    6420
cctagtgatg gagttggcca ctccctctct gcgcgctcgc tcgctcactg aggccgcccg    6480
ggcaaagccc gggcgtcggg cgacctttgg tcgcccggcc tcagtgagcg agcgagcgcg    6540
cagagaggga gtggccaacc cccccccccc cccccctgca ggcgattctc ttgtttgctc    6600
cagactctca ggcaatgacc tgatagcctt tgtagagacc tctcaaaaat agctaccctc    6660
tccggcatga atttatcagc tagaacggtt gaatatcata ttgatggtga tttgactgtc    6720
tccggccttt ctcacccgtt tgaatcttta cctacacatt actcaggcat tgcatttaaa    6780
atatatgagg gttctaaaaa tttttatcct tgcgttgaaa taaaggcttc tcccgcaaaa    6840
gtattacagg gtcataatgt ttttggtaca accgatttag ctttatgctc tgaggcttta    6900
ttgcttaatt ttgctaattc tttgccttgc ctgtatgatt tattggatgt tggaattcct    6960
gatgcggtat tttctcctta cgcatctgtg cggtatttca caccgcatat ggtgcactct    7020
cagtacaatc tgctctgatg ccgcatagtt aagccagccc cgacacccgc caacacccgc    7080
tgacgcgccc tgacgggctt gtctgctccc ggcatccgct tacagacaag ctgtgaccgt    7140
ctccgggagc tgcatgtgtc agaggttttt accgtcatca ccgaaacgcg cgagacgaaa    7200
```

-continued

```
gggcctcgtg atacgcctat ttttataggt taatgtcatg ataataatgg tttcttagac    7260
gtcaggtggc acttttcggg gaaatgtgcg cggaacccct atttgtttat ttttctaaat    7320
acattcaaat atgtatccgc tcatgagaca ataaccctga taaatgcttc aataatattg    7380
aaaaaggaag agtatgagta ttcaacattt ccgtgtcgcc cttattccct ttttttgcggc   7440 attttgcctt cctgtttttg ctcacccaga aacgctggtg aaagtaaaag atgctgaaga    7500
tcagttgggt gcacgagtgg gttacatcga actggatctc aacagcggta agatccttga    7560
gagttttcgc cccgaagaac gttttccaat gatgagcact tttaaagttc tgctatgtgg    7620
cgcggtatta tcccgtattg acgccgggca agagcaactc ggtcgccgca tacactattc    7680
tcagaatgac ttggttgagt actcaccagt cacagaaaag catcttacgg atggcatgac    7740
agtaagagaa ttatgcagtg ctgccataac catgagtgat aacactgcgg ccaacttact    7800
tctgacaacg atcggaggac cgaaggagct aaccgctttt ttgcacaaca tgggggatca    7860
tgtaactcgc cttgatcgtt gggaaccgga gctgaatgaa gccataccaa acgacgagcg    7920
tgacaccacg atgcctgtag caatggcaac aacgttgcgc aaactattaa ctggcgaact    7980
acttactcta gcttcccggc aacaattaat agactggatg gaggcggata aagttgcagg    8040
accacttctg cgctcggccc ttccggctgg ctggtttatt gctgataaat ctggagccgg    8100
tgagcgtggg tctcgcggta tcattgcagc actggggcca gatggtaagc cctcccgtat    8160
cgtagttatc tacacgacgg ggagtcaggc aactatggat gaacgaaata gacagatcgc    8220
tgagataggt gcctcactga ttaagcattg gtaactgtca gaccaagttt actcatatat    8280
actttagatt gatttaaaac ttcattttta atttaaaagg atctaggtga agatcctttt    8340
tgataatctc atgaccaaaa tcccttaacg tgagttttcg ttccactgag cgtcagaccc    8400
cgtagaaaag atcaaaggat cttcttgaga tcctttttttt ctgcgcgtaa tctgctgctt    8460
gcaaacaaaa aaaccaccgc taccagcggt ggtttgtttg ccggatcaag agctaccaac    8520 tcttttttccg aaggtaactg gcttcagcag agcgcagata ccaaatactg tccttctagt    8580
gtagccgtag ttaggccacc acttcaagaa ctctgtagca ccgcctacat acctcgctct    8640
gctaatcctg ttaccagtgg ctgctgccag tggcgataag tcgtgtctta ccgggttgga    8700
ctcaagacga tagttaccgg ataaggcgca gcggtcgggc tgaacggggg gttcgtgcac    8760
acagcccagc ttggagcgaa cgacctacac cgaactgaga tacctacagc gtgagctatg    8820
agaaagcgcc acgcttcccg aagggagaaa ggcggacagg tatccggtaa gcggcagggt    8880
cggaacagga gagcgcacga gggagcttcc agggggaaac gcctggtatc tttatagtcc    8940
tgtcgggttt cgccacctct gacttgagcg tcgatttttg tgatgctcgt cagggggggcg   9000 gagcctatgg aaaaacgcca gcaacgcggc ctttttacgg ttcctggcct tttgctggcc    9060
ttttgctcac atgttctttc ctgcgttatc ccctgattct gtggataacc gtattaccgc    9120
ctttgagtga gctgataccg ctcgccgcag ccgaacgacc gagcgcagcg agtcagtgag    9180
cgaggaagcg gaagagcgcc caatacgcaa accgcctctc cccgcgcgtt ggccgattca    9240
ttaatgcag                                                            9249
```

<210> SEQ ID NO 2
<211> LENGTH: 3978
<212> TYPE: DNA
<213> ORGANISM: Artificial Sequence
<220> FEATURE:
<223> OTHER INFORMATION: Synthetic -continued

```
<400> SEQUENCE: 2
atggtgtggt gggaggaagt ggaggactgc tacgagagag aggacgtgca gaagaaaacc      60
ttcaccaagt gggtgaacgc ccagttcagc aagttcggca agcagcacat cgagaacctg     120
ttcagcgacc tgcaggatgg caggagactg ctggacctgc tggagggcct gaccggccag     180
aagctgccca aggagaaggg cagcaccaga gtgcacgccc tgaacaacgt gaacaaggcc     240
ctgagagtgc tgcagaacaa caacgtggac ctggtgaaca tcggcagcac cgacatcgtg     300
gacggcaacc acaagctgac cctgggcctg atctggaaca tcatcctgca ctggcaggtg     360
aagaacgtga tgaagaacat catggccggc ctgcagcaga ccaacagcga gaagatcctg     420
ctgagctggg tgaggcagag caccagaaac tacccccagg tgaacgtgat caacttcacc     480
acctcctgga gcgacggcct ggccctgaac gccctgatcc acagccacag acccgacctg     540
ttcgactgga acagcgtggt gtgtcagcag agcgccaccc agagactgga gcacgccttc     600
aacatcgcca gataccagct gggcatcgag aagctgctgg accccgagga cgtggacacc     660
acctaccccg acaagaaaag catcctcatg tacattacca gcctgttcca ggtgctgccc     720
cagcaggtgt ccatcgaggc catccaggaa gtggaaatgc tgcccaggcc ccccaaagtg     780
accaaggagg agcacttcca gctgcaccac cagatgcact acagccagca gatcacagtg     840
agcctggccc agggctatga gagaaccagc agccccaagc ccagattcaa gagctacgcc     900
tacacccagg ccgcctacgt gaccacctcc gaccccacca gaagcccctt ccccagccag     960
cacctggagg cccccgagga caagagcttc ggcagcagcc tgatggagag cgaagtgaac    1020
ctggacagat accagaccgc cctggaggaa gtgctgtcct ggctgctgag cgccgaggac    1080
accctgcagg cccagggcga gatcagcaac gacgtggaag tggtgaagga ccagttccac    1140
acccacgagg gctacatgat ggatctgacc gcccaccagg gcagagtggg caatatcctg    1200
cagctgggca gcaagctgat cggcaccggc aagctgagcg aggacgagga gaccgaagtg    1260
caggagcaga tgaacctgct gaacagcaga tgggagtgcc tgagagtggc cagcatggag    1320
aagcagagca acctgcacag agtgctgatg gacctgcaga accagaagct gaaggagctg    1380
aacgactggc tgaccaagac cgaggagcgg accagaaaga tggaggagga ccccctgggc    1440
cccgacctgg aggacctgaa gagacaggtg cagcagcaca aagtgctgca ggaggacctg    1500
gagcaggagc aggtgcgcgt gaacagcctg acccacatgg tggtggtcgt ggacgagagc    1560
agcggcgacc acgccacagc cgccctggaa gagcagctga aagtgctggg cgacagatgg    1620
gccaatattt gtaggtggac cgaggacaga tgggtgctgc tgcaggacca gcccgacctg    1680
gcccctggcc tgaccaccat cggcgccagc cccacccaga ccgtgaccct ggtgacccag    1740
cccgtggtga caaaggagac cgccatcagc aagctggaga tgcccagctc cctgatgctg    1800
gaagtgccca cccaccgcct gctccagcag ttccccctgg acctggagaa gttcctggcc    1860
tggctgaccg aggccgaaac caccgccaat gtgctccagg acgccactag aaaggagagg    1920
ctgctggagg acagcaaggg cgtgaaagag ctgatgaagc agtggcagga tctgcagggc    1980
gaaatcgagg cccacaccga cgtgtaccac aacctggacg agaacagcca gaagattctg    2040
aggagcctgg agggcagcga cgacgccgtc ctgctccaga ggaggctgga caacatgaac    2100
ttcaagtgga gcgagctgcg gaagaagagc ctgaacatcc ggagccacct ggaagccagc    2160
agcgaccagt ggaagagact gcacctgagc ctgcaggagc tgctggtgtg gctgcagctg    2220
aaggacgacg agctgagcag acaggccccc atcggcggcg acttccccgc cgtgcagaag    2280
cagaacgacg tgcaccgggc cttcaagagg gagctgaaaa ccaaggaacc cgtgatcatg    2340
```

-continued

```
agcaccctgg agacagtgcg gatcttcctg accgagcagc ccctggaggg actggagaag        2400
ctgtaccagg agcccagaga gctgccccc gaggagagag cccagaacgt gaccaggctg          2460
ctgagaaagc aggccgagga agtgaatacc gagtgggaga agctgaatct gcacagcgcc         2520
gactggcaga gaaagatcga cgagaccctg gagagactcc aggaactgca ggaagccacc        2580
gacgagctgg acctgaagct gagacaggcc gaagtgatca agggcagctg gcagcctgtg        2640
ggcgatctgc tgatcgactc cctgcaggat cacctggaga aagtgaaggc cctgcggggc        2700
gagatcgccc ccctgaagga gaatgtgagc cacgtgaacg acctggccag acagctgacc        2760
accctgggca tccagctgag cccctacaac ctgagcacac tggaggatct gaacacccgg        2820
tggaaactgc tgcaggtggc cgtggaggat agagtgaggc agctgcacga agcccacaga        2880
gacttcggcc ctgcctccca gcacttcctg agcaccagcg tgcagggccc ctgggagaga        2940
gccatctccc ccaacaaagt gccctactac atcaaccacg agacccagac cacctgctgg        3000
gaccacccta agatgaccga gctgtatcag agcctggccg acctgaacaa tgtgcggttc        3060
agcgcctaca gaaccgccat gaagctgcgg agactgcaga aggccctgtg cctggatctg        3120
ctgagcctga gcgccgcctg cgacgccctg gaccagcaca acctgaagca gaatgaccag        3180
cccatggaca tcctgcagat catcaactgc ctgaccacaa tctacgaccg gctggaacag        3240
gagcacaaca acctggtgaa tgtgcccctg tgcgtggaca tgtgcctgaa ttggctgctg        3300
aacgtgtacg acaccggcag gaccggcaga atccgcgtgc tgagcttcaa gaccggcatc        3360
atcagcctgt gcaaggccca cctggaggat aagtaccgct acctgttcaa gcaggtggcc        3420
agcagcaccg gcttctgcga tcagaggaga ctgggcctgc tgctgcacga tagcatccag        3480
atccctaggc agctgggcga agtggccagc tttggcggca gcaacatcga gccctctgtg        3540
aggagctgct tccagttcgc caacaacaag cccgagatcg aggccgccct gttcctggac        3600
tggatgaggc tggagcctca gagcatggtg tggctgcctg tgctgcacag agtggccgcc        3660
gccgagaccg ccaagcacca ggccaagtgc aatatctgca aggagtgccc catcatcggc        3720
ttccggtaca ggagcctgaa gcacttcaac tacgacatct gccagagctg ctttttcagc        3780
ggcagagtgg ccaagggcca caaaatgcac tacccatgg tggagtactg cacccccacc         3840
acctccggcg aggatgtgag agacttcgcc aaagtgctga agaataagtt ccggaccaag        3900
cggtactttg ccaagcaccc caggatgggc tacctgcccg tgcagaccgt gctggaaggc        3960
gacaacatgg agacctga                                                      3978
```

```
<210> SEQ ID NO 3
<211> LENGTH: 756
<212> TYPE: DNA
<213> ORGANISM: Artificial Sequence
<220> FEATURE:
<223> OTHER INFORMATION: Synthetic

<400> SEQUENCE: 3
```

```
atggtgtggt gggaggaagt ggaggactgc tacgagagag aggacgtgca gaagaaaacc         60
ttcaccaagt gggtgaacgc ccagttcagc aagttcggca agcagcacat cgagaacctg        120
ttcagcgacc tgcaggatgg caggagactg ctggacctgc tggagggcct gaccggccag        180
aagctgccca ggagaagggg cagcaccaga gtgcacgccc tgaacaacgt gaacaaggcc        240
ctgagagtgc tgcagaacaa caacgtggac ctggtgaaca tcggcagcac cgacatcgtg        300
gacggcaacc acaagctgac cctgggcctg atctggaaca tcatcctgca ctggcaggtg        360
```

-continued

```
aagaacgtga tgaagaacat catggccggc ctgcagcaga ccaacagcga gaagatcctg      420
ctgagctggg tgaggcagag caccagaaac tacccccagg tgaacgtgat caacttcacc      480
acctcctgga gcgacggcct ggccctgaac gccctgatcc acagccacag acccgacctg      540
ttcgactgga acagcgtggt gtgtcagcag agcgccaccc agagactgga gcacgccttc      600
aacatcgcca gataccagct gggcatcgag aagctgctgg accccgagga cgtggacacc      660
acctaccccg acaagaaaag catcctcatg tacattacca gcctgttcca ggtgctgccc      720
cagcaggtgt ccatcgaggc catccaggaa gtggaa                                756
```

<210> SEQ ID NO 4
<211> LENGTH: 225
<212> TYPE: DNA
<213> ORGANISM: Artificial Sequence
<220> FEATURE:
<223> OTHER INFORMATION: Synthetic

<400> SEQUENCE: 4

```
atgctgccca ggccccccaa agtgaccaag gaggagcact tccagctgca ccaccagatg      60
cactacagcc agcagatcac agtgagcctg gcccagggct atgagagaac cagcagcccc     120
aagcccagat tcaagagcta cgcctacacc caggccgcct acgtgaccac ctccgacccc     180
accagaagcc ccttccccag ccagcacctg gaggcccccg aggac                     225
```

<210> SEQ ID NO 5
<211> LENGTH: 333
<212> TYPE: DNA
<213> ORGANISM: Artificial Sequence
<220> FEATURE:
<223> OTHER INFORMATION: Synthetic

<400> SEQUENCE: 5

```
agcgaagtga acctggacag ataccagacc gccctggagg aagtgctgtc ctggctgctg      60
agcgccgagg acaccctgca ggcccagggc gagatcagca cgacgtgga agtggtgaag     120 gaccagttcc acacccacga gggctacatg atggatctga ccgcccacca gggcagagtg     180
ggcaatatcc tgcagctggg cagcaagctg atcggcaccg gcaagctgag cgaggacgag     240
gagaccgaag tgcaggagca gatgaacctg ctgaacagca gatgggagtg cctgagagtg     300
gccagcatgg agaagcagag caacctgcac aga                                  333
```

<210> SEQ ID NO 6
<211> LENGTH: 327
<212> TYPE: DNA
<213> ORGANISM: Artificial Sequence
<220> FEATURE:
<223> OTHER INFORMATION: Synthetic

<400> SEQUENCE: 6

```
gtgctgatgg acctgcagaa ccagaagctg aaggagctga cgactggct gaccaagacc       60 gaggagcgga ccagaaagat ggaggaggag cccctgggcc ccgacctgga ggacctgaag     120
agacaggtgc agcagcacaa agtgctgcag gaggacctgg agcaggagca ggtgcgcgtg     180
aacagcctga cccacatggt ggtggtcgtg gacgagagca gcggcgacca cgccacagcc     240
gccctggaag agcagctgaa agtgctgggc gacagatggg ccaatatttg taggtggacc     300
gaggacagat gggtgctgct gcaggac                                        327
```

<210> SEQ ID NO 7
<211> LENGTH: 141

```
<212> TYPE: DNA
<213> ORGANISM: Artificial Sequence
<220> FEATURE:
<223> OTHER INFORMATION: Synthetic

<400> SEQUENCE: 7
cagcccgacc tggcccctgg cctgaccacc atcggcgcca gccccaccca gaccgtgacc      60
ctggtgaccc agcccgtggt gacaaaggag accgccatca gcaagctgga gatgcccagc     120
tccctgatgc tggaagtgcc c                                               141

<210> SEQ ID NO 8
<211> LENGTH: 348
<212> TYPE: DNA
<213> ORGANISM: Artificial Sequence
<220> FEATURE:
<223> OTHER INFORMATION: Synthetic

<400> SEQUENCE: 8
acccaccgcc tgctccagca gttccccctg gacctggaga agttcctggc ctggctgacc      60
gaggccgaaa ccaccgccaa tgtgctccag gacgccacta gaaaggagag gctgctggag     120
gacagcaagg gcgtgaaaga gctgatgaag cagtggcagg atctgcaggg cgaaatcgag     180
gcccacaccg acgtgtacca caacctggac gagaacagcc agaagattct gaggagcctg     240
gagggcagcg acgacgccgt cctgctccag aggaggctgg acaacatgaa cttcaagtgg     300
agcgagctgc ggaagaagag cctgaacatc cggagccacc tggaagcc                  348

<210> SEQ ID NO 9
<211> LENGTH: 387
<212> TYPE: DNA
<213> ORGANISM: Artificial Sequence
<220> FEATURE:
<223> OTHER INFORMATION: Synthetic

<400> SEQUENCE: 9
agcagcgacc agtggaagag actgcacctg agcctgcagg agctgctggt gtggctgcag      60
ctgaaggacg acgagctgag cagacaggcc cccatcggcg gcgacttccc cgccgtgcag     120
aagcagaacg acgtgcaccg ggccttcaag agggagctga aaaccaagga acccgtgatc     180
atgagcaccc tggagacagt gcggatcttc ctgaccgagc agcccctgga gggactggag     240
aagctgtacc aggagcccag agagctgccc cccgaggaga gagcccagaa cgtgaccagg     300
ctgctgagaa agcaggccga ggaagtgaat accgagtggg agaagctgaa tctgcacagc     360
gccgactggc agagaaagat cgacgag                                         387

<210> SEQ ID NO 10
<211> LENGTH: 327
<212> TYPE: DNA
<213> ORGANISM: Artificial Sequence
<220> FEATURE:
<223> OTHER INFORMATION: Synthetic

<400> SEQUENCE: 10
accctggaga gactccagga actgcaggaa gccaccgacg agctggacct gaagctgaga      60
caggccgaag tgatcaaggg cagctggcag cctgtgggcg atctgctgat cgactccctg     120
caggatcacc tggagaaagt gaaggccctg cggggcgaga tcgcccccct gaaggagaat     180
gtgagccacg tgaacgacct ggccagacag ctgaccaccc tgggcatcca gctgagcccc     240
tacaacctga gcacactgga ggatctgaac acccggtgga aactgctgca ggtggccgtg     300
```

-continued

```
gaggatagag tgaggcagct gcacgaa                                     327

<210> SEQ ID NO 11
<211> LENGTH: 216
<212> TYPE: DNA
<213> ORGANISM: Artificial Sequence
<220> FEATURE:
<223> OTHER INFORMATION: Synthetic

<400> SEQUENCE: 11
gcccacagag acttcggccc tgcctcccag cacttcctga gcaccagcgt gcagggcccc      60
tgggagagag ccatctcccc caacaaagtg ccctactaca tcaaccacga gacccagacc     120
acctgctggg accaccctaa gatgaccgag ctgtatcaga gcctggccga cctgaacaat     180
gtgcggttca gcgcctacag aaccgccatg aagctg                              216

<210> SEQ ID NO 12
<211> LENGTH: 888
<212> TYPE: DNA
<213> ORGANISM: Artificial Sequence
<220> FEATURE:
<223> OTHER INFORMATION: Synthetic

<400> SEQUENCE: 12
cggagactgc agaaggccct gtgcctggat ctgctgagcc tgagcgccgc ctgcgacgcc      60
ctggaccagc acaacctgaa gcagaatgac cagcccatgg acatcctgca gatcatcaac     120
tgcctgacca caatctacga ccggctggaa caggagcaca caacctggt gaatgtgccc      180 ctgtgcgtgg acatgtgcct gaattggctg ctgaacgtgt acgacaccgg caggaccggc     240
agaatccgcg tgctgagctt caagaccggc atcatcagcc tgtgcaaggc ccacctggag     300
gataagtacc gctacctgtt caagcaggtg gccagcagca ccggcttctg cgatcagagg     360
agactgggcc tgctgctgca cgatagcatc cagatcccta ggcagctggg cgaagtggcc     420
agctttggcg gcagcaacat cgagccctct gtgaggagct gcttccagtt cgccaacaac     480
aagcccgaga tcgaggccgc cctgttcctg gactggatga ggctggagcc tcagagcatg     540
gtgtggctgc ctgtgctgca cagagtggcc gccgccgaga ccgccaagca ccaggccaag     600
tgcaatatct gcaaggagtg ccccatcatc ggcttccggt acaggagcct gaagcacttc     660
aactacgaca tctgccagag ctgctttttc agcggcagag tggccaaggg ccacaaaatg     720
cactacccca tggtggagta ctgcacccccc accacctccg gcgaggatgt gagagacttc     780
gccaaagtgc tgaagaataa gttccggacc aagcggtact ttgccaagca ccccaggatg     840
ggctacctgc ccgtgcagac cgtgctggaa ggcgacaaca tggagacc                  888

<210> SEQ ID NO 13
<211> LENGTH: 3
<212> TYPE: DNA
<213> ORGANISM: Artificial Sequence
<220> FEATURE:
<223> OTHER INFORMATION: Synthetic

<400> SEQUENCE: 13 tga                                                                 3

<210> SEQ ID NO 14
<211> LENGTH: 216
<212> TYPE: DNA
<213> ORGANISM: Artificial Sequence
<220> FEATURE:
<223> OTHER INFORMATION: Synthetic
```

-continued

<400> SEQUENCE: 14

```
ccactacggg tctaggctgc ccatgtaagg aggcaaggcc tggggacacc cgagatgcct       60
ggttataatt aaccccaaca cctgctgccc cccccccccc aacacctgct gcctgagcct      120
gagcggttac cccaccccgg tgcctgggtc ttaggctctg tacaccatgg aggagaagct      180
cgctctaaaa ataaccctgt ccctggtgga tcccct                                216
```

```
<210> SEQ ID NO 15
<211> LENGTH: 317
<212> TYPE: DNA
<213> ORGANISM: Artificial Sequence
<220> FEATURE:
<223> OTHER INFORMATION: Synthetic
```

<400> SEQUENCE: 15

```
gcatgcggcc gtccgccctc ggcaccattc ctcacgacac cgaaatatgg cgacgggtga       60
ggaatggtgg ggagttattt ttagagcggt gaggaatggt gggcaggcag caggtgttgg      120
gggagttatt tttagagcgg ggagttattt ttagagcggt gaggaatggt ggacaccgaa      180
atatggcgac gggtgaggaa tggtgccgtc gccatatttg ggtgtcccgt ccgccctcgg      240
ccggggccgc attcctgggg gccgggcggt gctcccgccc gcctcgataa aaggctccgg      300
ggccggcggc ggcccac                                                     317
```

```
<210> SEQ ID NO 16
<211> LENGTH: 6
<212> TYPE: DNA
<213> ORGANISM: Artificial Sequence
<220> FEATURE:
<223> OTHER INFORMATION: Synthetic
```

<400> SEQUENCE: 16

```
gccacc                                                                   6
```

```
<210> SEQ ID NO 17
<211> LENGTH: 51
<212> TYPE: DNA
<213> ORGANISM: Artificial Sequence
<220> FEATURE:
<223> OTHER INFORMATION: Synthetic
```

<400> SEQUENCE: 17

```
tgtgtccatt gtctcactcc tcgaggagtg agacaatgga cacatttttt t                51
```

```
<210> SEQ ID NO 18
<211> LENGTH: 241
<212> TYPE: DNA
<213> ORGANISM: Artificial Sequence
<220> FEATURE:
<223> OTHER INFORMATION: Synthetic
```

<400> SEQUENCE: 18

```
gagggcctat ttcccatgat tccttcatat ttgcatatac gatacaaggc tgttagagag       60
ataattagaa ttaatttgac tgtaaacaca aagatattag tacaaaatac gtgacgtaga      120
aagtaataat ttcttgggta gtttgcagtt ttaaaattat gttttaaaat ggactatcat      180
atgcttaccg taacttgaaa gtatttcgat ttcttggctt tatatatctt gtggaaagga      240
c                                                                      241
```

```
<210> SEQ ID NO 19
```

```
<211> LENGTH: 145
<212> TYPE: DNA
<213> ORGANISM: Artificial Sequence
<220> FEATURE:
<223> OTHER INFORMATION: Synthetic

<400> SEQUENCE: 19
ttggccactc cctctctgcg cgctcgctcg ctcactgagg ccgggcgacc aaaggtcgcc        60
cgacgcccgg gctttgcccg ggcggcctca gtgagcgagc gagcgcgcag agagggagtg       120
gccaactcca tcactagggg ttcct                                            145

<210> SEQ ID NO 20
<211> LENGTH: 145
<212> TYPE: DNA
<213> ORGANISM: Artificial Sequence
<220> FEATURE:
<223> OTHER INFORMATION: Synthetic

<400> SEQUENCE: 20
aggaacccct agtgatggag ttggccactc cctctctgcg cgctcgctcg ctcactgagg        60
ccgcccgggc aaagcccggg cgtcgggcga cctttggtcg cccggcctca gtgagcgagc       120
gagcgcgcag agagggagtg gccaa                                            145

<210> SEQ ID NO 21
<211> LENGTH: 60
<212> TYPE: DNA
<213> ORGANISM: Artificial Sequence
<220> FEATURE:
<223> OTHER INFORMATION: Synthetic

<400> SEQUENCE: 21
tcgaggccta ataaagagct cagatgcatc gatcagagtg tgttggtttt ttgtgtgaga        60

<210> SEQ ID NO 22
<211> LENGTH: 51
<212> TYPE: DNA
<213> ORGANISM: Artificial Sequence
<220> FEATURE:
<223> OTHER INFORMATION: Synthetic

<400> SEQUENCE: 22
agtccctgtc tgcacctgtc tcgagacagg tgcagacagg gacttttttt t                51

<210> SEQ ID NO 23
<211> LENGTH: 9249
<212> TYPE: DNA
<213> ORGANISM: Artificial Sequence
<220> FEATURE:
<223> OTHER INFORMATION: Synthetic

<400> SEQUENCE: 23
aattcccatc atcaataata taccttattt tggattgaag ccaatatgat aatgaggggg        60
tggagtttgt gacgtggcgc ggggcgtggg aacggggcgg gtgacgtagt agtctctaga       120
ggtccccagc gaccttgacg ggcatctgcc cggcatttct gacagctttg tgaactgggt       180
ggccgagaag gaatgggagt tgccgccaga ttctgacatg gatctgaatc tgattgagca       240
ggcacccctg accgtggccg agaagctgca tcgctggcgt aatagcgaag aggcccgcac       300
cgatcgccct tcccaacagt tgcgcagcct gaatggcgaa tggaattcca gacgattgag       360
cgtcaaaatg taggtatttc catgagcgtt tttcctgttg caatggctgg cggtaatatt       420
gttctggata ttaccagcaa ggccgatagt ttgagttctt ctactcaggc aagtgatgtt       480
```

-continued

```
attactaatc aaagaagtat tgcgacaacg gttaatttgc gtgatggaca gactctttta    540
ctcggtggcc tcactgatta taaaaacact tctcaggatt ctggcgtacc gttcctgtct    600
aaaatccctt taatcggcct cctgtttagc tcccgctctg attctaacga ggaaagcacg    660
ttatacgtgc tcgtcaaagc aaccatagta cgcgccctgt agcggcgcat taagcgcggc    720
gggtgtggtg gttacgcgca gcgtgaccgc tacacttgcc agcgccctag cgcccgctcc    780
tttcgctttc ttcccttcct ttctcgccac gttcgccggc tttccccgtc aagctctaaa    840 tcggggggctc cctttagggt tccgatttag tgctttacgg cacctcgacc ccaaaaaact    900
tgattagggt gatggttcac gtagtgggcc atcgccctga tagacggttt ttcgcccttt    960
gacgttggag tccacgttct ttaatagtgg actcttgttc caaactggaa caacactcaa   1020
ccctatctcg gtctattctt ttgatttata agggattttg ccgatttcgg cctattggtt   1080
aaaaaatgag ctgatttaac aaaaatttaa cgcgaatttt aacaaaatat taacgtttac   1140
aatttaaata tttgcttata caatcttcct gttttttgggg cttttctgat tatcaaccgg   1200
ggtacatatg attgacatgc tagtttttacg attaccgttc atcgcctgca gggggggggg   1260
ggggggggtt ggccactccc tctctgcgcg ctcgctcgct cactgaggcc gggcgaccaa   1320
aggtcgcccg acgcccgggc tttgcccggg cggcctcagt gagcgagcga gcgcgcagag   1380
agggagtggc caactccatc actaggggtt cctagatctg aattcgagct tgccacgcat   1440
gcgggcagga agagggccta tttcccatga ttccttcata tttgcatata cgatacaagg   1500
ctgttagaga gataattaga attaatttga ctgtaaacac aaagatatta gtacaaaata   1560
cgtgacgtag aaagtaataa tttcttgggt agtttgcagt tttaaaatta tgttttaaaa   1620
tggactatca tatgcttacc gtaacttgaa agtatttcga tttcttggct ttatatatct   1680
tgtggaaagg acgaggatcc agtccctgtc tgcacctgtc tcgagacagg tgcagacagg   1740 gactttttttt tgaattccac tacgggtcta ggctgcccat gtaaggaggc aaggcctggg   1800
gacacccgag atgcctggtt ataattaacc ccaacacctg ctgcccccccc cccccaaca   1860 cctgctgcct gagcctgagc ggttaccccca ccccggtgcc tgggtcttag gctctgtaca   1920
ccatggagga gaagctcgct ctaaaaataa ccctgtccct ggtggatccc ctgcatgcgg   1980
ccgtccgccc tcggcaccat tcctcacgac accgaaatat ggcgacgggt gaggaatggt   2040
ggggagttat ttttagagcg gtgaggaatg gtgggcaggc agcaggtgtt gggggagtta   2100 ttttttagagc ggggagttat ttttagagcg gtgaggaatg gtggacaccg aaatatggcg   2160
acgggtgagg aatggtgccg tcgccatatt tgggtgtccc gtccgccctc ggccggggcc   2220
gcattcctgg gggccgggcg gtgctcccgc ccgcctcgat aaaaggctcc ggggccggcg   2280
gcggcccact cgagacgttg taaaacgacg gccagtgagc gcgcgtaata cgactcacta   2340
tagggcgaat tgggtaccgc caccatggtg tggtgggagg aagtggagga ctgctacgag   2400
agagaggacg tgcagaagaa aaccttcacc aagtgggtga cgcccagtt cagcaagttc   2460 ggcaagcagc acatcgagaa cctgttcagc gacctgcagg atggcaggag actgctggac   2520
ctgctggagg gcctgaccgg ccagaagctg cccaaggaga agggcagcac cagagtgcac   2580
gccctgaaca acgtgaacaa ggccctgaga gtgctgcaga acaacaacgt ggacctggtg   2640
aacatcggca gcaccgacat cgtggacggc aaccacaagc tgaccctggg cctgatctgg   2700
aacatcatcc tgcactggca ggtgaagaac gtgatgaaga acatcatggc cggcctgcag   2760
cagaccaaca gcgagaagat cctgctgagc tgggtgaggc agagcaccag aaactacccc   2820
```

-continued

```
caggtgaacg tgatcaactt caccacctcc tggagcgacg gcctggccct gaacgccctg    2880
atccacagcc acagacccga cctgttcgac tggaacagcg tggtgtgtca gcagagcgcc    2940
acccagagac tggagcacgc cttcaacatc gccagatacc agctgggcat cgagaagctg    3000
ctggaccccg aggacgtgga caccacctac cccgacaaga aaagcatcct catgtacatt    3060
accagcctgt tccaggtgct gccccagcag gtgtccatcg aggccatcca ggaagtggaa    3120
atgctgccca ggccccccaa agtgaccaag gaggagcact tccagctgca ccaccagatg    3180
cactacagcc agcagatcac agtgagcctg gcccagggct atgagagaac cagcagcccc    3240
aagcccagat tcaagagcta cgcctacacc caggccgcct acgtgaccac ctccgacccc    3300
accagaagcc ccttccccag ccagcacctg gaggcccccg aggacaagag cttcggcagc    3360
agcctgatgg agagcgaagt gaacctggac agataccaga ccgccctgga ggaagtgctg    3420
tcctggctgc tgagcgccga ggacaccctg caggcccagg gcgagatcag caacgacgtg    3480
gaagtggtga aggaccagtt ccacacccac gagggctaca tgatggatct gaccgcccac    3540
cagggcagag tgggcaatat cctgcagctg ggcagcaagc tgatcggcac cggcaagctg    3600
agcgaggacg aggagaccga agtgcaggag cagatgaacc tgctgaacag cagatgggag    3660
tgcctgagag tggccagcat ggagaagcag agcaacctgc acagagtgct gatggacctg    3720
cagaaccaga agctgaagga gctgaacgac tggctgacca agaccgagga gcggaccaga    3780
aagatggagg aggagcccct gggccccgac ctggaggacc tgaagagaca ggtgcagcag    3840
cacaaagtgc tgcaggagga cctggagcag gagcaggtgc gcgtgaacag cctgacccac    3900
atggtggtgg tcgtggacga gagcagcggc gaccacgcca cagccgccct ggaagagcag    3960
ctgaaagtgc tgggcgacag atgggccaat atttgtaggt ggaccgagga cagatgggtg    4020
ctgctgcagg accagcccga cctggcccct ggcctgacca ccatcggcgc cagccccacc    4080
cagaccgtga ccctggtgac ccagcccgtg gtgacaaagg agaccgccat cagcaagctg    4140
gagatgccca gctccctgat gctggaagtg cccacccacc gcctgctcca gcagttcccc    4200
ctggacctgg agaagttcct ggcctggctg accgaggccg aaaccaccgc caatgtgctc    4260
caggacgcca ctagaaagga gaggctgctg gaggacagca agggcgtgaa agagctgatg    4320
aagcagtggc aggatctgca gggcgaaatc gaggcccaca ccgacgtgta ccacaacctg    4380
gacgagaaca gccagaagat tctgaggagc ctggagggca gcgacgacgc cgtcctgctc    4440
cagaggaggc tggacaacat gaacttcaag tggagcgagc tgcggaagaa gagcctgaac    4500
atccggagcc acctggaagc cagcagcgac cagtggaaga gactgcacct gagcctgcag    4560
gagctgctgg tgtggctgca gctgaaggac gacgagctga gcagacaggc ccccatcggc    4620
ggcgacttcc ccgccgtgca gaagcagaac gacgtgcacc gggccttcaa gagggagctg    4680
aaaaccaagg aacccgtgat catgagcacc ctggagacag tgcggatctt cctgaccgag    4740
cagcccctgg agggactgga gaagctgtac caggagccca gagagctgcc ccccgaggag    4800
agagcccaga acgtgaccag gctgctgaga aagcaggccg aggaagtgaa taccgagtgg    4860
gagaagctga atctgcacag cgccgactgg cagagaaaga tcgacgagac cctggagaga    4920
ctccaggaac tgcaggaagc caccgacgag ctggacctga gctgagaca ggccgaagtg    4980 atcaagggca gctggcagcc tgtgggcgat ctgctgatcg actccctgca ggatcacctg    5040
gagaaagtga ggcccctgcg gggcgagatc gcccccctga aggagaatgt gagccacgtg    5100
aacgacctgg ccagacagct gaccacccctg ggcatccagc tgagcccta caacctgagc    5160 acactggagg atctgaacac ccggtggaaa ctgctgcagg tggccgtgga ggatagagtg    5220
```

-continued

```
aggcagctgc acgaagccca cagagacttc ggccctgcct cccagcactt cctgagcacc    5280
agcgtgcagg gcccctggga gagagccatc tcccccaaca aagtgcccta ctacatcaac    5340
cacgagaccc agaccacctg ctgggaccac cctaagatga ccgagctgta tcagagcctg    5400
gccgacctga acaatgtgcg gttcagcgcc tacagaaccg ccatgaagct gcggagactg    5460
cagaaggccc tgtgcctgga tctgctgagc ctgagcgccg cctgcgacgc cctggaccag    5520
cacaacctga agcagaatga ccagcccatg gacatcctgc agatcatcaa ctgcctgacc    5580
acaatctacg accggctgga acaggagcac aacaacctgg tgaatgtgcc cctgtgcgtg    5640
gacatgtgcc tgaattggct gctgaacgtg tacgacaccg gcaggaccgg cagaatccgc    5700
gtgctgagct tcaagaccgg catcatcagc ctgtgcaagg cccacctgga ggataagtac    5760
cgctacctgt tcaagcaggt ggccagcagc accggcttct gcgatcagag gagactgggc    5820
ctgctgctgc acgatagcat ccagatccct aggcagctgg gcgaagtggc cagctttggc    5880
ggcagcaaca tcgagccctc tgtgaggagc tgcttccagt tcgccaacaa caagcccgag    5940
atcgaggccg ccctgttcct ggactggatg aggctggagc ctcagagcat ggtgtggctg    6000
cctgtgctgc acagagtggc cgccgccgag accgccaagc accaggccaa gtgcaatatc    6060
tgcaaggagt gccccatcat cggcttccgg tacaggagcc tgaagcactt caactacgac    6120
atctgccaga gctgcttttt cagcggcaga gtggccaagg gccacaaaat gcactacccc    6180
atggtggagt actgcacccc caccacctcc ggcgaggatg tgagagactt cgccaaagtg    6240
ctgaagaata agttccggac caagcggtac tttgccaagc accccaggat gggctacctg    6300
cccgtgcaga ccgtgctgga aggcgacaac atggagacct gatgaggagc tcgaggccta    6360
ataaagagct cagatgcatc gatcagagtg tgttggtttt ttgtgtgaga tctaggaacc    6420
cctagtgatg gagttggcca ctccctctct gcgcgctcgc tcgctcactg aggccgcccg    6480
ggcaaagccc gggcgtcggg cgacctttgg tcgcccggcc tcagtgagcg agcgagcgcg    6540
cagagaggga gtggccaacc ccccccccc cccccctgca ggcgattctc ttgtttgctc    6600
cagactctca ggcaatgacc tgatagcctt gtagagacc tctcaaaaat agctaccctc    6660
tccggcatga atttatcagc tagaacggtt gaatatcata ttgatggtga tttgactgtc    6720
tccggccttt ctcacccgtt tgaatcttta cctacacatt actcaggcat tgcatttaaa    6780
atatatgagg gttctaaaaa tttttatcct tgcgttgaaa taaaggcttc tcccgcaaaa    6840
gtattacagg gtcataatgt ttttggtaca accgatttag ctttatgctc tgaggcttta    6900
ttgcttaatt ttgctaattc tttgccttgc ctgtatgatt tattggatgt tggaattcct    6960
gatgcggtat tttctcctta cgcatctgtg cggtatttca caccgcatat ggtgcactct    7020
cagtacaatc tgctctgatg ccgcatagtt aagccagccc cgacacccgc caacacccgc    7080
tgacgcgccc tgacgggctt gtctgctccc ggcatccgct tacagacaag ctgtgaccgt    7140
ctccgggagc tgcatgtgtc agaggttttc accgtcatca ccgaaacgcg cgagacgaaa    7200
gggcctcgtg atacgcctat ttttataggt taatgtcatg ataataatgg tttcttagac    7260
gtcaggtggc acttttcggg gaaatgtgcg cggaacccct atttgtttat ttttctaaat    7320
acattcaaat atgtatccgc tcatgagaca ataaccctga taaatgcttc aataatattg    7380
aaaaaggaag agtatgagta ttcaacattt ccgtgtcgcc cttattccct tttttgcggc    7440
attttgcctt cctgtttttg ctcacccaga aacgctggtg aaagtaaaag atgctgaaga    7500
tcagttgggt gcacgagtgg gttacatcga actggatctc aacagcggta agatccttga    7560
```

-continued

```
gagttttcgc cccgaagaac gttttccaat gatgagcact tttaaagttc tgctatgtgg      7620
cgcggtatta tcccgtattg acgccgggca agagcaactc ggtcgccgca tacactattc      7680
tcagaatgac ttggttgagt actcaccagt cacagaaaag catcttacgg atggcatgac      7740
agtaagagaa ttatgcagtg ctgccataac catgagtgat aacactgcgg ccaacttact      7800
tctgacaacg atcggaggac cgaaggagct aaccgctttt ttgcacaaca tgggggatca      7860
tgtaactcgc cttgatcgtt gggaaccgga gctgaatgaa gccataccaa acgacgagcg      7920
tgacaccacg atgcctgtag caatggcaac aacgttgcgc aaactattaa ctggcgaact      7980
acttactcta gcttcccggc aacaattaat agactggatg gaggcggata aagttgcagg      8040
accacttctg cgctcggccc ttccggctgg ctggtttatt gctgataaat ctggagccgg      8100
tgagcgtggg tctcgcggta tcattgcagc actggggcca gatggtaagc cctcccgtat      8160
cgtagttatc tacacgacgg ggagtcaggc aactatggat gaacgaaata gacagatcgc      8220
tgagataggt gcctcactga ttaagcattg gtaactgtca gaccaagttt actcatatat      8280
actttagatt gatttaaaac ttcattttta atttaaaagg atctaggtga agatcctttt      8340
tgataatctc atgaccaaaa tcccttaacg tgagttttcg ttccactgag cgtcagaccc      8400
cgtagaaaag atcaaaggat cttcttgaga tccttttttt ctgcgcgtaa tctgctgctt      8460
gcaaacaaaa aaaccaccgc taccagcggt ggtttgtttg ccggatcaag agctaccaac      8520 tcttttccg aaggtaactg gcttcagcag agcgcagata ccaaatactg tccttctagt       8580
gtagccgtag ttaggccacc acttcaagaa ctctgtagca ccgcctacat acctcgctct      8640
gctaatcctg ttaccagtgg ctgctgccag tggcgataag tcgtgtctta ccgggttgga      8700
ctcaagacga tagttaccgg ataaggcgca gcggtcgggc tgaacggggg gttcgtgcac      8760
acagcccagc ttggagcgaa cgacctacac cgaactgaga tacctacagc gtgagctatg      8820
agaaagcgcc acgcttcccg aagggagaaa ggcggacagg tatccggtaa gcggcagggt      8880
cggaacagga gagcgcacga gggagcttcc aggggggaaac gcctggtatc tttatagtcc      8940
tgtcgggttt cgccacctct gacttgagcg tcgatttttg tgatgctcgt caggggggcg      9000
gagcctatgg aaaaacgcca gcaacgcggc ctttttacgg ttcctggcct tttgctggcc      9060
ttttgctcac atgttctttc ctgcgttatc ccctgattct gtggataacc gtattaccgc      9120
ctttgagtga gctgataccg ctcgccgcag ccgaacgacc gagcgcagcg agtcagtgag      9180
cgaggaagcg gaagagcgcc caatacgcaa accgcctctc cccgcgcgtt ggccgattca      9240
ttaatgcag                                                             9249
```

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24

```
gattgaggag aaacgtaaat t                                                21
```

<210> SEQ ID NO 25
<211> LENGTH: 9108
<212> TYPE: DNA
<213> ORGANISM: Artificial Sequence
<220> FEATURE:
<223> OTHER INFORMATION: Synthetic

<400> SEQUENCE: 25

```
aattcccatc atcaataata taccttattt tggattgaag ccaatatgat aatgaggggg      60
tggagtttgt gacgtggcgc ggggcgtggg aacggggcgg gtgacgtagt agtctctaga     120
ggtccccagc gaccttgacg ggcatctgcc cggcatttct gacagctttg tgaactgggt     180
ggccgagaag gaatgggagt tgccgccaga ttctgacatg gatctgaatc tgattgagca     240
ggcacccctg accgtggccg agaagctgca tcgctggcgt aatagcgaag aggcccgcac     300
cgatcgccct tcccaacagt tgcgcagcct gaatggcgaa tggaattcca gacgattgag     360
cgtcaaaatg taggtatttc catgagcgtt tttcctgttg caatggctgg cggtaatatt     420
gttctggata ttaccagcaa ggccgatagt ttgagttctt ctactcaggc aagtgatgtt     480
attactaatc aaagaagtat tgcgacaacg gttaatttgc gtgatggaca gactctttta     540
ctcggtggcc tcactgatta taaaaacact tctcaggatt ctggcgtacc gttcctgtct     600
aaaatccctt taatcggcct cctgtttagc tcccgctctg attctaacga ggaaagcacg     660
ttatacgtgc tcgtcaaagc aaccatagta cgcgccctgt agcggcgcat taagcgcggc     720
gggtgtggtg gttacgcgca gcgtgaccgc tacacttgcc agcgccctag cgcccgctcc     780
tttcgctttc ttcccttcct ttctcgccac gttcgccggc tttccccgtc aagctctaaa     840 tcggggctc cctttagggt tccgatttag tgctttacgg cacctcgacc ccaaaaaact     900
tgattagggt gatggttcac gtagtgggcc atcgccctga tagacggttt ttcgcccttt     960
gacgttggag tccacgttct ttaatagtgg actcttgttc caaactggaa caacactcaa    1020
ccctatctcg gtctattctt ttgatttata agggattttg ccgatttcgg cctattggtt    1080
aaaaaatgag ctgatttaac aaaaatttaa cgcgaatttt aacaaaatat taacgtttac    1140
aatttaaata tttgcttata caatcttcct gttttgggg cttttctgat tatcaaccgg    1200
ggtacatatg attgacatgc tagttttacg attaccgttc atcgcctgca ggggggggg    1260 ggggggggtt ggccactccc tctctgcgcg ctcgctcgct cactgaggcc gggcgaccaa    1320
aggtcgcccg acgcccgggc tttgcccggg cggcctcagt gagcgagcga gcgcgcagag    1380
agggagtggc caactccatc actaggggtt cctagatctg aattcgagct tgccacgcat    1440
gcgggcagga agagggccta tttcccatga ttccttcata tttgcatata cgatacaagg    1500
ctgttagaga gataattaga attaatttga ctgtaaacac aaagatatta gtacaaaata    1560
cgtgacgtag aaagtaataa tttcttgggt agtttgcagt tttaaaatta tgttttaaaa    1620
tggactatca tatgcttacc gtaacttgaa agtatttcga tttcttggct ttatatatct    1680
tgtggaaagg acgaggatcc tgtgtccatt gtctcactcc tcgaggagtg agacaatgga    1740
cacatttttt tgaattccac tacgggtcta ggctgcccat gtaaggaggc aaggcctggg    1800
gacacccgag atgcctggtt ataattaacc ccaacacctg ctgcccccc ccccccaaca    1860 cctgctgcct gagcctgagc ggttacccca ccccggtgcc tgggtcttag gctctgtaca    1920
ccatggagga gaagctcgct ctaaaaataa ccctgtccct ggtggatccc ctgcatgcgg    1980
ccgtccgccc tcggcaccat tcctcacgac accgaaatat ggcgacgggt gaggaatggt    2040
ggggagttat tttttagagcg gtgaggaatg gtgggcaggc agcaggtgtt ggggagtta    2100 tttttagagc ggggagttat tttttagagcg gtgaggaatg gtggacaccg aaatatggcg    2160
acgggtgagg aatggtgccg tcgccatatt tgggtgtccc gtccgccctc ggccggggcc    2220
gcattcctgg gggccgggcg gtgctcccgc ccgcctcgat aaaaggctcc ggggccggcg    2280
gcggcccact cgagacgttg taaaacgacg gccagtgagc gcgcgtaata cgactcacta    2340
```

-continued

```
tagggcgaat tgggtaccgc caccatggtg tggtgggagg aagtggagga ctgctacgag    2400
agagaggacg tgcagaagaa aaccttcacc aagtgggtga acgcccagtt cagcaagttc    2460
ggcaagcagc acatcgagaa cctgttcagc gacctgcagg atggcaggag actgctggac    2520
ctgctggagg gcctgaccgg ccagaagctg cccaaggaga agggcagcac cagagtgcac    2580
gccctgaaca acgtgaacaa ggccctgaga gtgctgcaga acaacaacgt ggacctggtg    2640
aacatcggca gcaccgacat cgtggacggc aaccacaagc tgaccctggg cctgatctgg    2700
aacatcatcc tgcactggca ggtgaagaac gtgatgaaga acatcatggc cggcctgcag    2760
cagaccaaca gcgagaagat cctgctgagc tgggtgaggc agagcaccag aaactacccc    2820
caggtgaacg tgatcaactt caccacctcc tggagcgacg gcctggccct gaacgccctg    2880
atccacagcc acagacccga cctgttcgac tggaacagcg tggtgtgtca gcagagcgcc    2940
acccagagac tggagcacgc cttcaacatc gccagatacc agctgggcat cgagaagctg    3000
ctggaccccg aggacgtgga caccacctac cccgacaaga aaagcatcct catgtacatt    3060
accagcctgt tccaggtgct gccccagcag gtgtccatcg aggccatcca ggaagtggaa    3120
atgctgccca ggccccccaa agtgaccaag gaggagcact tccagctgca ccaccagatg    3180
cactacagcc agcagatcac agtgagcctg gcccagggct atgagagaac cagcagcccc    3240
aagcccagat tcaagagcta cgcctacacc caggccgcct acgtgaccac ctccgacccc    3300
accagaagcc ccttcccccag ccagcacctg gaggcccccg aggacaagag cttcggcagc    3360
agcctgatgg agagcgaagt gaacctggac agataccaga ccgccctgga ggaagtgctg    3420
tcctggctgc tgagcgccga ggacaccctg caggcccagg cgagatcag caacgacgtg    3480 gaagtggtga aggaccagtt ccacacccac gagggctaca tgatggatct gaccgcccac    3540
cagggcagag tggcaatat cctgcagctg ggcagcaagc tgatcggcac cggcaagctg    3600
agcgaggacg aggagaccga agtgcaggag cagatgaacc tgctgaacag cagatgggag    3660
tgcctgagag tggccagcat ggagaagcag agcaacctgc acagagtgct gatggacctg    3720
cagaaccaga agctgaagga gctgaacgac tggctgacca agaccgagga gcggaccaga    3780
aagatggagg aggagcccct gggcccccgac ctggaggacc tgaagagaca ggtgcagcag    3840
cacaaagtgc tgcaggagga cctggagcag gagcaggtgc gcgtgaacag cctgacccac    3900
atggtggtgg tcgtggacga gagcagcggc gaccacgcca cagccgccct ggaagagcag    3960
ctgaaagtgc tgggcgacag atgggccaat atttgtaggt ggaccgagga cagatgggtg    4020
ctgctgcagg acacccaccg cctgctccag cagttccccc tggacctgga gaagttcctg    4080
gcctggctga ccgaggccga aaccaccgcc aatgtgctcc aggacgccac tagaaaggag    4140
aggctgctgg aggacagcaa gggcgtgaaa gagctgatga agcagtggca ggatctgcag    4200
ggcgaaatcg aggcccacac cgacgtgtac cacaacctgg acgagaacag ccagaagatt    4260
ctgaggagcc tggagggcag cgacgacgcc gtcctgctcc agaggaggct ggacaacatg    4320
aacttcaagt ggagcgagct gcggaagaag agcctgaaca tccggagcca cctggaagcc    4380
agcagcgacc agtggaagag actgcacctg agcctgcagg agctgctggt gtggctgcag    4440
ctgaaggacg acgagctgag cagacaggcc cccatcggcg cgacttcc cgccgtgcag    4500 aagcagaacg acgtgcaccg ggccttcaag agggagctga aaaccaagga acccgtgatc    4560
atgagcaccc tggagacagt gcggatcttc ctgaccgagc agccctgga gggactggag    4620 aagctgtacc aggagcccag agagctgccc cccgaggaga gagcccagaa cgtgaccagg    4680
ctgctgagaa agcaggccga ggaagtgaat accgagtggg agaagctgaa tctgcacagc    4740
```

-continued

```
gccgactggc agagaaagat cgacgagacc ctggagagac tccaggaact gcaggaagcc    4800
accgacgagc tggacctgaa gctgagacag gccgaagtga tcaagggcag ctggcagcct    4860
gtgggcgatc tgctgatcga ctccctgcag gatcacctgg agaaagtgaa ggccctgcgg    4920
ggcgagatcg cccccctgaa ggagaatgtg agccacgtga cgacctggc cagacagctg      4980 accaccctgg gcatccagct gagcccctac aacctgagca cactggagga tctgaacacc    5040
cggtggaaac tgctgcaggt ggccgtggag gatagagtga ggcagctgca cgaagcccac    5100
agagacttcg gccctgcctc ccagcacttc ctgagcacca gcgtgcaggg ccctgggag      5160 agagccatct cccccaacaa agtgccctac tacatcaacc acgagaccca gaccacctgc    5220
tgggaccacc ctaagatgac cgagctgtat cagagcctgg ccgacctgaa caatgtgcgg    5280
ttcagcgcct acagaaccgc catgaagctg cggagactgc agaaggccct gtgcctggat    5340
ctgctgagcc tgagcgccgc ctgcgacgcc ctggaccagc acaacctgaa gcagaatgac    5400
cagcccatgg acatcctgca gatcatcaac tgcctgacca caatctacga ccggctggaa    5460
caggagcaca acaacctggt gaatgtgccc ctgtgcgtgg acatgtgcct gaattggctg    5520
ctgaacgtgt acgacaccgg caggaccggc agaatccgcg tgctgagctt caagaccggc    5580
atcatcagcc tgtgcaaggc ccacctggag gataagtacc gctacctgtt caagcaggtg    5640
gccagcagca ccggcttctg cgatcagagg agactgggcc tgctgctgca cgatagcatc    5700
cagatcccta ggcagctggg cgaagtggcc agctttggcg gcagcaacat cgagccctct    5760
gtgaggagct gcttccagtt cgccaacaac aagcccgaga tcgaggccgc cctgttcctg    5820
gactggatga ggctggagcc tcagagcatg gtgtggctgc ctgtgctgca cagagtggcc    5880
gccgccgaga ccgccaagca ccaggccaag tgcaatatct gcaaggagtg ccccatcatc    5940
ggcttccggt acaggagcct gaagcacttc aactacgaca tctgccagag ctgcttttttc    6000 agcggcagag tggccaaggg ccacaaaatg cactaccccca tggtggagta ctgcacccccc    6060 accacctccg gcgaggatgt gagagacttc gccaaagtgc tgaagaataa gttccggacc    6120
aagcggtact ttgccaagca ccccaggatg ggctacctgc ccgtgcagac cgtgctggaa    6180
ggcgacaaca tggagacctg atgaggagct cgaggcctaa taaagagctc agatgcatcg    6240
atcagagtgt gttggttttt tgtgtgagat ctaggaaccc ctagtgatgg agttggccac    6300
tccctctctg cgcgctcgct cgctcactga ggccgcccgg gcaaagcccg ggcgtcgggc    6360
gacctttggt cgcccggcct cagtgagcga gcgagcgcgc agagagggag tggccaaccc    6420
cccccccccc cccctgcag gcgattctct tgtttgctcc agactctcag gcaatgacct    6480
gatagccttt gtagagacct ctcaaaaata gctaccctct ccggcatgaa tttatcagct    6540
agaacggttg aatatcatat tgatggtgat ttgactgtct ccggcctttc tcacccgttt    6600
gaatctttac ctacacatta ctcaggcatt gcatttaaaa tatatgaggg ttctaaaaat    6660
ttttatcctt gcgttgaaat aaaggcttct cccgcaaaag tattacaggg tcataatgtt    6720
tttggtacaa ccgatttagc tttatgctct gaggctttat tgcttaattt tgctaattct    6780
ttgccttgcc tgtatgattt attggatgtt ggaattcctg atgcggtatt ttctccttac    6840
gcatctgtgc ggtatttcac accgcatatg gtgcactctc agtacaatct gctctgatgc    6900
cgcatagtta agccagcccc gacacccgcc aacacccgct gacgcgccct gacgggcttg    6960
tctgctcccg gcatccgctt acagacaagc tgtgaccgtc tccgggagct gcatgtgtca    7020
gaggttttca ccgtcatcac cgaaacgcgc gagacgaaag ggcctcgtga tacgcctatt    7080
```

```
tttataggtt aatgtcatga taataatggt ttcttagacg tcaggtggca cttttcgggg      7140
aaatgtgcgc ggaacccta tttgtttatt tttctaaata cattcaaata tgtatccgct       7200
catgagacaa taaccctgat aaatgcttca ataatattga aaaaggaaga gtatgagtat      7260
tcaacatttc cgtgtcgccc ttattccctt ttttgcggca ttttgccttc ctgttttttgc     7320 tcacccagaa acgctggtga aagtaaaaga tgctgaagat cagttgggtg cacgagtggg      7380
ttacatcgaa ctggatctca acagcggtaa gatccttgag agttttcgcc ccgaagaacg      7440
ttttccaatg atgagcactt ttaaagttct gctatgtggc gcggtattat cccgtattga      7500
cgccgggcaa gagcaactcg gtcgccgcat acactattct cagaatgact tggttgagta      7560
ctcaccagtc acagaaaagc atcttacgga tggcatgaca gtaagagaat tatgcagtgc      7620
tgccataacc atgagtgata acactgcggc caacttactt ctgacaacga tcggaggacc      7680
gaaggagcta accgcttttt tgcacaacat ggggggatcat gtaactcgcc ttgatcgttg      7740
ggaaccggag ctgaatgaag ccataccaaa cgacgagcgt gacaccacga tgcctgtagc      7800
aatggcaaca acgttgcgca aactattaac tggcgaacta cttactctag cttcccggca      7860
acaattaata gactggatgg aggcggataa agttgcagga ccacttctgc gctcggccct      7920
tccggctggc tggtttattg ctgataaatc tggagccggt gagcgtgggt ctcgcggtat      7980
cattgcagca ctggggccag atggtaagcc ctcccgtatc gtagttatct acacgacggg      8040
gagtcaggca actatggatg aacgaaatag acagatcgct gagataggtg cctcactgat      8100
taagcattgg taactgtcag accaagttta ctcatatata ctttagattg atttaaaact      8160
tcatttttaa tttaaaagga tctaggtgaa gatcctttt gataatctca tgaccaaaat       8220
cccttaacgt gagttttcgt tccactgagc gtcagacccc gtagaaaaga tcaaaggatc      8280
ttcttgagat cctttttttc tgcgcgtaat ctgctgcttg caaacaaaaa aaccaccgct      8340
accagcggtg gtttgtttgc cggatcaaga gctaccaact ctttttccga aggtaactgg      8400
cttcagcaga gcgcagatac caaatactgt ccttctagtg tagccgtagt taggccacca      8460
cttcaagaac tctgtagcac cgcctacata cctcgctctg ctaatcctgt taccagtggc      8520
tgctgccagt ggcgataagt cgtgtcttac cgggttggac tcaagacgat agttaccgga      8580
taaggcgcag cggtcgggct gaacgggggg ttcgtgcaca cagcccagct tggagcgaac      8640
gacctacacc gaactgagat acctacagcg tgagctatga aaagcgcca cgcttcccga       8700 agggagaaag gcggacaggt atccggtaag cggcagggtc ggaacaggag agcgcacgag      8760
ggagcttcca gggggaaacg cctggtatct ttatagtcct gtcgggtttc gccacctctg      8820
acttgagcgt cgatttttgt gatgctcgtc aggggggcgg agcctatgga aaaacgccag      8880
caacgcggcc tttttacggt tcctggcctt ttgctggcct tttgctcaca tgttctttcc      8940
tgcgttatcc cctgattctg tggataaccg tattaccgcc tttgagtgag ctgataccgc      9000
tcgccgcagc cgaacgaccg agcgcagcga gtcagtgagc gaggaagcgg aagagcgccc      9060
aatacgcaaa ccgcctctcc ccgcgcgttg gccgattcat taatgcag                  9108
```

```
<210> SEQ ID NO 26
<211> LENGTH: 9108
<212> TYPE: DNA
<213> ORGANISM: Artificial Sequence
<220> FEATURE:
<223> OTHER INFORMATION: Synthetic

<400> SEQUENCE: 26
aattcccatc atcaataata taccttattt tggattgaag ccaatatgat aatgagggg       60
```

-continued

```
tggagtttgt gacgtggcgc ggggcgtggg aacggggcgg gtgacgtagt agtctctaga      120
ggtccccagc gaccttgacg ggcatctgcc cggcatttct gacagctttg tgaactgggt      180
ggccgagaag gaatgggagt tgccgccaga ttctgacatg gatctgaatc tgattgagca      240
ggcacccctg accgtggccg agaagctgca tcgctggcgt aatagcgaag aggcccgcac      300
cgatcgccct tcccaacagt tgcgcagcct gaatggcgaa tggaattcca gacgattgag      360
cgtcaaaatg taggtatttc catgagcgtt tttcctgttg caatggctgg cggtaatatt      420
gttctggata ttaccagcaa ggccgatagt ttgagttctt ctactcaggc aagtgatgtt      480
attactaatc aaagaagtat tgcgacaacg gttaatttgc gtgatggaca gactctttta      540
ctcggtggcc tcactgatta taaaaacact tctcaggatt ctggcgtacc gttcctgtct      600
aaaatccctt taatcggcct cctgtttagc tcccgctctg attctaacga ggaaagcacg      660
ttatacgtgc tcgtcaaagc aaccatagta cgcgccctgt agcggcgcat taagcgcggc      720
gggtgtggtg gttacgcgca gcgtgaccgc tacacttgcc agcgccctag cgcccgctcc      780
tttcgctttc ttcccttcct ttctcgccac gttcgccggc tttccccgtc aagctctaaa      840
tcgggggctc cctttagggt tccgatttag tgctttacgg cacctcgacc ccaaaaaact      900
tgattagggt gatggttcac gtagtgggcc atcgccctga tagacggttt ttcgcccttt      960
gacgttggag tccacgttct ttaatagtgg actcttgttc caaactggaa caacactcaa     1020
ccctatctcg gtctattctt ttgatttata agggattttg ccgatttcgg cctattggtt     1080
aaaaaatgag ctgatttaac aaaaatttaa cgcgaatttt aacaaaatat taacgtttac     1140
aatttaaata tttgcttata caatcttcct gtttttgggg cttttctgat tatcaaccgg     1200
ggtacatatg attgacatgc tagttttacg attaccgttc atcgcctgca ggggggggg     1260 gggggggtt ggccactccc tctctgcgcg ctcgctcgct cactgaggcc gggcgaccaa     1320
aggtcgcccg acgcccgggc tttgcccggg cggcctcagt gagcgagcga gcgcgcagag     1380
agggagtggc caactccatc actaggggtt cctagatctg aattcgagct tgccacgcat     1440 gcggcagga agagggccta tttcccatga ttccttcata tttgcatata cgatacaagg     1500
ctgttagaga gataattaga attaatttga ctgtaaacac aaagatatta gtacaaaata     1560
cgtgacgtag aaagtaataa tttcttgggt agtttgcagt tttaaaatta tgttttaaaa     1620
tggactatca tatgcttacc gtaacttgaa agtatttcga tttcttggct ttatatatct     1680
tgtggaaagg acgaggatcc agtccctgtc tgcacctgtc tcgagacagg tgcagacagg     1740 gactttttt tgaattccac tacgggtcta ggctgcccat gtaaggaggc aaggcctggg     1800
gacacccgag atgcctggtt ataattaacc ccaacacctg ctgccccccc ccccccaaca     1860
cctgctgcct gagcctgagc ggttacccca ccccggtgcc tgggtcttag ctctgtaca     1920 ccatggagga gaagctcgct ctaaaaataa ccctgtccct ggtggatccc ctgcatgcgg     1980
ccgtccgccc tcggcaccat tcctcacgac accgaaatat ggcgacgggt gaggaatggt     2040
ggggagttat ttttagagcg gtgaggaatg gtgggcaggc agcaggtgtt gggggagtta     2100 ttttttagagc ggggagttat ttttagagcg gtgaggaatg gtggacaccg aaatatggcg     2160
acgggtgagg aatggtgccg tcgccatatt tgggtgtccc gtccgccctc ggccggggcc     2220
gcattcctgg gggccgggcg gtgctcccgc ccgcctcgat aaaaggctcc ggggccggcg     2280
gcggcccact cgagacgttg taaaacgacg gccagtgagc gcgcgtaata cgactcacta     2340
tagggcgaat tggtaccgc caccatggtg tggtgggagg aagtggagga ctgctacgag     2400
```

-continued

```
agagaggacg tgcagaagaa aaccttcacc aagtgggtga acgcccagtt cagcaagttc    2460
ggcaagcagc acatcgagaa cctgttcagc gacctgcagg atggcaggag actgctggac    2520
ctgctggagg gcctgaccgg ccagaagctg cccaaggaga agggcagcac cagagtgcac    2580
gccctgaaca acgtgaacaa ggccctgaga gtgctgcaga caacaacgt ggacctggtg     2640 aacatcggca gcaccgacat cgtggacggc aaccacaagc tgaccctggg cctgatctgg    2700
aacatcatcc tgcactggca ggtgaagaac gtgatgaaga acatcatggc cggcctgcag    2760
cagaccaaca gcgagaagat cctgctgagc tgggtgaggc agagcaccag aaactacccc    2820
caggtgaacg tgatcaactt caccacctcc tggagcgacg gcctggccct gaacgccctg    2880
atccacagcc acagacccga cctgttcgac tggaacagcg tggtgtgtca gcagagcgcc    2940
acccagagac tggagcacgc cttcaacatc gccagatacc agctgggcat cgagaagctg    3000 ctggacccccg aggacgtgga caccacctac cccgacaaga aaagcatcct catgtacatt    3060
accagcctgt ccaggtgct gccccagcag gtgtccatcg aggccatcca ggaagtggaa      3120
atgctgccca ggcccccaa agtgaccaag gaggagcact tccagctgca ccaccagatg      3180
cactacagcc agcagatcac agtgagcctg gcccagggct atgagagaac cagcagcccc    3240
aagcccagat tcaagagcta cgcctacacc caggccgcct acgtgaccac ctccgacccc    3300
accagaagcc ccttccccag ccagcacctg gaggcccccg aggacaagag cttcggcagc    3360
agcctgatgg agagcgaagt gaacctggac agataccaga ccgccctgga ggaagtgctg    3420
tcctggctgc tgagcgccga ggacaccctg caggcccagg gcgagatcag caacgacgtg    3480
gaagtggtga aggaccagtt ccacacccac gagggctaca tgatggatct gaccgcccac    3540
cagggcagag tgggcaatat cctgcagctg ggcagcaagc tgatcggcac cggcaagctg    3600
agcgaggacg aggagaccga agtgcaggag cagatgaacc tgctgaacag cagatgggag    3660
tgcctgagag tggccagcat ggagaagcag agcaacctgc acagagtgct gatggacctg    3720
cagaaccaga agctgaagga gctgaacgac tggctgacca agaccgagga gcggaccaga    3780
aagatggagg aggagcccct gggccccgac ctggaggacc tgaagagaca ggtgcagcag    3840
cacaaagtgc tgcaggagga cctggagcag gagcaggtgc gcgtgaacag cctgacccac    3900
atggtggtgg tcgtggacga gagcagcggc gaccacgcca cagccgccct ggaagagcag    3960
ctgaaagtgc tgggcgacag atggggccaat atttgtaggt ggaccgagga cagatgggtg     4020
ctgctgcagg acacccaccg cctgctccag cagttcccccc tggacctgga gaagttcctg    4080
gcctggctga ccgaggccga aaccaccgcc aatgtgctcc aggacgccac tagaaaggag    4140
aggctgctgg aggacagcaa gggcgtgaaa gagctgatga gcagtggca ggatctgcag       4200 ggcgaaatcg aggcccacac cgacgtgtac cacaacctgg acgagaacag ccagaagatt    4260
ctgaggagcc tggagggcag cgacgacgcc gtcctgctcc agaggaggct ggacaacatg    4320
aacttcaagt ggagcgagct gcggaagaag agcctgaaca tccggagcca cctggaagcc    4380
agcagcgacc agtggaagag actgcacctg agcctgcagg agctgctggt gtggctgcag    4440
ctgaaggacg acgagctgag cagacaggcc cccatcggcg gcgacttccc cgccgtgcag    4500
aagcagaaca acgtgcaccg ggccttcaag agggagctga aaaccaagga acccgtgatc    4560
atgagcaccc tggagacagt gcggatcttc ctgaccgagc agccctgga gggactggag       4620 aagctgtacc aggagcccag agagctgccc cccgaggaga agcccagaa cgtgaccagg       4680 ctgctgagaa agcaggccga ggaagtgaat accgagtggg agaagctgaa tctgcacagc    4740
gccgactggc agagaaagat cgacgagacc ctggagagac tccaggaact gcaggaagcc    4800
```

```
accgacgagc tggacctgaa gctgagacag gccgaagtga tcaagggcag ctggcagcct    4860
gtgggcgatc tgctgatcga ctccctgcag gatcacctgg agaaagtgaa ggccctgcgg    4920
ggcgagatcg ccccctgaa ggagaatgtg agccacgtga acgacctggc cagacagctg     4980
accaccctgg gcatccagct gagcccctac aacctgagca cactggagga tctgaacacc    5040
cggtggaaac tgctgcaggt ggccgtggag gatagagtga ggcagctgca cgaagcccac    5100
agagacttcg gccctgcctc ccagcacttc ctgagcacca gcgtgcaggg ccctgggag     5160 agagccatct cccccaacaa agtgccctac tacatcaacc acgagaccca gaccacctgc    5220
tgggaccacc ctaagatgac cgagctgtat cagagcctgg ccgacctgaa caatgtgcgg    5280
ttcagcgcct acagaaccgc catgaagctg cggagactgc agaaggccct gtgcctggat    5340
ctgctgagcc tgacgccgc ctgcgacgcc ctggaccagc acaacctgaa gcagaatgac     5400
cagcccatgg acatcctgca gatcatcaac tgcctgacca caatctacga ccggctggaa    5460
caggagcaca acaacctggt gaatgtgccc ctgtgcgtgg acatgtgcct gaattggctg    5520
ctgaacgtgt acgacaccgg caggaccggc agaatccgcg tgctgagctt caagaccggc    5580
atcatcagcc tgtgcaaggc ccacctggag gataagtacc gctacctgtt caagcaggtg    5640
gccagcagca ccggcttctg cgatcagagg agactgggcc tgctgctgca cgatagcatc    5700
cagatcccta ggcagctggg cgaagtggcc agctttggcg gcagcaacat cgagccctct    5760
gtgaggagct gcttccagtt cgccaacaac aagcccgaga tcgaggccgc cctgttcctg    5820
gactggatga ggctggagcc tcagagcatg gtgtggctgc ctgtgctgca cagagtggcc    5880
gccgccgaga ccgccaagca ccaggccaag tgcaatatct gcaaggagtg ccccatcatc    5940
ggcttccggt acaggagcct gaagcacttc aactacgaca tctgccagag ctgctttttc    6000
agcggcagag tggccaaggg ccacaaaatg cactacccca tggtggagta ctgcacccc     6060 accacctccg gcgaggatgt gagagacttc gccaaagtgc tgaagaataa gttccggacc    6120
aagcggtact ttgccaagca ccccaggatg ggctacctgc ccgtgcagac cgtgctggaa    6180
ggcgacaaca tggagacctg atgaggagct cgaggcctaa taaagagctc agatgcatcg    6240
atcagagtgt gttggttttt tgtgtgagat ctaggaaccc ctagtgatgg agttggccac    6300
tccctctctg cgcgctcgct cgctcactga ggccgcccgg gcaaagcccg ggcgtcgggc    6360
gacctttggt cgcccggcct cagtgagcga gcgagcgcgc agagagggag tggccaaccc    6420 ccccccccc cccctgcag gcgattctct tgtttgctcc agactctcag gcaatgacct     6480
gatagccttt gtagagacct ctcaaaaata gctaccctct ccggcatgaa tttatcagct    6540
agaacggttg aatatcatat tgatggtgat ttgactgtct ccggcctttc tcacccgttt    6600
gaatctttac ctacacatta tcaggcatt gcatttaaaa tatatgaggg ttctaaaaat     6660
ttttatcctt gcgttgaaat aaaggcttct cccgcaaaag tattacaggg tcataatgtt    6720
tttggtacaa ccgatttagc tttatgctct gaggctttat tgcttaattt tgctaattct    6780
ttgccttgcc tgtatgattt attggatgtt ggaattcctg atgcggtatt ttctccttac    6840
gcatctgtgc ggtatttcac accgcatatg gtgcactctc agtacaatct gctctgatgc    6900
cgcatagtta agccagcccc gacacccgcc aacacccgct gacgcgccct gacgggcttg    6960
tctgctcccg gcatccgctt acagacaagc tgtgaccgtc tccgggagct gcatgtgtca    7020 gaggtttttca ccgtcatcac cgaaacgcgc gagacgaaag gcctcgtga tacgcctatt     7080 tttataggtt aatgtcatga taataatggt ttcttagacg tcaggtggca cttttcgggg    7140
```

-continued

```
aaatgtgcgc ggaaccccta tttgtttatt tttctaaata cattcaaata tgtatccgct    7200
catgagacaa taaccctgat aaatgcttca ataatattga aaaaggaaga gtatgagtat    7260
tcaacatttc cgtgtcgccc ttattccctt ttttgcggca ttttgccttc ctgttttttgc   7320 tcacccagaa acgctggtga aagtaaaaga tgctgaagat cagttgggtg cacgagtggg    7380
ttacatcgaa ctggatctca acagcggtaa gatccttgag agttttcgcc ccgaagaacg    7440
ttttccaatg atgagcactt ttaaagttct gctatgtggc gcggtattat cccgtattga    7500
cgccgggcaa gagcaactcg gtcgccgcat acactattct cagaatgact tggttgagta    7560
ctcaccagtc acagaaaagc atcttacgga tggcatgaca gtaagagaat tatgcagtgc    7620
tgccataacc atgagtgata acactgcggc caacttactt ctgacaacga tcggaggacc    7680
gaaggagcta accgcttttt tgcacaacat gggggatcat gtaactcgcc ttgatcgttg    7740
ggaaccggag ctgaatgaag ccataccaaa cgacgagcgt gacaccacga tgcctgtagc    7800
aatggcaaca acgttgcgca aactattaac tggcgaacta cttactctag cttcccggca    7860
acaattaata gactggatgg aggcggataa agttgcagga ccacttctgc gctcggccct    7920
tccggctggc tggtttattg ctgataaatc tggagccggt gagcgtgggt ctcgcggtat    7980
cattgcagca ctggggccag atggtaagcc ctcccgtatc gtagttatct acacgacggg    8040
gagtcaggca actatggatg aacgaaatag acagatcgct gagataggtg cctcactgat    8100
taagcattgg taactgtcag accaagttta ctcatatata ctttagattg atttaaaact    8160
tcatttttaa tttaaaagga tctaggtgaa gatccttttt gataatctca tgaccaaaat    8220
cccttaacgt gagttttcgt tccactgagc gtcagacccc gtagaaaaga tcaaaggatc    8280
ttcttgagat cctttttttc tgcgcgtaat ctgctgcttg caaacaaaaa aaccaccgct    8340
accagcggtg gtttgtttgc cggatcaaga gctaccaact ctttttccga aggtaactgg    8400
cttcagcaga gcgcagatac caaatactgt ccttctagtg tagccgtagt taggccacca    8460
cttcaagaac tctgtagcac cgcctacata cctcgctctg ctaatcctgt taccagtggc    8520
tgctgccagt ggcgataagt cgtgtcttac cgggttggac tcaagacgat agttaccgga    8580
taaggcgcag cggtcgggct gaacggggg ttcgtgcaca cagcccagct tggagcgaac    8640
gacctacacc gaactgagat acctacagcg tgagctatga gaaagcgcca cgcttcccga    8700
agggagaaag gcggacaggt atccggtaag cggcagggtc ggaacaggag agcgcacgag    8760
ggagcttcca ggggggaaacg cctggtatct ttatagtcct gtcgggtttc gccacctctg    8820
acttgagcgt cgatttttgt gatgctcgtc aggggggcgg agcctatgga aaaacgccag    8880
caacgcggcc tttttacggt tcctggcctt ttgctggcct tttgctcaca tgttctttcc    8940
tgcgttatcc cctgattctg tggataaccg tattaccgcc tttgagtgag ctgataccgc    9000
tcgccgcagc cgaacgaccg agcgcagcga gtcagtgagc gaggaagcgg aagagcgccc    9060
aatacgcaaa ccgcctctcc ccgcgcgttg gccgattcat taatgcag             9108
```

```
<210> SEQ ID NO 27
<211> LENGTH: 3837
<212> TYPE: DNA
<213> ORGANISM: Artificial Sequence
<220> FEATURE:
<223> OTHER INFORMATION: Synthetic

<400> SEQUENCE: 27
atggtgtggt gggaggaagt ggaggactgc tacgagagag aggacgtgca gaagaaaacc      60
ttcaccaagt gggtgaacgc ccagttcagc aagttcggca agcagcacat cgagaacctg     120
```

-continued

```
ttcagcgacc tgcaggatgg caggagactg ctggacctgc tggagggcct gaccggccag      180
aagctgccca aggagaaggg cagcaccaga gtgcacgccc tgaacaacgt gaacaaggcc      240
ctgagagtgc tgcagaacaa caacgtggac ctggtgaaca tcggcagcac cgacatcgtg      300
gacggcaacc acaagctgac cctgggcctg atctggaaca tcatcctgca ctggcaggtg      360
aagaacgtga tgaagaacat catggccggc ctgcagcaga ccaacagcga gaagatcctg      420
ctgagctggg tgaggcagag caccagaaac tacccccagg tgaacgtgat caacttcacc      480
acctcctgga gcgacggcct ggccctgaac gccctgatcc acagccacag acccgacctg      540
ttcgactgga acagcgtggt gtgtcagcag agcgccaccc agagactgga gcacgccttc      600
aacatcgcca gataccagct gggcatcgag aagctgctgg accccgagga cgtggacacc      660 acctacccccg acaagaaaag catcctcatg tacattacca gcctgttcca ggtgctgccc      720
cagcaggtgt ccatcgaggc catccaggaa gtggaaatgc tgcccaggcc ccccaaagtg      780
accaaggagg agcacttcca gctgcaccac cagatgcact acagccagca gatcacagtg      840
agcctggccc agggctatga gagaaccagc agccccaagc ccagattcaa gagctacgcc      900
tacacccagg ccgcctacgt gaccacctcc gaccccacca gaagcccctt ccccagccag      960
cacctggagg cccccgagga caagagcttc ggcagcagcc tgatggagag cgaagtgaac     1020
ctggacagat accagaccgc cctggaggaa gtgctgtcct ggctgctgag cgccgaggac     1080
accctgcagg cccagggcga gatcagcaac gacgtggaag tggtgaagga ccagttccac     1140
acccacgagg gctacatgat ggatctgacc gcccaccagg gcagagtggg caatatcctg     1200
cagctgggca gcaagctgat cggcaccggc aagctgagcg aggacgagga gaccgaagtg     1260
caggagcaga tgaacctgct gaacagcaga tgggagtgcc tgagagtggc cagcatggag     1320
aagcagagca acctgcacag agtgctgatg gacctgcaga accagaagct gaaggagctg     1380
aacgactggc tgaccaagac cgaggagcgg accagaaaga tggaggagga gccccctgggc     1440 cccgacctgg aggacctgaa gagacaggtg cagcagcaca aagtgctgca ggaggacctg     1500
gagcaggagc aggtgcgcgt gaacagcctg acccacatgg tggtggtcgt ggacgagagc     1560
agcggcgacc acgccacagc cgccctggaa gagcagctga aagtgctggg cgacagatgg     1620
gccaatattt gtaggtggac cgaggacaga tgggtgctgc tgcaggacac ccaccgcctg     1680
ctccagcagt ccccctgga cctggagaag ttcctggcct ggctgaccga ggccgaaacc     1740
accgccaatg tgctccagga cgccactaga aaggagaggc tgctggagga cagcaagggc     1800
gtgaaagagc tgatgaagca gtggcaggat ctgcagggcg aaatcgaggc ccacaccgac     1860
gtgtaccaca acctggacga gaacagccag aagattctga ggagcctgga gggcagcgac     1920
gacgccgtcc tgctccagag gaggctggac aacatgaact tcaagtggag cgagctgcgg     1980
aagaagagcc tgaacatccg gagccacctg gaagccagca gcgaccagtg gaagagactg     2040
cacctgagcc tgcaggagct gctggtgtgg ctgcagctga ggacgacga gctgagcaga     2100 caggcccccca tcggcggcga cttccccgcc gtgcagaagc agaacgacgt gcaccgggcc     2160
ttcaagaggg agctgaaaac caaggaaccc gtgatcatga gcaccctgga cagtgcggg     2220 atcttcctga ccgagcagcc cctggaggga ctggagaagc tgtaccagga gcccagagag     2280
ctgccccccg aggagagagc ccagaacgtg accaggctgc tgagaaagca ggccgaggaa     2340
gtgaataccg agtgggagaa gctgaatctg cacagcgccg actggcagag aaagatcgac     2400
gagaccctgg agagactcca ggaactgcag gaagccaccc acgagctgga cctgaagctg     2460
```

-continued

```
agacaggccg aagtgatcaa gggcagctgg cagcctgtgg gcgatctgct gatcgactcc    2520
ctgcaggatc acctggagaa agtgaaggcc ctgcggggcg agatcgcccc cctgaaggag    2580
aatgtgagcc acgtgaacga cctggccaga cagctgacca ccctgggcat ccagctgagc    2640
ccctacaacc tgagcacact ggaggatctg aacacccggt ggaaactgct gcaggtggcc    2700
gtggaggata gagtgaggca gctgcacgaa gcccacagag acttcggccc tgcctcccag    2760
cacttcctga gcaccagcgt gcagggcccc tgggagagag ccatctcccc caacaaagtg    2820
ccctactaca tcaaccacga gacccagacc acctgctggg accaccctaa gatgaccgag    2880
ctgtatcaga gcctggccga cctgaacaat gtgcggttca gcgcctacag aaccgccatg    2940
aagctgcgga gactgcagaa ggccctgtgc ctggatctgc tgagcctgag cgccgcctgc    3000
gacgccctgg accagcacaa cctgaagcag aatgaccagc ccatggacat cctgcagatc    3060
atcaactgcc tgaccacaat ctacgaccgg ctggaacagg agcacaacaa cctggtgaat    3120
gtgcccctgt gcgtggacat gtgcctgaat tggctgctga acgtgtacga caccggcagg    3180
accggcagaa tccgcgtgct gagcttcaag accggcatca tcagcctgtg caaggcccac    3240
ctggaggata agtaccgcta cctgttcaag caggtggcca gcagcaccgg cttctgcgat    3300
cagaggagac tgggcctgct gctgcacgat agcatccaga tccctaggca gctgggcgaa    3360
gtggccagct ttggcggcag caacatcgag ccctctgtga ggagctgctt ccagttcgcc    3420
aacaacaagc ccgagatcga ggccgccctg ttcctggact ggatgaggct ggagcctcag    3480
agcatggtgt ggctgcctgt gctgcacaga gtggccgccg ccgagaccgc caagcaccag    3540
gccaagtgca atatctgcaa ggagtgcccc atcatcggct tccggtacag gagcctgaag    3600
cacttcaact acgacatctg ccagagctgc ttttcagcg gcagagtggc caagggccac    3660
aaaatgcact accccatggt ggagtactgc accccccacca cctccggcga ggatgtgaga    3720
gacttcgcca aagtgctgaa gaataagttc cggaccaagc ggtactttgc caagcacccc    3780
aggatgggct acctgcccgt gcagaccgtg ctggaaggcg acaacatgga gacctga      3837
```

ONE-STEP GENE THERAPY FOR DUCHENNE MUSCULAR DYSTROPHY VIA GENE REPLACEMENT AND ANTI-INFLAMMATION

CROSS-REFERENCE TO RELATED APPLICATIONS

This patent application is the U.S. national phase of PCT/2020/016410, filed Feb. 3, 2020, which claims the benefit of U.S. Provisional Patent Application No. 62/800,484, filed on Feb. 2, 2019, wherein each application is incorporated herein by reference in its entirety herein.

INCORPORATION-BY-REFERENCE OF MATERIALLY SUBMITTED ELECTRONICALLY

Incorporated by reference in its entirety herein is a computer-readable nucleotide/amino acid sequence listing submitted concurrently herewith and identified as follows: One 68,896 Byte ASCII (Text) filed named 754651_ST25 dated Jul. 22, 2021.

BACKGROUND OF THE INVENTION

Duchenne muscular dystrophy (DMD) is a lethal X-linked inherited disease due to dystrophin gene mutation. It is the most common inherited muscular disorder. Heart failure is the leading cause of premature death in DMD patients. Inflammation is a secondary pathological mechanism of DMD in progressive muscle degeneration while the inhibition of NF-kappaB (NF-κB) reduces muscle inflammation, ameliorates muscle pathology, and improves muscle physiological function in DMD mice (Yang, 2012 and Yin, 2017).

Gene therapy-based genetic replacement is a potential treatment for DMD (Wang, 2000), although there is no cure yet for DMD. Chronic inflammation, caused by the up-regulated NF-κB signaling, challenges DMD gene therapy (Mendell J R, 2010 The NEJM). The universal promoters such as the CMV promoter often cause unwished toxicity and immune response in muscle gene therapy. Therefore, a specific muscle-targeted gene delivery system is important for the safety of DMD clinical trial (Wang, 2008). Moreover, the muscle-specific expression mini-dystrophin for DMD therapy should lead to robust expression of mini-dystrophin both in skeletal muscle and cardiac muscle, given that, as noted congestive heart failure is the major complication arising from DMD.

It has been demonstrated that reduction of NF-κB via shRNA technology ameliorates such pathological process in mdx mice (Yang, 2012). Other preliminary results also showed that when two recombinant adeno-associated viral (AAV) vectors respectively carrying mini-dystrophin and NF-κB/p65-shRNA were simultaneously injected into DMD mouse model, expression of mini-dystrophin via reduction of NF-κB increased remarkably. However, the injection of two kinds of AAV is, in many applications, too complex to apply in clinic.

Therefore, a more practical vehicle for introducing both the mini-dystrophin gene and NF-κB/p65-shRNA in both skeletal muscle and cardiac muscle is desired.

BRIEF SUMMARY OF THE INVENTION

In one embodiment, the invention provides a dual-cassette gene vehicle comprising cassettes for expression of both a mini-dystrophin gene and NF-κB/p65-shRNA gene in cardiac muscle tissue and skeletal muscle tissue, which is an adeno-associated viral (AAV) vector, wherein the mini-dystrophin gene is operably linked to a construct comprising a muscle-specific first promoter and a modified Mcken (MCK) enhancer and wherein the NF-κB/p65-shRNA gene is under the control of a second promoter. Also are provided pharmaceutical compositions comprising such gene vehicles and a method for ameliorating Duchenne muscular dystrophy (DMD) employing such gene delivery vehicles and pharmaceutical compositions.

No similar technology exists. The up-regulated NF-kB pathway in DMD, not only plays a key role in the downstream pathogenesis (Acharyya 2007 J Clin Invest), but also clearly affects the efficiency of dystrophin gene replacement (Jayandharan, 2011 PNAS). Dual-therapeutic gene therapy strategy is innovative, should have more benefits than single mini-dystrophin replacement.

BRIEF DESCRIPTION OF THE SEVERAL VIEWS OF THE DRAWING(S)

FIG. 1, panel A depicts schematic diagrams of single- and dual-cassette AAV constructs. FIG. 1, panel B depicts Western blot of dystrophin tested in cardiac tissues. FIG. 1, panel C depicts Immunofluorescence (IF) staining of dystrophin in cardiac and liver tissues. FIG. 1, panel D depicts IF staining of mini-dystrophin in heart tissue, skeletal muscle tissue (DIA is diaphragm, GAS is gastrocnemius muscle, TA is tibialis anterior muscle) and liver tissue from mdx/utm$^{-/-}$ mice systemically treated by dual-cassette AAV and single-cassette AAV treatment. Mini-dystrophin was expressed successfully in heart, diaphragm, GAS, and TA muscle in both singe-homo and dual-homo group. Moreover, there was no expression of mini-dystrophin in liver tissue, indicating the tissue specificity. FIG. 1, panel E is a graph showing the mini-dystrophin positive cell ratio in different kinds of tissue. There was no difference in heart and DIA tissue between single-homo and dual-homo group. But, the dual-homo group have much more mini-dystrophin expressed in GAS and TA muscle. (**** means $p < 0.0001$)

FIG. 2, panel A, depicts IF staining of CD68, CD4, CD8 and p-P65 in gastrocnemius muscles. FIG. 2, panel B, depicts IF staining of p-P65 in heart and gastrocnemius muscles. WT: wild-type, Dual-homo: Dual-cassette AAV treated dKO-homo, Single-homo: Single-cassette AAV treated dKO-homo, Ct-homo: Untreated dKO-homo. Magnification: 200×. (* means $p < 0.05$,  means $p < 0.01$, * means $p < 0.001$, **** means $p < 0.0001$)

FIG. 3, panel A, represents characterization of the transgenic and knockdown mice discussed in Example 2. FIG. 3, panel B depicts Western blot analysis of expressions of dystrophin and p-P65 in GAS muscles at the ages of 2 months. FIG. 3, panel C depicts Hematoxylin and Eosin (H&E) staining, and IF staining of dystrophin and β-sarcoglycan performed in GAS muscles at the same age.

FIG. 4A depicts Masson's Trichrome staining and IF staining of mIgG, CD68, CD4, and CD8 in gastrocnemius muscles of the transgenic and knockdown mice at the ages of 2 months. FIG. 4B presents statistical analysis revealing that CD68, CD4, and CD8 showed significant differences between groups of different transgenic and knockdown mice. *$p < 0.01$, $p < 0.001$, and *$p < 0.0001$. FIG. 4C depicts the results of IF staining of CD8, CD4, and CD68 in rAAV-treated heart and/or gastrocnemius muscles (there are almost no CD8 positive in heart tissue). In the graphs in the lower panel, the Y axis is the positive cell number per visual frame. Single-homo has less immune cell infiltration than Ct-homo group, and dual-homo less than single-homo group. (n=3, * means $p < 0.05$,  means $p < 0.01$, * means $p < 0.001$, **** means $p < 0.0001$). FIG. 4D depicts the overall health of AAV-treated mice, wherein (1) denotes WT, (2) denotes dual-homo, (3) denotes single-homo, and (4) denotes Ct-homo. The muscle function at 1 month and 2 month of age with 0 to 200 HZ frequency is shown in the top graphs. The body weight from different groups at 1 month and 2 months of age are shown in the lower graph (* means $p < 0.05$,  means $p < 0.01$, * means $p < 0.001$, **** means $p < 0.0001$).

FIG. 5B graphically indicates the location of certain genetic elements within the pAAV-M1p65EnsynOpti3978 (SEQ ID NO: 1) and pAAV-M2p65EnsynOpti3978 (SEQ ID NO: 23) vectors.

FIG. 6B graphically indicates the location of certain genetic elements within the pAAV-M1p65EnsynOpti3837 (SEQ ID NO: 25) and pAAV-M2p65EnsynOpti3837 (SEQ ID NO: 26) vectors.

DETAILED DESCRIPTION OF THE INVENTION

Figures 1D, 1E:
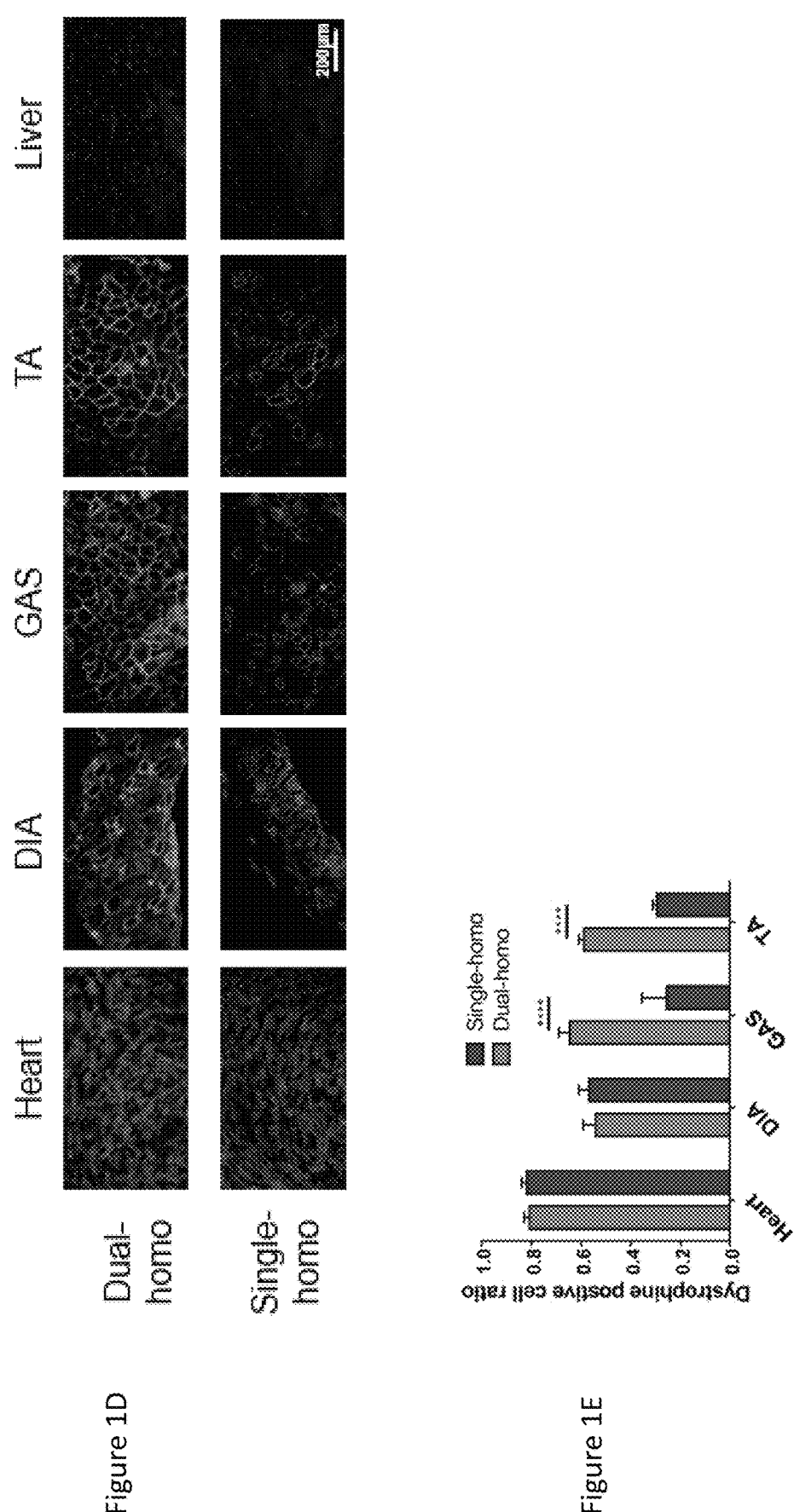

In one embodiment, the invention provides a dual-cassette gene vehicle comprising cassettes for expression of both a mini-dystrophin gene and NF-κB/p65-shRNA gene in cardiac muscle tissue and skeletal muscle tissue, which is an adeno-associated viral (AAV) vector, wherein the mini-dystrophin gene is operably linked to a construct comprising a muscle-specific first promoter and a modified Mcken (MCK) promoter enhancer and wherein the NF-κB/p65-shRNA gene is operably linked to a second promoter.

The AAV vector can be derived from any strain of AAV suitable for use as a gene therapy vector, such as are known to persons of ordinary skill in the art. Purely for example, the parent AAV strain can be an AAV1, AAV2, AAV6, or AAV9, although others can be employed.

Exemplary AAV vectors in the context of the present invention (or plasmids for generating the vectors encoding, such from which the viral sequences would be understood by a person of ordinary skill in the art) are described herein as AAV-M1p65EnsynOpti3978 or AAV-M2p65EnsynOpti3978 (including a plasmid for generating such vectors). The sequences of these exemplary AAVs for use in the context of the present invention comprise the sequence of SEQ ID NO:1, which is AAV-M1p65EnsynOpti3978; SEQ ID NO: 23, which is AAV-M2p65EnsynOpti3978; SEQ ID NO: 25, which is AAV-M1p65EnsynOpti3837; and SEQ ID NO: 26, which is AAV-M2p65EnsynOpti3837.

AAV-M2p65EnsynOpti3978 differs from AAV-M1p65EnsynOpti3978 in that it comprises the sequence agtccctgtctgcacctgtctcgagacaggtgcagacagggactttttttt (encoding m2p65 shRNA, SEQ ID NO:22 at bp 1701-1751 in place of the sequence encoding m1p65 present in SEQ ID NO:1 (tgtgtccattgtctcactcctcgaggagtgagacaatggacacatttttttt (SEQ ID NO:17)).

Similarly, AAV-M2p65EnsynOpti3837 differs from AAV-M1p65EnsynOpti3837 in that it comprises the sequence agtccctgtctgcacctgtctcgagacaggtgcagacagggacttttttttt (encoding m2p65 shRNA, SEQ ID NO:22 at bp 1701-1751 in place of the sequence encoding m1p65 present in SEQ ID NO: 25 (tgtgtccattgtctcactcctcgaggagtgagacaatggacacatttttttt (SEQ ID NO:17)).

As noted, an AAV for use in the context of the present invention comprises a cassette for expression of a mini-dystrophin gene in cardiac muscle and in skeletal muscle. Preferably, the mini-dystrophin gene is human-codon optimized. For example, a human optimized mini-dystrophin gene including 5 rods (1, 2, 22, 23, 24) and 3 hinges (1, 3, 4), and CR domain can be used to treat DMD animal models and for human clinical trial and ultimately for treatment of CDM. See, for example, Kornegay J N, et al., *Molecular Therapy.* 2010, 18(8):1501-1508, PMID: 20517298 (incorporated herein by reference in its entirety). The sequence of one such human optimized mini-dystrophin (also referred to as micro-dystrophin) is opti-DysΔ3978 (comprising 3978 base pairs) and is set forth at sequence ID NO:2:

```
atggtgtggtgggaggaagtggaggactgctacgagagagaggacgtgcagaagaaaaccttcaccaagtgggtgaacgcccagt tcagcaagttcggcaagcagcacatcgagaacctgttcagcgacctgcaggatggcaggagactgctggacctgctggagggcctg accggccagaagctgcccaaggagaagggcagcaccagagtgcacgccctgaacaacgtgaacaaggccctgagagtgctgca gaacaacaacgtggacctggtgaacatcggcagcaccgacatcgtggacggcaaccacaagctgaccctgggcctgatctggaac atcatcctgcactggcaggtgaagaacgtgatgaagaacatcatggccggcctgcagcagaccaacagcgagaagatcctgctgag ctgggtgaggcagagcaccagaaactacccccaggtgaacgtgatcaacttcaccacctcctggagcgacggcctggccctgaacg ccctgatccacagccacagacccgacctgttcgactggaacagcgtggtgtgtcagcagagcgccacccagagactggagcacgc cttcaacatcgccagataccagctgggcatcgagaagctgctggacccgaggacgtggacaccacctaccccgacaagaaaagc atcctcatgtacattaccagcctgttccaggtgctgccccagcaggtgtccatcgaggccatccaggaagtggaaatgctgcccaggc cccccaaagtgaccaaggaggagcacttccagctgcaccaccagatgcactacagccagcagatcacagtgagcctggcccaggg ctatgagagaaccagcagccccaagcccagattcaagagctacgcctacacccaggccgcctacgtgaccacctccgacccccacca gaagcccttccccagccagcacctggaggccccgaggacaagagcttcggcagcagcctgatgggagagcgaagtgaacctgg acagataccagaccgccctggaggaagtgctgtcctggctgctgagcgccgaggacaccctgcaggcccagggcgagatcagca acgacgtggaagtggtgaaggaccagttccacacccacgagggctacatgatggatctgaccgcccaccagggcagagtgggcaa tatcctgcagctgggcagcaagctgatcggcaccggcaagctgagcgaggacgaggagaccgaagtgcaggagcagatgaacct
```

-continued

```
gctgaacagcagatgggagtgcctgagagtggccagcatggagaagcagagcaacctgcacagagtgctgatggacctgcagaac cagaagctgaaggagctgaacgactggctgaccaagaccgaggagcggaccagaaagatggaggaggagcccctgggccccga cctggaggacctgaagagacaggtgcagcagcacaaagtgctgcaggaggacctggagcaggagcaggtgcgcgtgaacagcct gacccacatggtggtggtcgtggacgagagcagcggcgaccacgccacagccgccctggaagagcagctgaaagtgctgggcga cagatgggccaatatttgtaggtggaccgaggacagatgggtgctgctgcaggaccagcccgacctggcccctggcctgaccacca tcggcgccagccccacccagaccgtgaccctggtgacccagcccgtggtgacaaaggagaccgccatcagcaagctggagatgc ccagctccctgatgctggaagtgcccacccaccgcctgctccagcagttcccctggacctggagaagttcctggcctggctgaccg aggccgaaaccaccgccaatgtgctccaggacgccactagaaaggagaggctgctggaggacagcaagggcgtgaaagagctga tgaagcagtggcaggatctgcagggcgaaatcgaggcccacaccgacgtgtaccacaacctggacgagaacagccagaagattct gaggagcctggagggcagcgacgacgccgtcctgctccagaggaggctggacaacatgaacttcaagtggagcgagctgcggaa gaagagcctgaacatccggagccacctggaagccagcagcgaccagtggaagagactgcacctgagcctgcaggagctgctggt gtggctgcagctgaaggacgacgagctgagcagacaggccccatcggcggcgacttccccgccgtgcagaagcagaacgacgt gcaccgggccttcaagagggagctgaaaaccaaggaacccgtgatcatgagcaccctggagacagtgcggatcttcctgaccgag cagcccctggagggactggagaagctgtaccaggagcccagagagctgccccccgaggagagagcccagaacgtgaccaggct gctgagaaagcaggccgaggaagtgaataccgagtgggagaagctgaatctgcacagcgccgactggcagagaaagatcgacga gaccctggagagactccaggaactgcaggaagccaccgacgagctggacctgaagctgagacaggccgaagtgatcaagggcag ctggcagcctgtgggcgatctgctgatcgactccctgcaggatcacctggagaaagtgaaggccctgcggggcgagatcgcccccc tgaaggagaatgtgagccacgtgaacgacctggccagacagctgaccaccctgggcatccagctgagcccctacaacctgagcac actggaggatctgaacacccggtggaaactgctgcaggtggccgtggaggatagagtgaggcagctgcacgaagcccacagaga cttcggccctgcctcccagcacttcctgagcaccagcgtgcagggcccctgggagagagccatctcccccaacaaagtgccctacta catcaaccacgagacccagaccacctgctgggaccaccctaagatgaccgagctgtatcagagcctggccgacctgaacaatgtgc ggttcagcgcctacagaaccgccatgaagctgcggagactgcagaaggccctgtgcctggatctgctgagcctgagcgccgcctgc gacgccctggaccagcacaacctgaagcagaatgaccagcccatggacatcctgcagatcatcaactgcctgaccacaatctacgac cggctggaacaggagcacaacaacctggtgaatgtgcccctgtgcgtggacatgtgcctgaattggctgctgaacgtgtacgacacc ggcaggaccggcagaatccgcgtgctgagcttcaagaccggcatcatcagcctgtgcaaggcccacctggaggataagtaccgcta cctgttcaagcaggtggccagcagcaccggcactgcgatcagaggagactgggcctgctgctgcacgatagcatccagatccctag gcagctgggcgaagtggccagctttggcggcagcaacatcgagccctctgtgaggagctgttccagttcgccaacaacaagcccg agatcgaggccgccctgttcctggactggatgaggctggagcctcagagcatggtgtggctgcctgtgctgcacagagtggccgcc gccgagaccgccaagcaccaggccaagtgcaatatctgcaaggagtgcccccatcatcggcttccggtacaggagcctgaagcactt caactacgacatctgccagagctgctttttcagcggcagagtggccaagggccacaaaatgcactaccccatggtggagtactgcac ccccaccacctccggcgaggatgtgagagacttcgccaaagtgctgaagaataagttccggaccaagcggtactttgccaagcaccc caggatgggctacctgcccgtgcagaccgtgctggaaggcgacaacatggagacctga
```

This sequence is included within SEQ ID NO: 1 and SEQ ID NO: 23 as base-pairs 2365-6342.

Within SEQ ID NO: 2, the following domains of the human optimized mini-dystrophin can be identified. Their nucleotide position within the coding sequence for the human optimized mini-dystrophin gene is indicated in FIG. 5B:

N-TERMINUS OF HUMAN DYSTROPHIN (756 base pairs); SEQ ID NO: 3:

```
atggtgtggtgggaggaagtggaggactgctacgagagagaggacgtgcagaagaaaaccacaccaagtgggtgaacgcccagt tcagcaagttcggcaagcagcacatcgagaacctgttcagcgacctgcaggatggcaggagactgctggacctgctggagggcctg accggccagaagctgcccaaggagaagggcagcaccagagtgcacgccctgaacaacgtgaacaaggccctgagagtgctgca
``` gaacaacaacgtggacctggtgaacatcggcagcaccgacatcgtggacggcaaccacaagctgaccctgggcctgatctggaac atcatcctgcactggcaggtgaagaacgtgatgaagaacatcatggccggcctgcagcagaccaacagcgagaagatcctgctgag ctgggtgaggcagagcaccagaaactacccccaggtgaacgtgatcaacttcaccacctcctggagcgacggcctggccctgaacg ccctgatccacagccacagacccgacctgacgactggaacagcgtggtgtgtcagcagagcgccacccagagactggagcacgc cttcaacatcgccagataccagctgggcatcgagaagctgctggaccccgaggacgtggacaccacctaccccgacaagaaaagc atcctcatgtacattaccagcctgtccaggtgctgccccagcaggtgtccatcgaggccatccaggaagtggaa;

HINGE1 (225 base pairs); SEQ ID NO: 4:
atgctgcccaggcccccaaagtgaccaaggaggagcacttccagctgcaccaccagatgcactacagccagcagatcacagtga gcctggcccagggctatgagagaaccagcagccccaagcccagattcaagagctacgcctacacccaggccgcctacgtgaccac ctccgaccccaccagaagcccttccccagccagcacctggaggcccccgaggac;

ROD1 (333 base pairs); SEQ ID NO: 5:
agcgaagtgaacctggacagataccagaccgccctggaggaagtgctgtcctggctgctgagcgccgaggacaccctgcaggccc agggcgagatcagcaacgacgtggaagtggtgaaggaccagttccacacccacgagggctacatgatggatctgaccgcccacca gggcagagtgggcaatatcctgcagctgggcagcaagctgatcggcaccggcaagctgagcgaggacgaggagaccgaagtgc aggagcagatgaacctgctgaacagcagatgggagtgcctgagagtggccagcatggagaagcagagcaacctgcacaga;

ROD2 (327 base pairs); SEQ ID NO: 6:
gtgctgatggacctgcagaaccagaagctgaaggagctgaacgactggctgaccaagaccgaggagcggaccagaaagatggag gaggagcccctgggcccccgacctggaggacctgaagagacaggtgcagcagcacaaagtgctgcaggaggacctggagcagga gcaggtgcgcgtgaacagcctgacccacatggtggtggtcgtggacgagagcagcggcgaccacgccacagccgccctggaaga gcagctgaaagtgctgggcgacagatgggccaatatttgtaggtggaccgaggacagatgggtgctgctgcaggac;

HINGE3 (141 base pairs); SEQ ID NO: 7:
cagcccgacctggcccctggcctgaccaccatcggcgccagccccacccagaccgtgaccctggtgacccagcccgtggtgacaa aggagaccgccatcagcaagctggagatgcccagctccctgatgctggaagtgccc;

ROD22 (348 base pairs); SEQ ID NO: 8;
acccaccgcctgctccagcagttcccccctggacctggagaagttcctggcctggctgaccgaggccgaaaccaccgccaatgtgctc caggacgccactagaaaggagaggctgctggaggacagcaagggcgtgaaagagctgatgaagcagtggcaggatctgcaggg cgaaatcgaggcccacaccgacgtgtaccacaacctggacgagaacagccagaagattctgaggagcctggagggcagcgacga cgccgtcctgctccagaggaggctggacaacatgaacttcaagtggagcgagctgcgggaagaagagcctgaacatccggagccac ctggaagcc;

ROD23 (387 base pairs); SEQ ID NO: 9:
agcagcgaccagtggaagagactgcacctgagcctgcaggagctgctggtgtggctgcagctgaaggacgacgagctgagcaga caggcccccatcggcggcgacttccccgccgtgcagaagcagaacgacgtgcaccgggccttcaagagggagctgaaaaccaag gaacccgtgatcatgagcaccctggagacagtgcggatcttcctgaccgagcagcccctggagggactggagaagctgtaccagga gcccagagagctgcccccccgaggagagagcccagaacgtgaccaggctgctgagaaagcaggccgaggaagtgaataccgagt gggagaagctgaatctgcacagcgccgactggcagagaaagatcgacgag;

ROD24 (327 base pairs); SEQ ID NO: 10:
accctggagagactccaggaactgcaggaagccaccgacgagctggacctgaagctgagacaggccgaagtgatcaagggcagc tggcagcctgtgggcgatctgctgatcgactccctgcaggatcacctggagaaagtgaaggccctgcggggcgagatcgccccct gaaggagaatgtgagccacgtgaacgacctggccagacagctgaccaccctgggcatccagctgagcccctacaacctgagcaca ctggaggatctgaacacccggtggaaactgctgcaggtggccgtggaggatagagtgaggcagctgcacgaa;

HINGE4 (216 base pairs); SEQ ID NO: 11:
gcccacagagacttcggccctgcctcccagcacttcctgagcaccagcgtgcagggcccctgggagagagccatctcccccaacaa agtgccctactacatcaaccacgagacccagaccacctgctgggaccacccaagatgaccgagctgtatcagagcctggccgacct gaacaatgtgcggttcagcgcctacagaaccgccatgaagctg;

```
                             -continued
CYSTEINE-RICH (CR)-DOMAIN (888 base pairs); SEQ ID NO: 12:
cggagactgcagaaggccctgtgcctggatctgctgagcctgagcgccgcctgcgacgccctggaccagcacaacctgaagcaga atgaccagcccatggacatcctgcagatcatcaactgcctgaccacaatctacgaccggctggaacaggagcacaacaacctggtga atgtgcccctgtgcgtggacatgtgcctgaattggctgctgaacgtgtacgacaccggcaggaccggcagaatccgcgtgctgagctt caagaccggcatcatcagcctgtgcaaggccacctggaggataagtaccgctacctgttcaagcaggtggccagcagcaccggct tctgcgatcagaggagactgggcctgctgctgcacgatagcatccagatccctaggcagctgggcgaagtggccagctttggcggc agcaacatcgagccctctgtgaggagctgcttccagttcgccaacaacaagcccgagatcgaggccgccctgttcctggactggatg aggctggagcctcagagcatggtgtggctgcctgtgctgcacagagtggccgccgccgagaccgccaagcaccaggccaagtgca atatctgcaaggagtgccccatcatcggcttccggtacaggagcctgaagcacttcaactacgacatctgccagagctgctttttcagc ggcagagtggccaagggccacaaaatgcactaccccatggtggagtactgcaccccccaccacctccggcgaggatgtgagagactt cgccaaagtgctgaagaataagttccggaccaagcggtactttgccaagcacccaggatgggctacctgcccgtgcagaccgtgct ggaaggcgacaacatggagacc; and
STOP CODON (3 base pairs); SEQ ID NO: 13: tga
```

Thus, a suitable human optimized mini-dystrophin gene for use in the context of the present invention can comprise, consist essentially of, or consist of SEQ ID NO: 2 and can comprise a domain represented by a sequence selected from the group of sequences consisting of any of SEQ ID NOs: 3-13, although such domain(s) can comprise, consist essentially of, or consist of such sequence. Of course it will be apparent that the human optimized mini-dystrophin gene can comprise a functional variant of SEQ ID NOs: 2-13. A functional variant, in this context, indicates that a variant of a given sequence can be employed so long as the encoded gene product retains the function of the reference encoded molecule. Thus, sequence variants from any of SEQ ID NOs: 2-13 can be employed for encoding a suitable human optimized mini-dystrophin in the context of the present invention. Such variants can vary from the exemplary sequences set forth herein by retaining from about 75% to about 99% to one or more of SEQ ID Nos:2-13, such as at least about 75%, such as at least about 80%, or at least about 90%, at least about 95%, or at least about 99% sequence identity to one or more of SEQ ID Nos:2-13.

Figure 6A:
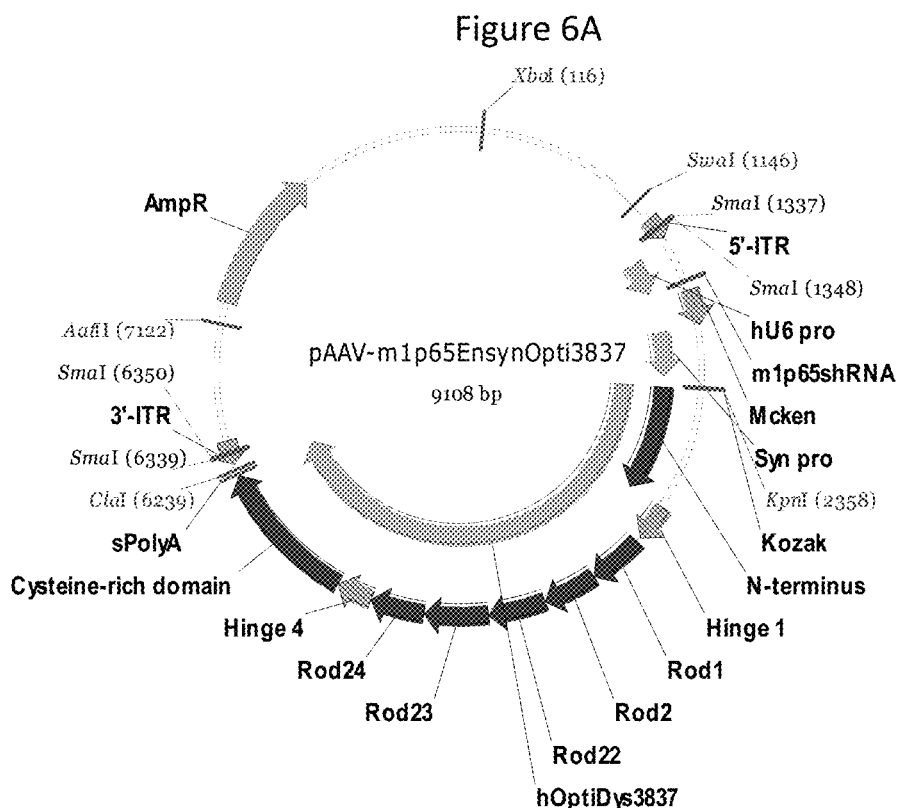
FIG. 6A is a schematic vector diagram representing embodiments of the present invention: vector pAAV-M1p65EnsynOpti3837 (SEQ ID NO: 25) and pAAV-M2p65EnsynOpti3837 (SEQ ID NO: 26).
Figure 6A:
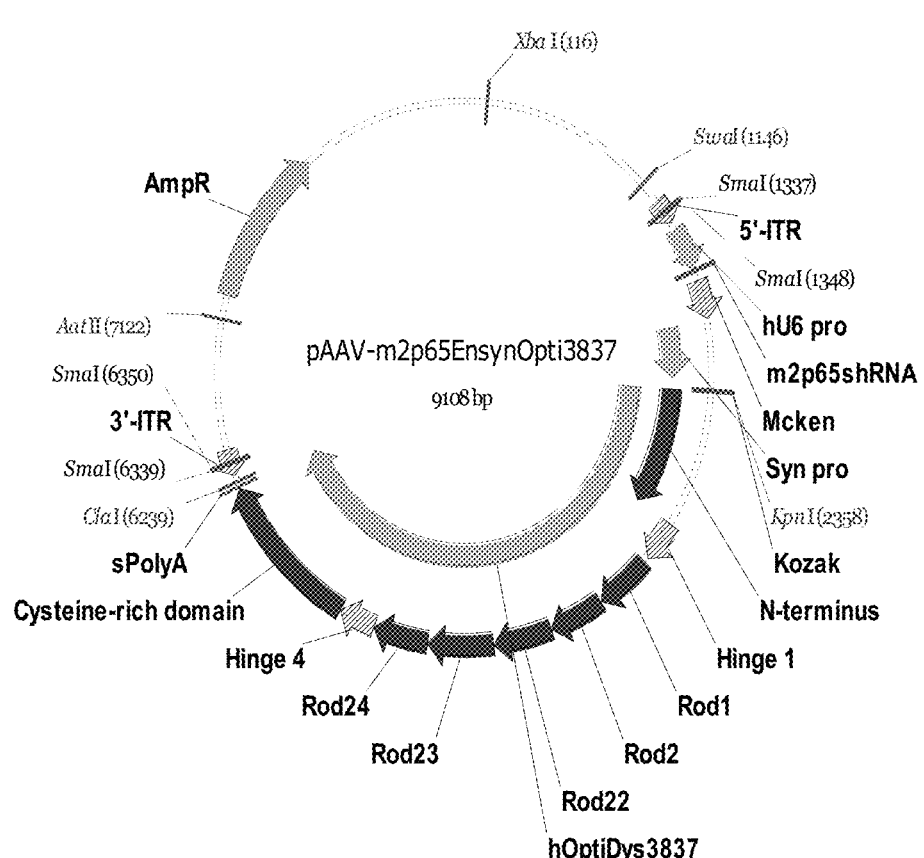

Other mini-dystrophins (micro-dystrophins) with a smaller size for use in the invention include mini-dystrophin genes (human or canine) containing an N-terminus, 5 rods (Rods 1, 2, 22, 23, 24), 2 hinges (Hinge 1 and 4), and a cysteine-rich domain, such as hΔDys3849 and hOptiΔDys3837. hOptiΔDys3837 differs from hΔDys3849 in that (i) in that hOptiΔDys3837 is codon-optimized and (ii) 12 bases of full exon 79 have been removed. The essential functional domains are the same. The sequence of hOptiΔDys3837 (also referred to as opti-DysΔ3837), which comprises 3837 base pairs, is set forth in SEQ ID NO: 27. This sequence is included within SEQ ID NOs:25 and 26 as base-pairs 2365-6201 (FIG. 6B). Exemplary mini-dystrophins are described in Wang et al., *PNAS USA,* 97(25): 13714-13719 (2000), PMID 11095710; Wang et al., *Gene Therapy,* 15(15): 1099-1106 (2008), PMID 18432277; Wang et al., *Gene Therapy,* 15(22): 1489-1499 (2008), PMID 18563184; Romesh et al., *Journal of Muscle Research and Cell Motility,* 27(1): 53-67 (2006), PMID 16496225; and Koppanati et al., *Gene Therapy,* 17(11): 1355-1362 (2010), PMID 20535217, all of which are incorporated by reference.

Thus, a suitable human optimized mini-dystrophin gene for use in the context of the present invention can comprise, consist essentially of, or consist of SEQ ID NO: 27 and can comprise a domain represented by a sequence selected from the group of sequences consisting of any of SEQ ID NOs: 3-6 and 8-13, although such domain(s) can comprise, consist essentially of, or consist of such sequence. Of course it will be apparent that the human optimized mini-dystrophin gene can comprise a functional variant of SEQ ID NOs: 3-6, 8-13, and 27. Such variants can vary from the exemplary sequences set forth herein by retaining from about 75% to about 99% to one or more of SEQ ID NOs: 3-6, 8-13, and 27, such as at least about 75%, such as at least about 80%, or at least about 90%, at least about 95%, or at least about 99% sequence identity to one or more of SEQ ID NOs: 3-6, 8-13, and 27.

As noted, within the AAV useful in the context of the present invention, the cassette for expression of the mini-dystrophin gene in cardiac muscle and in skeletal muscle comprises muscle-specific first promoter and a modified MCK promoter enhancer. Within this cassette, the mini-dystrophin gene is operably linked to the muscle-specific first promoter and the modified MCK promoter enhancer such that the expression of the mini-dystrophin is under the control of the muscle-specific first promoter and the modified MCK promoter enhancer.

For use in the context of the present invention, the modified muscle MCK promoter enhancer which permits muscle-specific expression. Preferably, the modified muscle MCK promoter enhancer truncated version of the MCK promoter, which is useful given the size limitations of the AAV genome. For one proffered modified muscle MCK promoter enhancer, in addition to muscle-specific cis-elements, mef-2, right e-box (mef1) and a/t-rich elements can be maintained in the enhancer region for the tissue-specificity in differentiated muscle, including two right e-boxes and one s5 modified region. See Bing Wang, et al., *Gene Ther.,* 2008, 15:1489-1499. PMID: 18563184 (incorporated herein by reference in its entirety). The sequence of one preferred modified muscle MCK promoter enhancer (comprising 216 base pairs) is set forth at nucleotides 1757-1972 of SEQ ID NO:1 (FIG. 5B), SEQ ID NO: 23 (FIG. 5B), SEQ ID NO: 25 (FIG. 6B), and SEQ ID NO: 26 (FIG. 6B) and is represented by sequence ID NO:14:

```
ccactacgggtctaggctgcccatgtaaggaggcaaggcctggggacaccc gagatgcctggttataattaaccccaacacctgctgccccccccccccccaa
```

-continued cacctgctgcctgagcctgagcggttaccccaccccggtgcctgggtctta ggctctgtacaccatggaggagaagctcgctctaaaaataaccctgtccct ggtggatcccct.

Thus, a suitable modified muscle MCK promoter enhancer for use in the context of the present invention can comprise, consist essentially of, or consist of SEQ ID NO:14. Of course it will be apparent that the modified muscle MCK promoter can comprise a functional variant of SEQ ID NO:14. A functional variant, in this context, indicates that a variant of a given sequence can be employed so long as the variant retains the function of the reference sequence. Thus, sequence variants from SEQ ID NO:14 can be employed as modified muscle MCK promoter enhancer in the context of the present invention. Such variants can vary from the exemplary sequence set forth herein by retaining from about 75% to about 99% sequence identity to SEQ ID NO:14, such as at least about 75%, such as at least about 80%, or at least about 90%, at least about 95%, or at least about 99% sequence identity to SEQ ID NO:14.

For use in the context of the present invention, the muscle-specific first promoter permits muscle-specific expression. One preferred modified muscle-specific first promoter is a synthetic promoter (Syn), which, in addition to muscle-specific cis-elements, comprises a MEF-2 and a right e-box. See Bing Wang, et al., *Gene Ther.*, 2008, 15:1489-1499. PMID: 18563184 (incorporated herein by reference in its entirety). The sequence of one preferred muscle-specific first promoter (comprising 317 base pairs) is set forth at nucleotides 1973-2289 of SEQ ID NO:1 (FIG. 5B), SEQ ID NO: 23 (FIG. 5B), SEQ ID NO: 25 (FIG. 6B), and SEQ ID NO: 26 (FIG. 6B) and is represented by sequence ID NO:15:

gcatgcggccgtccgccctcggcaccattcctcacgacaccgaaatatggc gacgggtgaggaatggtggggagttattttttagagcggtgaggaatggtgg gcaggcagcaggtgttgggggagttattttttagagcggggagttatttttta gagcggtgaggaatggtggacaccgaaatatggcgacgggtgaggaatggt gccgtcgccatatttgggtgtcccgtccgccctcggccggggccgcattcc tgggggccgggcggtgctcccgcccgcctcgataaaaggctccggggccgg cggcggcccac.

Thus, a suitable muscle-specific first promoter for use in the context of the present invention can comprise, consist essentially of, or consist of SEQ ID NO:15. Of course it will be apparent that the muscle-specific first promoter can comprise a functional variant of SEQ ID NO:15. A functional variant, in this context, indicates that a variant of a given sequence can be employed so long as the variant retains the function of the reference sequence. Thus, sequence variants from SEQ ID NO:15 can be employed as muscle-specific first promoter in the context of the present invention. Such variants can vary from the exemplary sequence set forth herein by retaining from about 75% to about 99% sequence identity to SEQ ID NO: 15, such as at least about 75%, such as at least about 80%, or at least about 90%, at least about 95%, or at least about 99% sequence identity to SEQ ID NO:15.

The cassette for expression of the mini-dystrophin gene in cardiac muscle and in skeletal muscle also can contain other desired elements for enhancing expression of the mini-dystrophin gene. For example, the exemplary AAV sequence set forth in SEQ ID NO:1 includes a Kozak consensus sequence (GCCACC (SEQ ID NO:16)), which serves as an enhancer for translation of the mini-dystrophin gene. See Bing Wang, et al., *Journal of Orthopaedic Research,* 2009, 27:4,421-42. PMID: 18973234 (incorporated herein by reference in its entirety).

As noted, an AAV for use in the context of the present invention comprises a cassette in which the NF-κB/p65-shRNA gene is operably linked to a second promoter. The mouse NF-κB/p65-shRNA cassette specifically silences subunit 65 of NF-κB/p65. See Qing Yang, et al. *Gene Ther.* 2012, 19:1196-1204, PubMed PMID: 22278411 (incorporated herein by reference in its entirety). Without being bound by theory, it is believed that the specific silencing of subunit 65 of NF-κB/p65 reduces inflammation, which can lead to more robust expression of the mini-dystrophin gene. A mouse specific NF-κB/p65-shRNA includes 51 base pairs and is included at nucleotides 1701-1751 of SEQ ID NO:1 (FIG. 5B) and SEQ ID NO: 25 (FIG. 6B). Its sequence is tgtgtccattgtctcactcctcgaggagtgagacaatggacacattttttt (SEQ ID NO:17). Another mouse specific NF-κB/p65-shRNA includes 51 base pairs and is included at nucleotides 1701-1751 of SEQ ID NO:23 (FIG. 5B) and SEQ ID NO: 26 (FIG. 6B). Its sequence is agtccctgtctgcacctgtctcgagacaggtgca-gacagggactttttttt (SEQ ID NO:22). Furthermore, for use in human clinical trials or in treatment of DMD, an shRNA sequence based on the human NF-κB sequence preferably is employed. Human siRNA oligo sequence, named (REL1096 (gattgaggagaaacgtaaatt SEQ ID NO:24)) to inhibit the NF-kB the induction of inflammatory cytokine in human syn-oviocytes (Lee, Ui Jin et al., *Mol Biol Rep* (2008) 35:291-298 (incorporated herein in its entirety by reference)) and its inhibition of constitutive or tumor necrosis factor-induced NF-kB in cancer cells (Jutooru, Indira et al., *J. Biol. Chem.* (2010), 285: 25332-25344 (incorporated herein in its entirety by reference)) is known to persons of ordinary skill.

Thus, a suitable NF-κB/p65-shRNA for use in the context of the present invention can comprise, consist essentially of, or consist of SEQ ID NO:17, SEQ ID NO:22, or SEQ ID NO:24. Of course it will be apparent that the NF-κB/p65-shRNA can comprise a functional variant of SEQ ID NO:17 or SEQ ID NO:22. A functional variant, in this context, indicates that a variant of a given sequence can be employed so long as the variant retains the function of the reference sequence. Thus, sequence variants from SEQ ID NO:17, SEQ ID NO:22, or SEQ ID NO:24 can be employed, which inhibit in the context of the present invention. Such variants can vary from the exemplary sequence set forth herein by retaining from about 75% to about 99% sequence identity to SEQ ID NO:17, such as at least about 75%, such as at least about 80%, or at least about 90%, at least about 95%, or at least about 99% sequence identity to SEQ ID NO:17, SEQ ID NO:22, or SEQ ID NO:24.

As noted, the NF-κB/p65-shRNA is operably linked to (under transcriptional control) of a second promoter. A preferred promoter for this purpose is the U6 promoter, most preferably the human U6 promoter. See Qing Yang, et al. *Gene Ther.* 2012, 19:1196-1204, PubMed PMID: 22278411 (incorporated herein by reference in its entirety). The sequence of the human U6 promoter includes 241 base pairs and is included at nucleotides 1452-1692 of SEQ ID NO: 1 (FIG. 5B), SEQ ID NO: 23 (FIG. 5B), SEQ ID NO: 25 (FIG. 6B), and SEQ ID NO: 26 (FIG. 6B). Its sequence is (SEQ ID NO:18) is:

```
gagggcctatttcccatgattccttcatatttgcatatacgatacaaggct gttagagagataattagaattaatttgactgtaaacacaaagatattagta caaaatacgtgacgtagaaagtaataatttcttgggtagtttgcagtttta aaattatgttttaaaatggactatcatatgcttaccgtaacttgaaagtat ttcgatttcttggctttatatatcttgtggaaaggac.
```

Thus, a suitable second promoter for use in the context of the present invention can comprise, consist essentially of, or consist of SEQ ID NO:18. Of course it will be apparent that the second promoter a functional variant of SEQ ID NO:18. A functional variant, in this context, indicates that a variant of a given sequence can be employed so long as the variant retains the function of the reference sequence. Thus, sequence variants from SEQ ID NO:18 can be employed as the second promoter in the context of the present invention. Such variants can vary from the exemplary sequence set forth herein by retaining from about 75% to about 99% sequence identity to SEQ ID NO:18, such as at least about 75%, such as at least about 80%, or at least about 90%, at least about 95%, or at least about 99% sequence identity to SEQ ID NO:18.

Furthermore, while the U6 promoter can be used to drive expression of the NF-κB/p65-shRNA, other promoters can suitably be used as the second promoter. Many promoters are known to persons of ordinary skill in the art. Preferably a promoter operably linked to drive expression of the κB/p65-shRNA should have activity in both immune cells and dytrophic muscle cells. Examples of some suitable promoters are Polymerase III promoters such as human H1 and U6.

Aside from dual cassettes for expression of both a mini-dystrophin gene and NF-xB/p65-shRNA gene in cardiac muscle tissue and skeletal muscle tissue, an AAV for use in the context of the present can comprise other elements. For example, 5' and 3' inverted terminal repeats (ITRs) facilitate packaging the genome into the vector package. See Xiao, et al., *J. Virol.* 1998; 72(3):2224-32. PubMed PMID: 9499080 (incorporated herein by reference in its entirety). Sequences of such 3' and 5' ITRs are known to persons of ordinary skill in the art, but examples include:

```
ttggccactccctctctgcgcgctcgctcgctcactgaggccgggcgacca aaggtcgcccgacgcccgggctttgcccgggcggcctcagtgagcgagcga gcgcgcagagagggagtggccaactccatcactaggggttcct
(SEQ ID NO: 19 - 5' ITR and)

aggaaccctagtgatggagttggccactccctctctgcgcgctcgctcgc tcactgaggccgcccgggcaaagcccgggcgtcgggcgacctttggtcgcc cggcctcagtgagcgagcgagcgcgcagagagggagtggccaa
(SEQ ID NO: 20 - 3'ITR).
```

Furthermore, inclusion of a poly(A) signal sequence can enhance gene expression from the vector. See Bing Wang, et al., *Proc. Nat. Acad. Sci. USA.,* 2000, 97(25):13714-13719, PMID: 11095710 (incorporated herein by reference in its entirety). PolyA sequences are well known to persons of ordinary skill in the art, but a non-limiting example of one suitable poly(A) is tcgaggcctaataaagagctcagatgcatc-gatcagagtgtgttggtttttgtgtgaga (SEQ ID NO:21). The location of these sequences within SEQ ID NOs: 1, 23, 25, and 26 is depicted in FIGS. 5B and 6B). Other useful genetic elements for inclusion include genes conferring resistance to antibiotics, such as ampicillin, which is commonly used during culture of viral packaging cells to select for infected cells to increase viral titer.

The AAV for use as the dual-cassette gene vehicle comprising cassettes for expression of both a mini-dystrophin gene and NF-κB/p65-shRNA gene in cardiac muscle tissue and skeletal muscle tissue in the context of the present invention can be generated by standard molecular and cellular techniques known to persons of ordinary skill. For example, a plasmid comprising the dual cassettes and other AAV sequences can be can engineered by standard molecular techniques. The plasmid then can be employed to generate a viral vector, for example by transfecting it into a suitable packaging cell line (such as HEK 293 cells or HEK 293T cells, but other cell lines can be employed). Transformants can be selected from the population, for example by exposing the culture to compound for which the AAV vector genome confers resistance (e.g., ampicillin). Once the cells have produced AAV packages, they can be purified (for example, using CsCl gradients or via other methods known to persons of ordinary skill). Thereafter they can be stored (e.g., cryopreserved) or formulated for use.

In an embodiment, the invention provides a pharmaceutical composition comprising the inventive gene vehicle comprising cassettes for expression of both a mini-dystrophin gene and NF-κB/p65-shRNA gene in cardiac muscle tissue and skeletal muscle tissue (the AAV described herein) and a pharmaceutically acceptable carrier. The pharmaceutically acceptable carrier can include any carrier known to persons of ordinary skill. The carrier of the composition can be any suitable carrier for the vector. The carrier typically will be liquid and formulated for injection, but also can be solid, or a combination of liquid and solid components. The carrier desirably is a pharmaceutically acceptable (e.g., a physiologically or pharmacologically acceptable) carrier (e.g., excipient or diluent). Pharmaceutically acceptable carriers are well known and are readily available. The choice of carrier will be determined, at least in part, by the particular vector and the particular method used to administer the composition.

The composition can further comprise any other suitable components, especially for enhancing the stability of the composition and/or its end-use. Accordingly, there is a wide variety of suitable formulations of the composition of the invention. The following formulations and methods are merely exemplary and are in no way limiting.

Formulations suitable for parenteral administration include aqueous and non-aqueous, isotonic sterile injection solutions, which can contain anti-oxidants, buffers, bacteriostats, and solutes that render the formulation isotonic with the blood or other tissue of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use.

In addition, the composition can comprise additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the vector and physiological distress. Immune system suppressors can be administered with the composition method to reduce any immune response to the vector itself or associated with a disorder. Alternatively, immune enhancers can be included in the composition to upregulate the body's natural defenses against disease. Antibiotics, i.e., microbicides and fungicides, can be present to reduce the risk of infection associated with gene transfer procedures and other disorders.

In an embodiment, the invention provides a method for ameliorating Duchenne muscular dystrophy (DMD), the method comprising administrating the gene vehicle (AAV) or the pharmaceutical composition as described herein a patient or subject who is suffering from or at risk of developing DMD in an amount and at a location to ameliorate DMD. In this context the patient or subject typically is a human (e.g., a patient suffering from and being treated for DMD or a subject of a clinical trial). However, the method also can be applied to non-human animals for assessment of gene expression or animal models of DMD. Such non-human animals typically are those commonly employed in laboratory studies (e.g., mice, rats, dogs, non-human primates, etc.).

In performance of the method, the gene vehicle or the pharmaceutical composition typically is administered by parenteral (e.g., intraperitoneal, intravenous, intramuscular, etc.) injection. However other routes of delivery may be suitable and employed by a treating physician or for a clinical trial protocol.

The amount of viral particles to deliver in performing the inventive method can be determined by a physician or laboratory researcher and may depend on the size of the subject or species of the subject or patient. However enough of the gene vehicle (AAV) should be delivered to infect cardiac and skeletal muscles to result in the expression from the dual cassettes within the inventive gene vehicle. For laboratory studies, as reported in the Examples below, $10^{11}$ AAV genomes were injected intraperitoneally, although somewhat less than this may be sufficient. However, for human patients or subjects, a greater number of AAV genomes may be necessary or desirable. For example, in carrying out the inventive method, at least $10^8$ AAV genomes, or at least $10^9$ AAV genomes, or at least $10^{10}$ AAV genomes, or at least $10^{11}$ AAV genomes, or at least at least $10^{12}$ AAV genomes, or at least $10^{13}$ AAV genomes, or at least $10^4$ AAV genomes (or at least "about" such numbers of AAV genomes may be employed. While the upper limit of AAV genomes to administer to the patient or subject may be, in part, depending on how concentrated a pharmaceutical composition can be formulated, up to $10^{20}$ AAV genomes, or up to $10^{19}$ AAV genomes, or up to $10^{18}$ AAV genomes, or up to $10^{17}$ AAV genomes, or up to $10^{16}$ AAV genomes, or up to $10^{20}$ AAV genomes (or up to "about" such numbers of AAV genomes) may suitably be administered. Greater or lesser amounts of AAV genomes can be employed to; the dose ultimately decided by a physician, laboratory researcher, or clinical trial protocol. Typical doses are $2 \times 10^{10}$-$1 \times 10^{11}$ viral genome/kg (patient body) (see Duan, DS, *Mol. Ther.* 2018, 26:2337-2356, Table 4 (incorporated herein by reference in its entirety)

The following examples further illustrate the invention but, of course, should not be construed as in any way limiting its scope.

EXAMPLES

In the Examples below, a such dual-cassette AAV vector having a modified MCK enhancer (Mcken) and a muscle-specific synthetic promoter (Syn) driving human-codon optimized mini-dystrophin gene (Wang, 2008 Gene Therapy, and Kornegay, 2010 Molecular Therapy) was generated. This ensured efficient and specific expression of mini-dystrophin gene in whole-body muscles of a severe DMD murine model, the dystrophin/utrophin double knockout (dys–/–:utro–/–, dKO-homo) mouse. as demonstrated by high level expression in cardiac muscle. Such dual-therapeutic approach also resulted in efficient inhibition of chronic inflammation, especially in skeletal muscle of this severe DMD model.

Next, through cross-breeding of Tg.dKO-het (dys–/–: utro+/–).p65+/– mice, both Tg.dKO-homo.p65+/+ and Tg.dKO-homo.p65+/– mice were obtained. It also was observed that synergistic therapeutic effects were beneficial from the genetic ablation of the p65 subunit of NF-κB (p65+/–) accompanied with a transgenic human mini-dystrophin gene in a severe DMD murine model, without toxicity.

In summary, a novel AAV vector with a dual-cassette containing a compact promoter for muscle-specific dystrophin gene expression and specific shRNA of NF-κB for anti-inflammation may enhance therapeutic efficiency and safety of DMD gene therapy.

Example 1

This Example demonstrates the optimization of a dual-cassette AAV vector via the design of a modified MCK enhancer (Mcken) and a muscle-specific synthetic promoter (Syn) driving human-codon optimized mini-dystrophin gene (Wang, 2008 and Kornegay, 2010). This ensured efficient and specific expression of mini-dystrophin gene in whole-body muscles of a severe DMD murine model, especially in cardiac muscle. Such dual-therapeutic approach also resulted in efficient inhibition of chronic inflammation, especially in skeletal muscle.

Methods

Figure 5A:
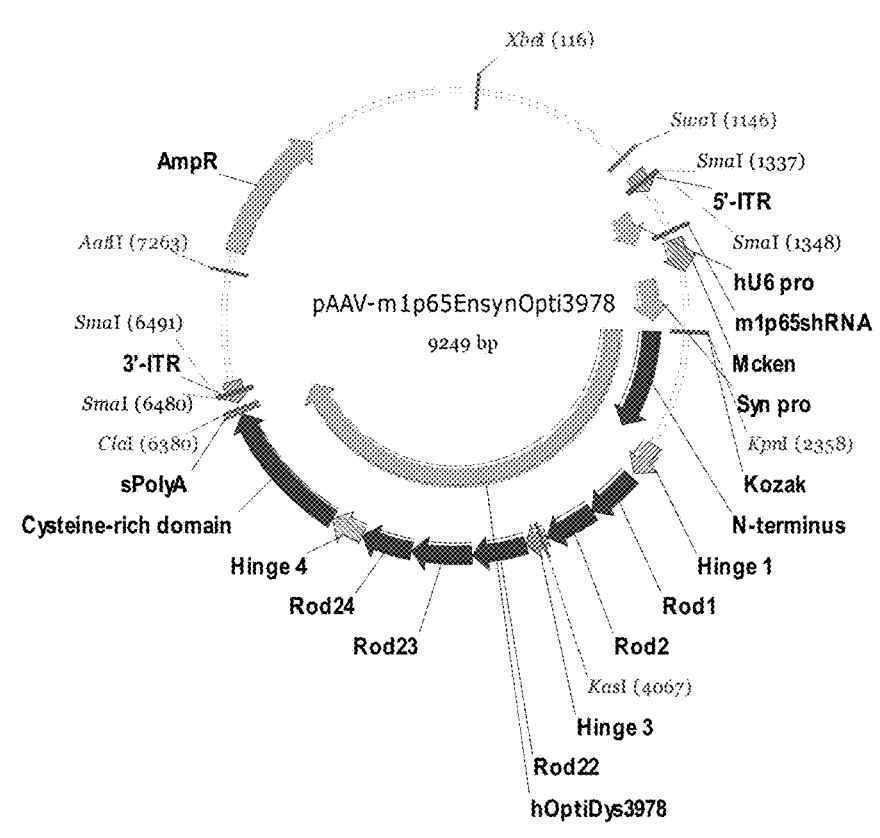
FIG. 5A is a schematic vector diagram representing embodiments of the present invention: vector pAAV-M1p65EnsynOpti3978 (SEQ ID NO: 1) and pAAV-M2p65EnsynOpti3978 (SEQ ID NO: 23).
Figure 5A:
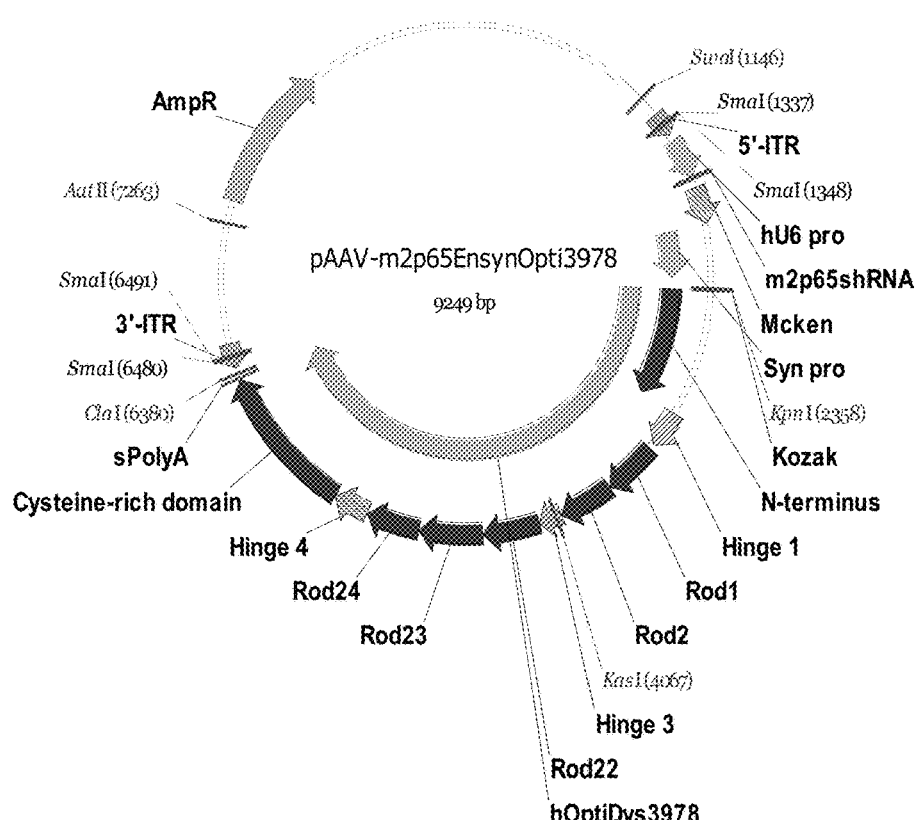

IACUC protocol was approved for all strains of mice in this study. Wild-type (WT, C57/BL10) mice were purchased from Jackson Laboratory. The dystrophin/utrophin double knockout (dys–/–:utro–/–, dKO-homo) mice were derived from in-house colony through breeding of heterozygous dystrophin/utrophin double knockout mice (dys–/–: utro+/–). As shown in FIG. 1, panel A, the single cassette of mini-dystrophin AAV vector was generated that a computer-codon optimized mini-dystrophin gene, including N-terminus, 5 Rods (1, 2, 22, 23, 24), 3 Hinges (1, 3, 4), and CR terminus, was cloned into a single AAV vector and driven by a MCK modified enhancer regulated muscle synthetic promoter. Based on published functional mouse NF-κB/p65 mRNA sequences (Yang, 2012), two versions (m1 and m2) of mouse p65/shRNA driven by a U6 promoter that were designed and respectively cloned into the single cassette pAAV(ss)-Mcken-Syn-hOptiDys3978 (Kornegay, 2010). The plasmids were purified through CsCl gradient ultracentrifugation. One such plasmid, pAAV-M1p65EnsynOpti3978 is schematically depicted in FIGS. 5A and 5B, and its sequence is set forth in SEQ ID NO:1.

The AAV9 vectors were packaged by co-transfection in 293 cells and purified by twice CsCl gradient ultracentrifugation according to Yang, 2012. A single I.P. injection with 50 μl ($1 \times 10^{11}$ viral genome particles) virus was performed to 5-day-old dKO-homo pups, and the cryostat sections of cardiac and skeletal muscle, as well as liver tissue were analyzed at the ages of 8 weeks. Sections were applied for immunofluorescence (IF) staining with antibodies against human dystrophin (Rods 1 & 2), phosphorylated NF-κB/p65

(#8242, Cell Signaling), CD4 (BD550280, BD Biosciences), CD8 (ab22378, Abcam), CD68 (#9936, Cell Signaling), ColIV (ab6586, Abcam). Nuclei were also stained with DAPI (in blue). Images were taken at 200× magnification.

Results

As shown in FIG. 1, panel B, cardiac muscles were tested by western blot assay, efficient expressions of full-length dystrophin (450 kDa) in WT mice and mini-dystrophin (150 kDa) in dKO-homo mice treated with either single or dual-cassette vector were observed. IF staining of dystrophin also confirmed the specificity of muscle-targeted gene delivery in heart and skeletal muscle tissue (diaphragm, gastrocnemius muscle, and tibialis anterior muscle), as demonstrated by no expression of dystrophin in liver tissue (FIG. 1, panels C and D). There was no difference the dystrophin positive cell ratio in heart and diaphragm tissue between mice treated with either single or dual-cassette vector (FIG. 1, panel E). But, the mice treated with dual-cassette vector have much more mini-dystrophin expressed in gastrocnemius muscle and tibialis anterior muscle (FIG. 1, panel E).

The results demonstrated reduced inflammation in skeletal muscle treated by the dual-cassette AAV vector, which shows synergistic effects can be achieved by a single AAV vector combining dystrophin gene replacement and anti-inflammation.

Figure 2A:
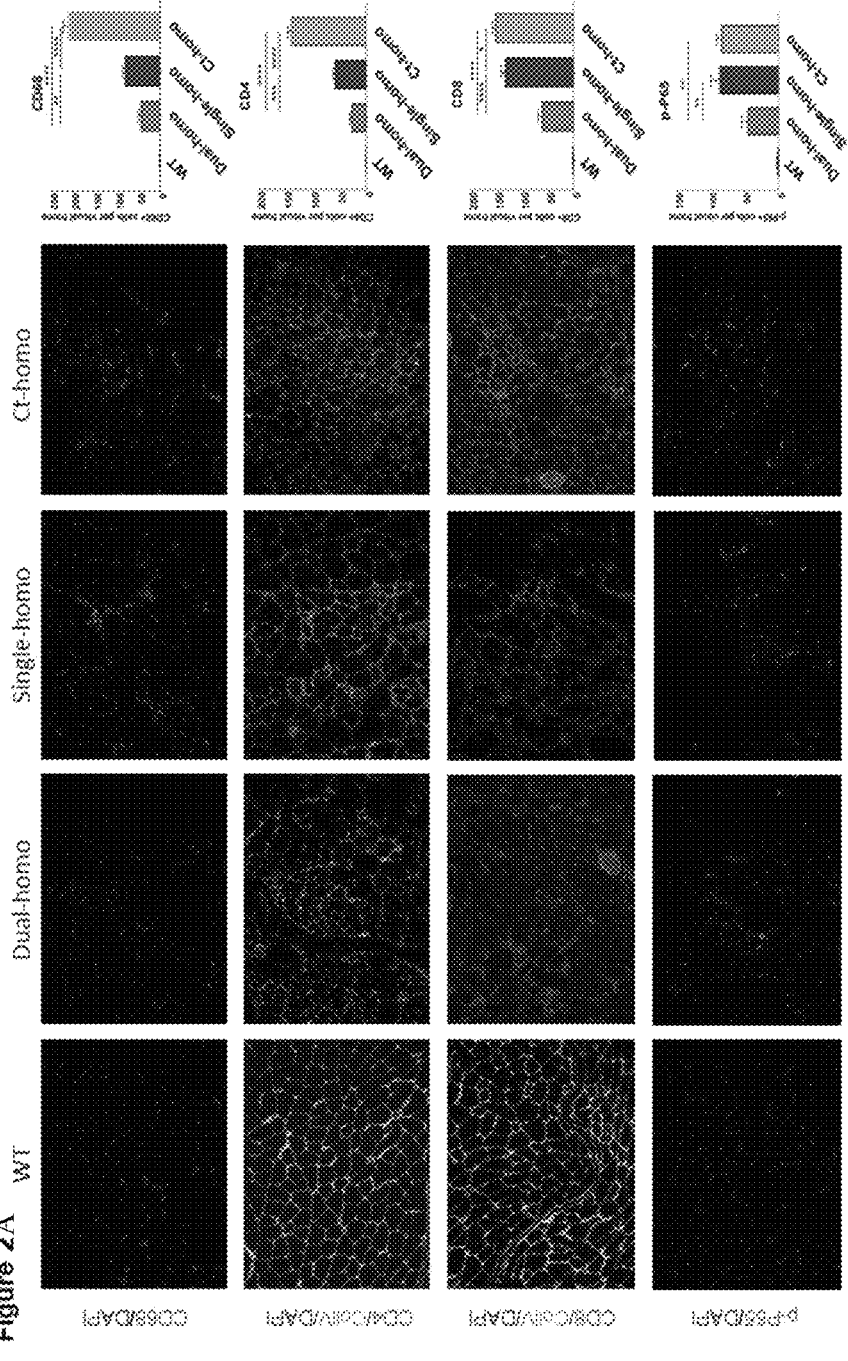
Figure 2B:
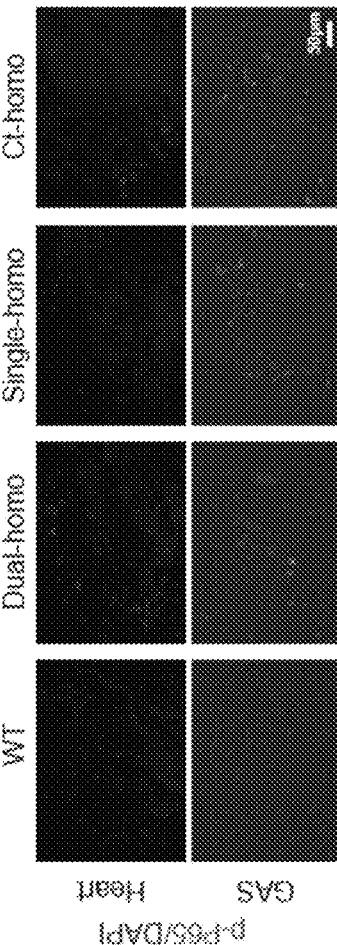

Gastrocnemius muscles (GAS) were IF stained by p-P65 to determine the level of active NF-κB, CD4 and CD8 to evaluate immune cell infiltration, and CD68 to detect inflammatory macrophage. As shown in FIG. 2A, GAS muscle treated with dual-cassette AAV represented the less inflammatory markers such as CD4, CD8 and CD68 via the reduction of NF-κB, comparing the treatment with a single-cassette AAV. WT GAS did not show inflammation in muscle. However, the non-treated GAS of dKO-homo mice had remarkable inflammation. FIG. 2B demonstrates the IF staining of p-P65 in heart and GAS muscle. In heart tissue, there are almost no positive cells in all groups. But, in GAS muscle, the dual-homo group showed much less p-P65 than single-homo and untreated homo mice group (Ct-homo).

These results demonstrate that there is a remarkable reduction of active NF-κB (p-P65) observed in skeletal muscle treated by dual-cassette AAV compared to single cassette AAV or no treatment. Unlike in skeletal muscle in mdx/utm−/− mice, there was no significant difference of active NF-κB (p-P65) in cardiac muscle, no matter whether the mice were treated with dual-cassette AAV or single-cassette AAV or no treatment.

Discussion

The systemic efficacy of muscle-targeted gene replacement combining inhibition of NF-κB via a single AAV vehicle was investigated, which ensures efficient expression of computer-codon optimized human mini-dystrophin and reduction of inflammation in whole body muscles. These results demonstrate that a novel AAV vector with a dual-cassette containing a compact promoter for muscle-specific dystrophin gene expression and specific shRNA of NF-κB for anti-inflammation may enhance therapeutic efficiency and safety of DMD gene therapy, in clinical trials or otherwise.

Example 2

This Example demonstrates that synergistic therapeutic effects may be beneficial from the genetic ablation of the p65 subunit of NF-κB (p65+/−) accompanied with a transgenic human mini-dystrophin gene in a severe DMD murine model (dys−/−:utro−/−, dKO-homo).

Methods

IACUC protocol was approved for all strains of mice in this study. Wild-type (WT, C57/BL10) and mdx (dys−/−) mice were purchased from Jackson Laboratory. The mdx.p65+/− and human mini-dystrophin (DysΔ3990).mdx (Tg.mdx) mice (Yin, 2017 and Wang, 2000) were derived from an in-house colony. Through cross-breeding of Tg.dKO-het (dys−/−:utro+/−).p65+/− mice, both Tg.dKO-homo.p65+/+ and Tg.dKO-homo.p65+/− mice were obtained (FIG. 3, panel A).

Cryostat sections were prepared using gastrocnemius muscle (GAS) of mice at the ages of 2 months. Sections were applied for Hematoxylin and Eosin (H&E) and Masson's trichrome staining. Immunofluorescence (IF) staining was also performed by the use of antibodies against human dystrophin (Rods 1 & 2), β-sarcoglycan (NCL-a-SARC, Leica), phosphorylated NF-κB/p65 (p-P65) (#8242, Cell Signaling), CD68 (#9936, Cell Signaling), CD4 (BD550280, BD Biosciences), CD8 (ab22378, Abcam), ColIV (ab6586, Abcam), and mouse IgG (mIgG) (C2181, Sigma). Nuclei were stained with DAPI. Images were taken at 200× magnification. Protein expressions were detected by Western blot analysis with antibody against GAPDH as an endogenous control. Statistical analysis was performed using GraphiPad Prism 7 software. All results were given as the mean±SD (n≥4 per group). Differences were considered statistically significant when the P-value was <0.05.

Results

Figure 3:
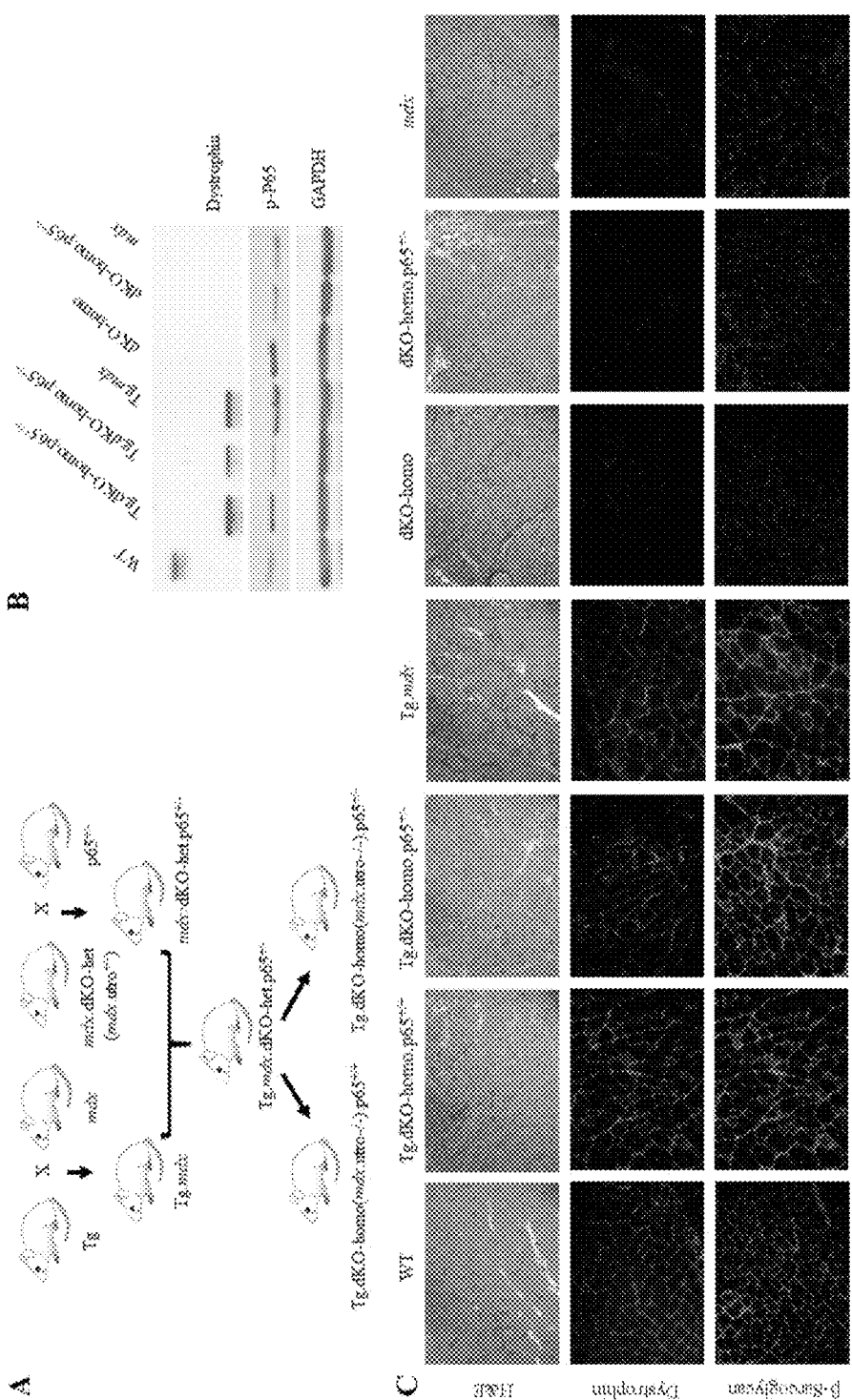

As shown in FIG. 3, panel B, high level of expression of full-length dystrophin (450 kDa) in WT or mini-dystrophin (150 kDa) in Tg mice was detected. Phosphorylated NF-κB (65 kDa) was found to be significantly reduced in p65 knockout background (Tg.dKO-homo.p65+/+ vs Tg.dKO-homo.p65+/−; dKO-homo.p65+/+ vs dKO-homo.p65+/−). In FIG. 3, panel C, high levels of dystrophin or dystrophin associated protein (β-sarcoglycan) was also found in mini-dystrophin transgenic DMD mice accompanied with improved morphology of muscle cells in H&E staining.

Figure 4A:
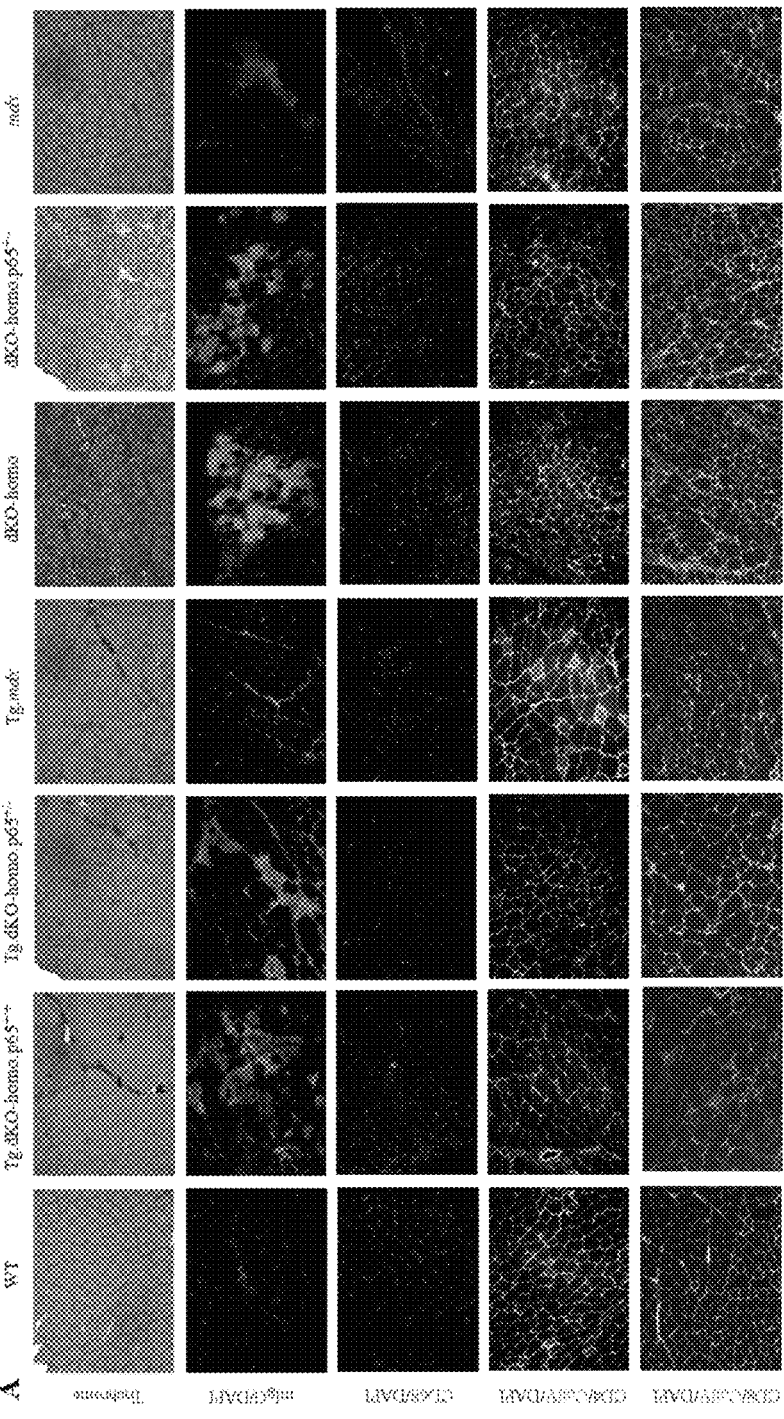

Moreover, Masson's Trichrome staining and IF staining of mIgG, CD68, CD4, and CD8 were applied to analyze muscle fibrosis, necrosis, and inflammation. Results in FIG. 4A demonstrated the improvement in cell morphology, and reduction in fibrosis, necrosis and inflammation at background with p65 knockdown, especially Tg.dKO-homo.p65+/− vs Tg.dKO-homo.p65+/+, indicating that genetic ablation of NF-κB/p65 subunit could reduce inflammation levels.

Figure 4B:
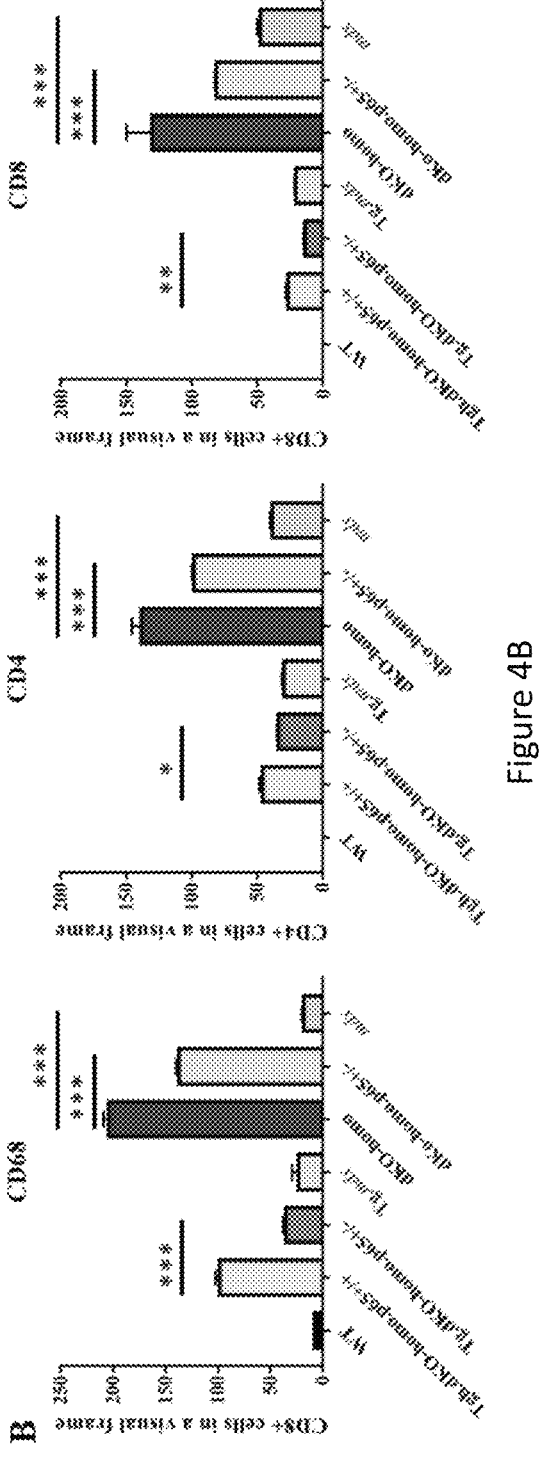

As shown in FIG. 4B, statistical analysis from IF staining of CD68, CD4 and CD8 in GAS muscles (Tg.dKO-homo.p65+/+ vs Tg.dKO-homo.p65+/−; dKO-homo.p65+/+ vs dKO-homo.p65+/−) at the ages of 2 months demonstrated that genetic reduction of p65 subunit could significantly reduce levels of fibrosis, necrosis and infiltration of immune cells, counted from more than 200 total cells per group. The inflammation was not observed in WT mice, and untreated dKO-homo GAS muscle showed higher level of inflammation comparing mdx mice (FIGS. 4A and 4B), consistent with previous observations (Mu, 2015).

Figure 4C:
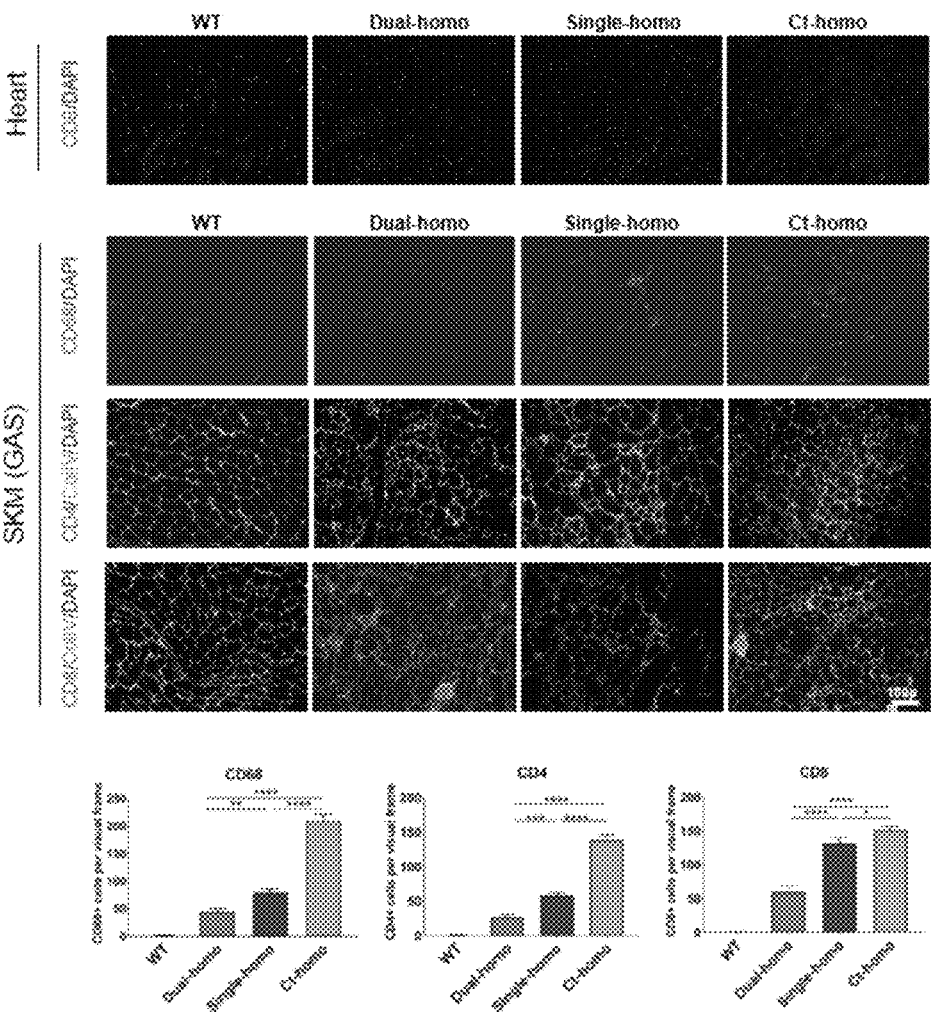

As shown in FIG. 4C, unlike in skeletal muscle in mdx/utrn−/− mice, there was no significant difference of CD68+ macrophages in cardiac muscle, no matter whether the mice were treated with dual-cassette AAV or single-cassette AAV or no treatment. In contrast, there was a remarkable reduction of CD4+ and CD8+ immune cells and CD68+ macrophages observed in skeletal muscle treated with dual-cassette AAV compared to single-cassette AAV.

19

Figure 4D:
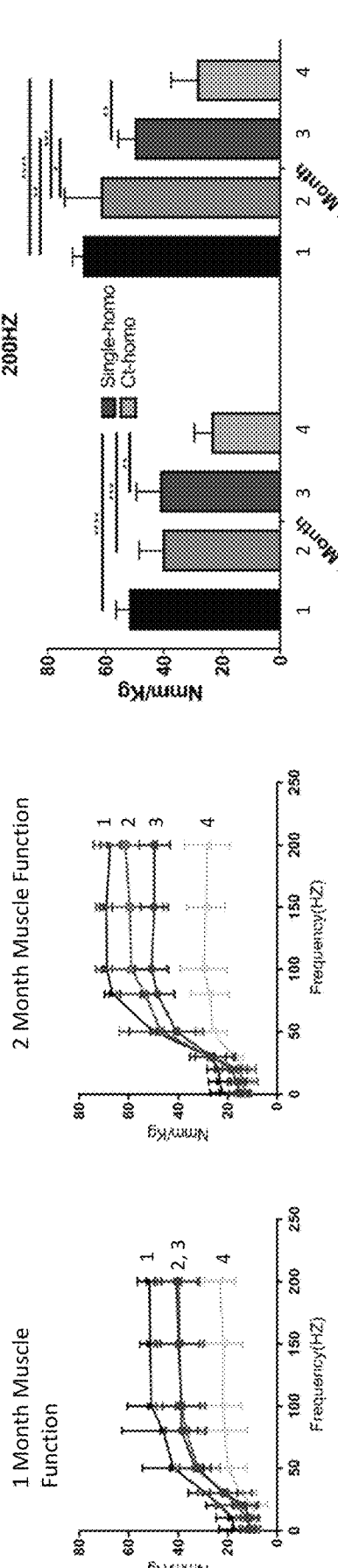
Figure 4D:
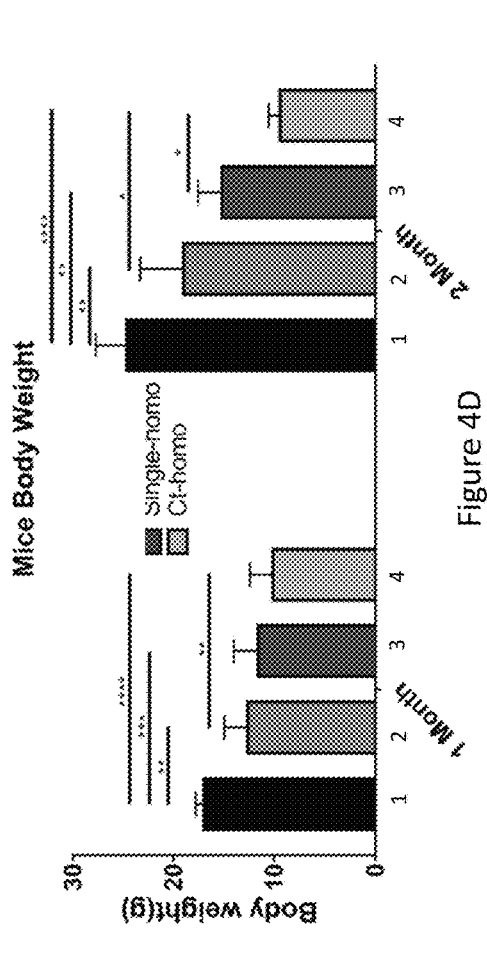

FIG. 4D demonstrates a comparison of overall health and muscle function of mdx/utrn$^{-/-}$ mice systemically treated by dual-cassette AAV and single-cassette AAV treatment. When the muscle function at 1-month and 2-month age with 0 to 200 HZ frequency was tested, both treatment groups had significant improvement at 200 HZ at 1-month age, but no difference as compared dual-cassette AAV and single-cassette AAV treatment. However, the dual-cassette AAV treatment showed a synergistic effect compared to single-cassette AAV at 200 HZ at late age, such as 2-month.

Additionally, early onset (at 1-month age) of improvement in body weight was observed in the dual-cassette AAV treatment, and improvement of body weight of mdx/utm–/– mice treated by dual-cassette AAV and single-cassette AAV treatment was observed at 2-month age.

Discussion

This Example demonstrates the efficacy of gene replacement and anti-inflammation in transgenic and NF-κB/p65 knockdown in a severe DMD mouse model. The results reveal that the mini-dystrophin expression accompanied with NF-kB/p65 knockout in dKO-homo mice background could ameliorate muscle morphology, reduce fibrosis, necrosis, and inflammation. These results imply that genetic reduction of NF-κB might enhance efficacy of mini-dystrophin gene therapy in large animals and clinical trials, highlighting its application for gene therapy to DMD patients through the combinational dystrophin gene replacement and anti-inflammation.

All references, including publications, patent applications, and patents, cited herein are hereby incorporated by reference to the same extent as if each reference were individually and specifically indicated to be incorporated by reference and were set forth in its entirety herein. These include, but are not limited to, the following references:

Acharyya, et al. *J. Clin. Invest.*, 2007, April; 117(4):889-901

Bing Wang, et al., *Journal of Orthopaedic Research,* 2009, 27:4,421-42. PMID: 18973234

Bing Wang, et al., *Gene Ther.,* 2008, 15:1489-1499, PMID: 18563184,

Bing Wang, et al., *Proc. Natl. Acad. Sci. USA.,* 2000, 97(25):13714-13719, PMID: 11095710, Duan, DS, *Mol. Ther.* 2018, 26:2337-2356, Lee, Ui Jin et al., *Mol Biol Rep* (2008) 35:291-298

Jayandharan, et al., *PNAS (USA)*, 2011 Mar. 1; 108(9):3743-8,

Jutooru, Indira et al., *J. Biol. Chem.* (2010), 285: 25332-25344

Komegay J N, et al., *Molecular Therapy.* 2010, 18(8):1501-1508, PMID: 20517298, Mendell, et al., *N. Engl. J. Med.* 2010 Oct. 7; 363(15):1429-37,

20

Qing Yang, et al. *Gene Ther.* 2012, 19:1196-1204, PubMed PMID: 22278411,

Ying Tang, et al. *Gene Ther.* 2010, 17:1476-1483, PubMed PMID: 20720575,

Xi Yin, et al. *Muscle Nerve.* 2017, 56:759-767,

Xiao, et al., *J. Virol.* 1998; 72(3):2224-32. PubMed PMID: 9499080, and

Xiaodong Mu, et al. *Human Mol. Genet.* 2015, 24:2923-2937.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A dual-cassette gene vehicle comprising cassettes for expression of both a mini-dystrophin gene and NF-κB/p65-shRNA gene in cardiac muscle tissue and skeletal muscle tissue, which is an adeno-associated viral (AAV) vector, wherein the mini-dystrophin gene is operably linked to a construct comprising a muscle-specific first promoter and a modified Mcken (MCK) promoter enhancer and wherein the NF-κB/p65-shRNA gene is under the control of a second promoter, and wherein the mini-dystrophin gene comprises the nucleotide sequence of any one of SEQ ID NO: 2, 3, or 27, or a nucleotide sequence at least 90% identical to any one of SEQ ID NO: 2, 3, or 27 which encodes the same amino acid sequence that is encoded by SEQ ID NO: 2, 3, or 27.

2. The gene vehicle of claim 1, which comprises the sequence of SEQ ID NO: 1 or SEQ ID NO: 23.

3. The gene vehicle of claim 1, which comprises the sequence of SEQ ID NO: 25 or SEQ ID NO: 26.

4. A dual-cassette gene vehicle comprising cassettes for expression of both a mini-dystrophin gene and NF-κB/p65-shRNA gene in cardiac muscle tissue and skeletal muscle tissue, which is an adeno-associated viral (AAV) vector, wherein the mini-dystrophin gene is operably linked to a construct comprising a muscle-specific first promoter and a modified Mcken (MCK) promoter enhancer and wherein the NF-κB/p65-shRNA gene is under the control of a second promoter, wherein the modified MCK promoter enhancer comprises the sequence of SEQ ID NO: 14.

5. A dual-cassette gene vehicle comprising cassettes for expression of both a mini-dystrophin gene and NF-κB/p65-shRNA gene in cardiac muscle tissue and skeletal muscle tissue, which is an adeno-associated viral (AAV) vector, wherein the mini-dystrophin gene is operably linked to a construct comprising a muscle-specific first promoter and a modified Mcken (MCK) promoter enhancer and wherein the NF-κB/p65-shRNA gene is under the control of a second promoter, wherein the muscle-specific first promoter comprises the sequence of SEQ ID NO: 15.

6. The gene vehicle of claim 1, wherein the second promoter is an U6 promoter.

7. The gene vehicle of claim 1, wherein the second promoter comprises the sequence of SEQ ID NO: 18.

8. The gene vehicle of claim 1, wherein the NF-κB/p65-shRNA comprises the sequence of SEQ ID NO:17, SEQ ID NO:22, or SEQ ID NO:24.

9. A pharmaceutical composition comprising the gene vehicle of claim 1 and a pharmaceutically acceptable carrier.

10. The pharmaceutical composition of claim 9, which is formulated for injection.

11. A method for ameliorating Duchenne muscular dystrophy (DMD), the method comprising administrating the gene vehicle of claim 1 or a pharmaceutical composition thereof to a patient or subject who is suffering from or at risk of developing DMD in an amount and at a location to ameliorate DMD.

12. The method of claim 11, wherein the gene vehicle or the pharmaceutical composition is administered by intraperitoneal injection.

13. The method of claim 11, wherein the patient is suffering from DMD.

14. A pharmaceutical composition comprising the gene vehicle of claim 4 and a pharmaceutically acceptable carrier.

15. The pharmaceutical composition of claim 14, which is formulated for injection.

16. A pharmaceutical composition comprising the gene vehicle of claim 5 and a pharmaceutically acceptable carrier.

17. The pharmaceutical composition of claim 16, which is formulated for injection.

18. The gene vehicle of claim 1, wherein the mini-dystrophin gene comprises the nucleotide sequence of any one of SEQ ID NO: 2, 3, or 27, or a nucleotide sequence at least 99% identical to any one of SEQ ID NO 2, 3, or 27 which encodes the same amino acid sequence that is encoded by SEQ ID NO: 2, 3, or 27.

19. The gene vehicle of claim 1, wherein the mini-dystrophin gene comprises the nucleotide sequence of any one of SEQ ID NO: 2, 3, or 27, or a nucleotide sequence at least 99.9% identical to any one of SEQ ID NO 2, 3, or 27 which encodes the same amino acid sequence that is encoded by SEQ ID NO: 2, 3, or 27.

20. The gene vehicle of claim 1, wherein the mini-dystrophin gene comprises the nucleotide sequence of any one of SEQ ID NO: 2, 3, or 27.

21. The gene vehicle of claim 1, wherein the mini-dystrophin gene consists of the nucleotide sequence of any one of SEQ ID NO: 2 or 27.

22. The gene vehicle of claim 1, wherein the mini-dystrophin gene comprises the nucleotide sequence of SEQ ID NO: 27, a nucleotide sequence at least 99% identical to SEQ ID NO: 27 which encodes the same amino acid sequence that is encoded by SEQ ID NO: 27.

23. The gene vehicle of claim 1, wherein the mini-dystrophin gene consists of the nucleotide sequence of SEQ ID NO: 27.

\* \* \* \* \*